(12) United States Patent
Weidemaier et al.

(10) Patent No.: US 11,016,095 B2
(45) Date of Patent: *May 25, 2021

(54) ASSAYS USING SURFACE-ENHANCED RAMAN SPECTROSCOPY (SERS)-ACTIVE PARTICLES

(71) Applicant: BECTON DICKINSON AND COMPANY, Franklin Lakes, NJ (US)

(72) Inventors: Kristin Weidemaier, Raleigh, NC (US); Christian Sandmann, Wayne, NJ (US); William Shannon Dillmore, Raleigh, NC (US); James L. Schram, Knightdale, NC (US); W. William Stewart, Cary, NC (US); Robert E. Pearson, Durham, NC (US); Helen Hsieh, Durham, NC (US); Steven Keith, Chapel Hill, NC (US); Rajendra R. Bhat, Raleigh, NC (US); Andrea Liebmann-Vinson, Wake Forest, NC (US); Adam Craig Curry, Raleigh, NC (US); Alexander G. Lastovich, Raleigh, NC (US)

(73) Assignee: BECTON DICKINSON AND COMPANY, Franklin Lakes, NJ (US)

(*) Notice: Subject to any disclaimer, the term of this patent is extended or adjusted under 35 U.S.C. 154(b) by 156 days.

This patent is subject to a terminal disclaimer.

(21) Appl. No.: 15/712,972

(22) Filed: Sep. 22, 2017

(65) Prior Publication Data
US 2018/0059118 A1 Mar. 1, 2018

Related U.S. Application Data

(62) Division of application No. 12/531,508, filed as application No. PCT/US2008/057700 on Mar. 20, 2008, now Pat. No. 9,823,253.

(60) Provisional application No. 61/013,740, filed on Dec. 14, 2007, provisional application No. 60/976,015, filed on Sep. 28, 2007, provisional application No. 60/895,807, filed on Mar. 20, 2007.

(51) Int. Cl.
G01N 33/58 (2006.01)
G01N 21/65 (2006.01)
G01N 33/543 (2006.01)

(52) U.S. Cl.
CPC ......... *G01N 33/587* (2013.01); *G01N 21/658* (2013.01); *G01N 33/54333* (2013.01)

(58) Field of Classification Search
None
See application file for complete search history.

(56) References Cited

U.S. PATENT DOCUMENTS

| | | |
|---|---|---|
| 5,266,498 A | 11/1993 | Tarcha et al. |
| 5,472,881 A | 12/1995 | Beebe et al. |
| 5,860,937 A | 1/1999 | Cohen |
| 5,906,744 A | 5/1999 | Carroll et al. |
| 5,945,281 A | 8/1999 | Prabhu |
| 6,127,120 A | 10/2000 | Graham et al. |
| 6,154,708 A | 11/2000 | Koashi |
| 6,344,272 B1 | 2/2002 | Oldenburg et al. |
| 6,383,397 B1 | 5/2002 | Kojima |
| 6,514,415 B2 | 2/2003 | Hatch et al. |
| 6,514,767 B1 | 2/2003 | Natan et al. |
| 6,548,168 B1 | 4/2003 | Mulvaney et al. |
| 6,685,986 B2 | 2/2004 | Oldenburg et al. |
| 6,699,724 B1 | 3/2004 | West et al. |
| 6,821,789 B2 | 3/2004 | Augello et al. |
| 6,913,825 B2 | 7/2005 | Ostafin et al. |
| 7,002,679 B2 | 2/2006 | Brady et al. |
| 7,192,778 B2 | 3/2007 | Natan |
| 2001/0002315 A1 | 5/2001 | Schultz et al. |
| 2001/0055764 A1 | 12/2001 | Empedocies et al. |
| 2002/0155507 A1 | 10/2002 | Bruchez et al. |
| 2003/0166297 A1 | 9/2003 | Natan et al. |
| 2003/0211488 A1 | 11/2003 | Mirkin et al. |
| 2004/0038318 A1 | 2/2004 | Bell |
| 2005/0074779 A1 | 4/2005 | Tuan |
| 2005/0148098 A1 | 7/2005 | Su et al. |
| 2005/0158870 A1 | 7/2005 | Natan et al. |
| 2005/0217424 A1 | 10/2005 | Natan |
| 2005/0248758 A1 | 11/2005 | Carron et al. |

(Continued)

FOREIGN PATENT DOCUMENTS

| | | |
|---|---|---|
| WO | 199607097 A | 3/1996 |
| WO | 2005062982 A2 | 7/2005 |

(Continued)

OTHER PUBLICATIONS

Eliasson, C , et al., "Mutlivariate Evaluation of Doxorubicin Surface-Enhanced Raman Spectra", Spectrochimica Acta Part A: Molecule and Biomolecular Spectroscopy , vol. 57, No. 9, Aug. 1, 2001, 1907-1915.

Gong, Ji-Lai , et al., "Ag/SiO2 Core-Shell Nanoparticle-Based Surface-enhanced Raman Probes for Immunoassay of Cancer maker Using Silica-Coated Magnetic Nanoparticles as Separation Tools", Biosensors and Bioelectronics, vol. 22, No. 7, Feb. 15, 2007, 1501-1507.

Hirsch, L R, et al., "A Whole Blood Immunoassay Using Gold Nanoshells", Analytical Chemistry, American Chemical Society, US vol. 75, No. 10, May 15, 2003, 2377-2381.

(Continued)

*Primary Examiner* — Amanda Haney
(74) *Attorney, Agent, or Firm* — Botos Churchill IP Law LLP

(57) ABSTRACT

Disclosed herein are diagnostic assays using surface enhanced Raman spectroscopy (SERS)-active particles, including liquid-based assays; magnetic capture assays; microparticle-nanoparticle satellite structures for signal amplification in an assay; composite SERS-active particles useful for enhanced detection of targets; and sample tubes and processes for using the same.

2 Claims, 20 Drawing Sheets

(56) References Cited

U.S. PATENT DOCUMENTS

| | | | |
|---|---|---|---|
| 2006/0046313 | A1 | 3/2006 | Roth et al. |
| 2006/0054506 | A1 | 3/2006 | Natan et al. |
| 2006/0216835 | A1 | 9/2006 | Moondello |
| 2006/0240572 | A1* | 10/2006 | Carron .............. G01N 21/658 436/524 |
| 2007/0155021 | A1 | 7/2007 | Zhang et al. |

FOREIGN PATENT DOCUMENTS

| | | | |
|---|---|---|---|
| WO | 2006060734 | A2 | 6/2006 |
| WO | 2006073439 | A2 | 7/2006 |
| WO | 2007092941 | A2 | 8/2007 |

OTHER PUBLICATIONS

Iida , et al., Clinica Chimia Acta, Elsevier by, Amsterdam NL, vol. 228, No. 2, Aug. 1. 1994, Aug. 1, 1994, 133-142.
Albrecht, M. G., et al., "Anomalously intense Raman Spectra of pyridine at a silver electrode", J.A.C.S. vol. 99, pp. 5215-5217 (1977).
Allara, David L., et al., "Spontaneously Organized Molecular Assemblies.1. Formation, Dynamics, and Physical Properties of n-Alkanoic Acids Adsorbed from Solution on an Oxidized Aluminum Surface", Langmuir vol. 1, pp. 45-52 (1984).
Breuzard, G. et al., "Surface-enhanced Raman scattering reveals adsoprtion of mitoxantrone on plasm membrance of living cells", Biochem. Biophys. Res, Comm. vol. 320, pp. 615-621 (2004).
Brown, Tom , et al, "Oligonucleotides and Analogues", F. Eckstein (ed.) Oxford Press, pp. 1-11 (1991).
Burwell, Robert L., "Modified silica gels as adsorbents and catalysts", Chemical Technology vol. 4, pp. 370-377 (Jun. 1974).
Campion, Alan , et al., "Surface-enhanced Raman scattering", Chem, Soc. Rev. vol. 27, pp. 241-250 (1998).
Cao, Yun Wei, et al., "DNA-Modified Core-Shell Ag/Au Nanoparticles", J. Am. Chem. Soc. vol. 123, pp. 7961-7962 (2001).
Eltekova, Nina A., et al., "Adsorption of Aromatic Compounds from Solutions on Titanium Dioxide and Silica", Langmuir vol. 3, pp. 951-957 (Feb. 27, 1987).
Emory, Steven R., et al., "Near-Field Surface-Enhanced Raman Spectroscipy on Single Silver Nanoparticles", Anal. Chem. vol. 69, pp. 2631-2635 (1997).
Fleischmann, M. , et al., "Raman Spectra of Pyridiend Adsorbed at a Silver Electrode", Chem. Phys. Let. vol. 26, No. 2, pp. 163-166 (May 15, 1974).
Frens, G. , "Controlled Nucleation for the Regulation of the Particle Size in Mondisperse Gold Suspensions", Nat. Phys. Sci., vol. 241, No. 105, pp. 20-21 (Jan. 1, 1973).
Grabar, Katherine C., et al., "Preparation and Characteization of Au Colloid Monolayers", Anal. Chem. vol. 67, pp. 735-743 (1995).
Hickman, James J., et al., "Combining Spontaneous Molecular Assembly with Microfabrication to Pattern Surfaces: Selective Binding of Isonitriles to Platinum Microwisres and Characterization by Electrochemistry and Surface Spectroscopy", J. Am. Chem. Soc. vol. 111, pp. 7271-7272 (1989).
Hubbard, Arthur T., et al., "Electrochmistry of Well-Defined Surfaces", Acc. Chem. Res. vol. 13, pp. 177-184 (1980).
Iler, Ralph K, "Solubility, Polymerization, Colloid and Surface Properties, and Biochemistry", The Chemistry of Silica, Chapter 6, pp. 622-729 (1979).
Jackson, J. B.,et al., "Surface-enhanced Raman scattering on tunable plasmonic nanoparticle substrates", Proc. Natl. Acad. Sci. U.S.A. vol. 101 No. 52, pp. 17930-17935 (Dec. 28, 2004).
Jeanmaire, David L., et al., "Surface Raman Spectroelectrochemistry", J. Electroanal. Chem. vol. 84, No. 1, pp. 1-20 (1977).
Katrin, Kneipp , et al., "Single Molecule Detection Using Surface-Enhances Raman Scattering (SERS)", Phys. Rev. Lett. vol. 78, No. 9, pp. 1667-1670 (Mar. 3, 1997).

Kneipp, Katrin , et al., "Surface-enhanced RamanSpectroscipy in Single Living Cells Using Gold Nanoparticles", App. Spectrosc., vol. 56 No. 2, pp. 150-154 (2002).
Lee, Haiwon , et al., "Adsorption of Ordered Zirconium Phosphonate Multilayer Films on Silicon and Gold Surfaces", J. Phys. Chem. vol. 92 No. 9, pp. 2597-2601(1988).
Maoz, Rivka , et al., "Penetration-Controlled REactions in Organized Monolayer Assemblies", Langmuir vol. 3, pp. 1045-1051 (1987).
Maoz, Rivka , et al., "Penetration-Controlled REactions in Organized Monolayer Assemblies 1. Aqueous Permanganate Interaction with Monlayer and Multilayer Films of Long-Chain Surfactants", Langmuir vol. 3, No. 6, pp. 1034-1044(1987).
Matteucci, M. D., et al., "Synthesis of Deoxyoligonucleotides on a Polymer Support", J. Am. Chem. Soc. vol. 103, pp. 3185-3191 (1981).
Morjani, Hamid , et al., "Molecular and Cellular Interactions between Intoplicine, DNA, and Topoisomerase", Cancer Research, vol. 53, pp. 4784-4790 (Oct. 15, 1993).
Mucic, Robert C., et al., "DNA-Directed Synthesis of Binary Nanoparticle Network Materials", J. Am. Chem. Soc. vol. 120, pp. 12674-12675 (1998).
Mucic, Robert C., et al , "Synthesis and Characterizaion of DNA with Ferrocenyl Groups Attacvhed to Their 5'termini: Electrochemical Characterization of a Redox-active Nucleotide Manolayer", pp. 555-557 (1996).
Nabiev, I. R., et al., "SElective analysis of antitumor drug interaction with living cancer celslas probe by surface-enhanced Raman spectroscopy", European Biophys. J. vol. 19, pp. 311-316 (1991).
Ni, Jing et al., "Immunoassay Readout Method Using Extrinsic Raman Labels Adsorbed on Immunogold Colloids", Anal. Chem. vol. 71, pp. 4903-4908 (1999).
Nicewarner-Pena, Sheila R., et al., "Submicrometer Metallic Barcodes, Science, vol. 294", pp. 137-141 (Oct. 5, 2001).
Nie, Shuming , et al., "Probing Single Molecules and Single Nanoparticles by Surface-Enhanced Raman Scattering, Science vol. 275", pp. 1102-1106 (Feb. 21, 1997).
Nuzzo, Ralph G., et al., "Spontaneously Organized Molecular Assemblies, 3. Preparation and Properties of Solution Adsorbed Monolayers of Organic Disulfides on Gold Surfaces," J. Am. Chem. Soc., pp. 2358-2368 (1987).
Olsvik, Orjan , et al., "Magnetic Separation Techniques in Diagnostic Microbiology," Clinical Microbiology Reviews, vol. 7, pp. 43-54 (Jan. 1994).
Polanczyk, Carisi A., et al., "Cardiac Troponin I as a Predictor of Major Cardiac Events in emergency department patients with acute chest pain", J. Am. Coll. Cardiol., vol. 32, pp. 8-14 (1998).
Rohr, Thomas E., et al., "Immunoassay Employing Surface-Enhanced Raman Spectroscopy", Anal. Biochem. vol. 182, pp. 388-398(1989).
Sambrook, J. , Molecular Cloning, A Laboratory Manual, 2nd Edition, pp. 1-32 (contents) (1989).
Soriaga, Manuel P., et al., "Determination of the Orientation of Aromatic Molecules," J. Am. Chem. Soc., vol. 104, No. 14, pp. 3937-3945 (1982).
Talley, Chad E., et al., "Nanoparticle-Based Surface-Enhanced Raman Spetroscopy", NATO Advanced Study Institute: Advances in Biophotonics, pp. 182-195 (Jan. 6, 2005).
Timmons, C. O., et al., "Investigation of Fatty Acid Monolayers on Metals by Contact", Phys. Chem., vol. 69, pp. 984-990 (1965).
Tkachenko, Alexander G., et al., "Cellular Trajectories of Peptide-Modified Gold Particle Complexes: Comparison of Nuclear Localization Signals and Peptide Transduction Domains", Bioconjugate Chem., vol. 15, pp. 482-490 (2004).
Tompkins, Harland G., et al., "The Study of Gas-Solid Interaction of Acetic Acid with a Cuprous Oxide Surface Using Reflection-Absorlation Spectroscopy", Journal of Colloid and Interface Science, vol. 49, No. 3, pp. 410-421 (1974).
Tuchin, Valerie V. (Ed.), et al., "Handbook of optical biomedical diagnostics (contents only) vol. 1 and 2", SPIE Press (TOC only) vols. 1 and 2, pp. i-xiii (2002).

(56) References Cited

OTHER PUBLICATIONS

Walton, Ian D., et al., "Particles fo Multiplexed Analysis in Solution: Detection and Identification of Striped Metallic Paticles Using Optical Microscopy", Anal. Chem. vol. 74, pp. 2240-2247 (2002).
Wasserman, Stephen R., et al., "Structure and Reactivity of Alkylsiloxane Monolayers Formed by Reaction of Alkyltrichlorosilanes on Silicon Substrates", pp. 1074-1087 (1989).
Whitesides, George M., et al., "Self-Assembled Monolayers and Lithography", Proc. Robert A. Welch Foundation 39th Conference on Chemical Research Nanophase Chemistry, Langmuir, vol. 5, pp. 109-121 (1989).

\* cited by examiner

ASSAYS USING SURFACE-ENHANCED RAMAN SPECTROSCOPY (SERS)-ACTIVE PARTICLES

CROSS-REFERENCE TO RELATED APPLICATIONS

The present application is a divisional of U.S. patent application Ser. No. 12/531,508, filed on Jan. 29, 2010, issued as U.S. Pat. No. 9,823,253, which is a national phase entry under 35 U.S.C. § 371 of International Application No. PCT/US08/57700, filed Mar. 20, 2008, published in English, which claims priority from U.S. Provisional Application Ser. No. 61/013,740, filed Dec. 14, 2007, 60/976,015, filed Sep. 28, 2007, and 60/895,807, filed Mar. 20, 2007, all of which are incorporated herein by reference.

TECHNICAL FIELD

The presently disclosed subject matter relates to diagnostic assays using surface enhanced Raman spectroscopy (SERS)-active particles, including liquid-based assays; magnetic capture assays; microparticle-nanoparticle satellite structures for signal amplification in an assay; composite SERS-active particles useful for enhanced detection of targets; and sample tubes and processes for using the same

BACKGROUND OF THE INVENTION

Various techniques have been developed to detect the presence of one or more analytes in an assay. For example, fluorescent, luminescent, chemiluminescent, or electrochemiluminescent techniques have been used to detect analytes within a biological sample. In many biological assays, including assays where micro- or nanoparticles are used for detecting the presence and/or amount of one or more analytes in a biological sample, the generation of a signaling event is used to detect the presence of the analyte. Such biological assays known in the art, however, have limitations. Thus, it might be advantageous to provide an assay having one or more enhanced characteristics, including, but not limited to, enhanced sensitivity, specificity, accuracy, repeatability, and combinations thereof.

BRIEF SUMMARY OF THE INVENTION

In some embodiments, the presently disclosed subject matter provides liquid-based assays including magnetic capture particles having attached thereto a binding member having an affinity for one or more analytes of interest and SERS-active nanoparticles, also having attached thereto a binding member having an affinity for the one or more analytes of interest. When contacted with a biological sample containing one or more analytes, a magnetic capture particle-analyte-SERS-active nanoparticle complex is formed. The magnetic properties of the magnetic capture particles can be used to localize the magnetic capture particle-analyte-SERS-active nanoparticle complex in a predetermined area within an assay vessel for detecting the SERS signal.

In other embodiments, the presently disclosed subject matter provides a magnetic capture/liquid-based assay incorporating a reference label. In such embodiments, magnetic particles used for the magnetic pull-down are labeled with a reference label capable of producing a detectable signal, in addition to the binding member specific to the analyte of interest. The signal emitted by the SERS-active nanoparticle of the magnetic capture particle-analyte-SERS-active nanoparticle complex can be referenced to that of the reference label attached to the magnetic capture particle to compensate for variations in pellet size, shape, or positioning.

In a further embodiment, a lysis reagent can be used in an assay, such as a liquid-based assay, with or without magnetic pull-down. The use of a lysis reagent can provide an increased signal and/or improved limit of detection for analytes of interest, for example, in biological matrices, such as human blood, plasma, or serum, or in cells.

In yet another embodiment, a method for amplifying a signal in a liquid-based assay is provided. Such methods include adding a second aliquot of a reporter molecule having the same signal-producing capabilities as the reporter molecule, e.g., a SERS-active nanoparticle, already present in the assay solution before the magnetic capture complexes are localized. This second aliquot of reporter molecule has attached thereto one or more binding members having an affinity for the binding member of the reporter molecule present in the assay solution. The second reporter molecule therefore can bind to the first reporter molecule, resulting in a higher signal per magnetic capture particle-analyte-reporter molecule complex.

In other embodiments, methods for improving Raman reference spectra and spectral analysis in magnetic capture/liquid-based assays are provided. In one embodiment, reference spectra of one or more analytes of interest are obtained with the analyte disposed in a magnetized pellet, as opposed to using reference spectra of the analyte obtained in solution. In another embodiment, methods are provided for improving the SERS spectral analysis, including selecting the wavelength region within which the analysis is performed and selecting the components of the spectral fitting procedure, e.g., a least squares fitting technique, based on results from an initial analysis.

In some embodiments, the presently disclosed subject matter provides composite nanostructures, including a composite structure, referred to herein as a "satellite" structure, comprising a plurality of signal-bearing particles, e.g., nanoparticles, bound to a core particle. In other embodiments, a composite structure, referred to herein as a "core-shell" structure, which includes a core particle, an active material, such as a Raman-active material, surrounding the core particle, and one or more shells, such as a metal shell, surrounding the active material is provided. The presently disclosed satellite and core-shell structures can be used to amplify or otherwise enhance a signal in an assay, such as a SERS assay.

In some embodiments, a sample tube designed to form a magnetic particle pellet having a consistent size, shape, and density is provided, wherein the sample tube has dimensions to physically constrain a magnetic particle pellet to a desired size. The sample tube can include an optical window allowing for the detection of optical signals generated from the magnetic particle pellet. A system is provided for forming a magnetic particle pellet that uses a magnet positioned adjacent and below the sample tube. The system can be used in a magnetic capture assay. The presently disclosed subject matter further relates to a method of reliably forming a smaller, denser magnetic particle pellet in a sample tube.

Also provided herein, are representative systems and instrumentation suitable for carrying out the presently disclosed assays.

Certain aspects of the presently disclosed subject matter having been stated hereinabove, which are addressed in whole or in part by the presently disclosed subject matter, other objects will become evident as the description proceeds when taken in connection with the accompanying Examples and Drawings as best described herein below.

BRIEF DESCRIPTION OF THE SEVERAL VIEWS OF THE DRAWINGS

Figure 1:
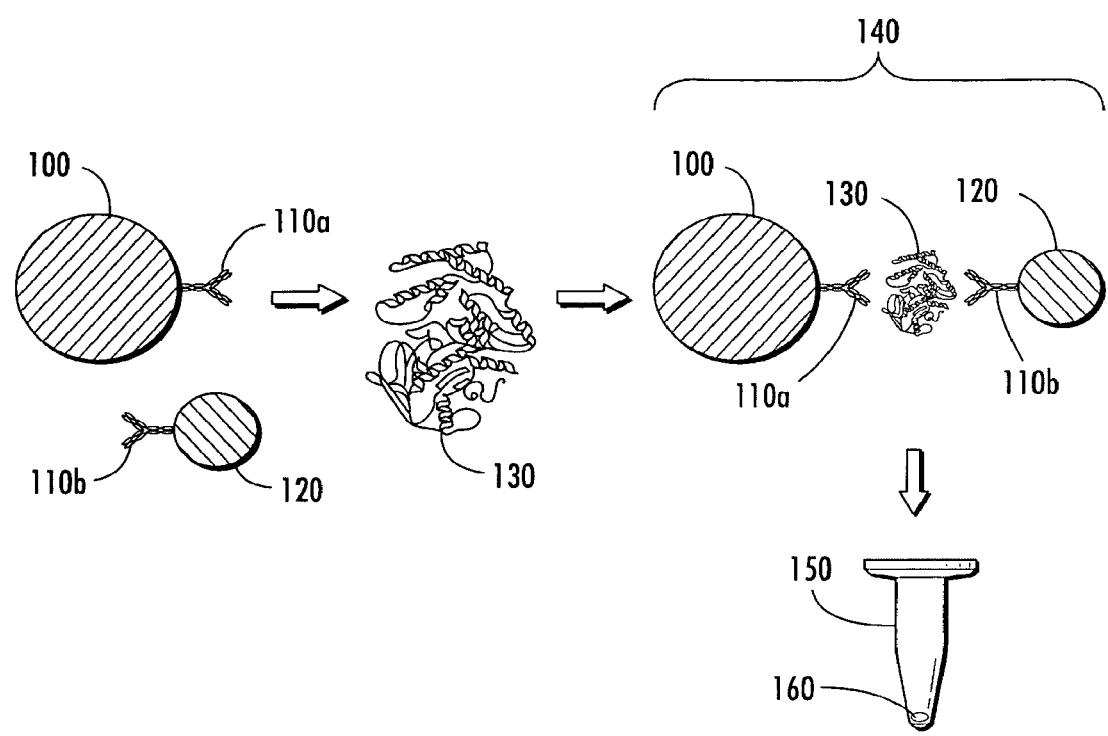
Figure 2:
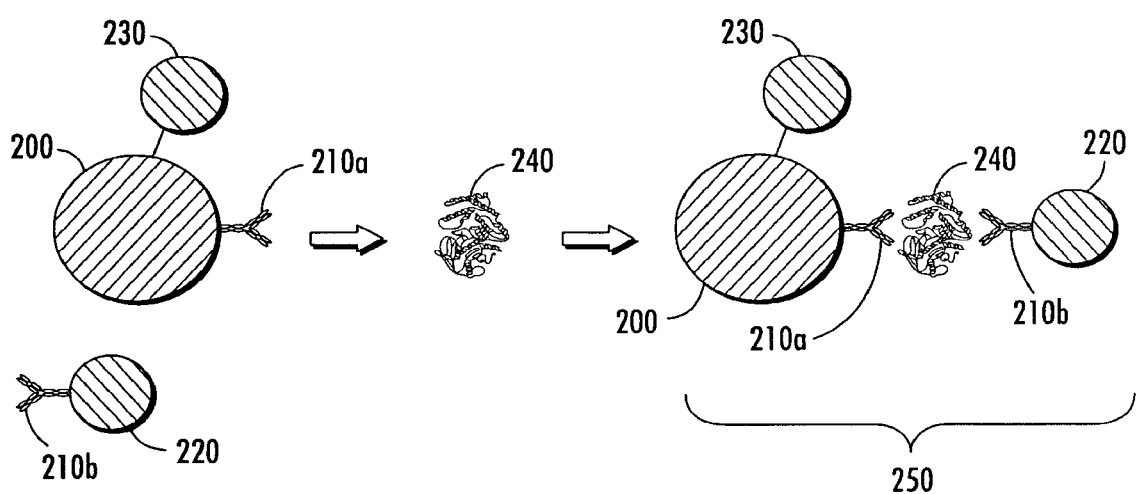
Figure 3:
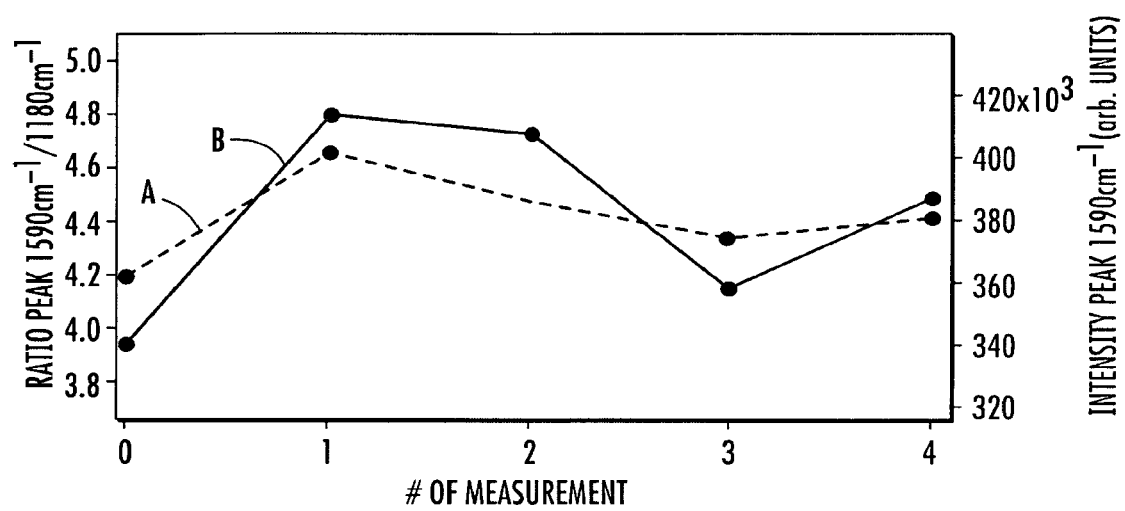
Figure 4:
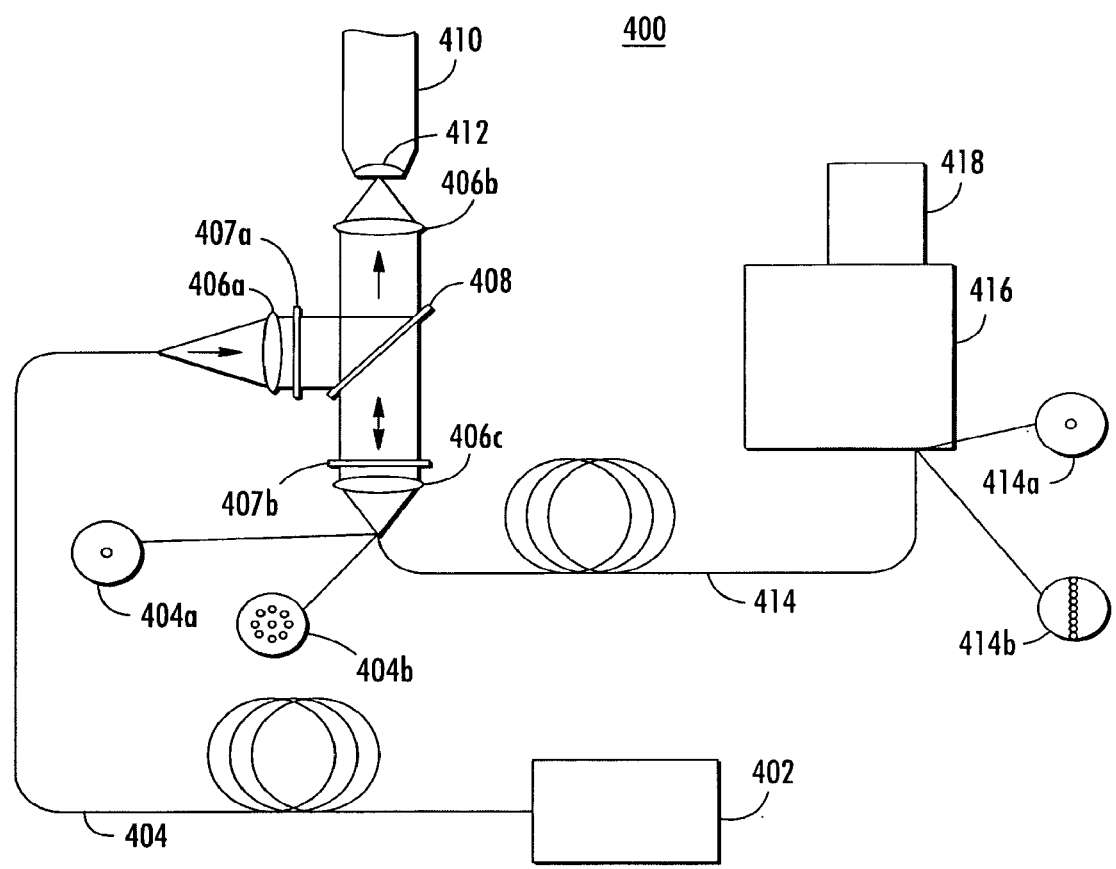
Figure 6:
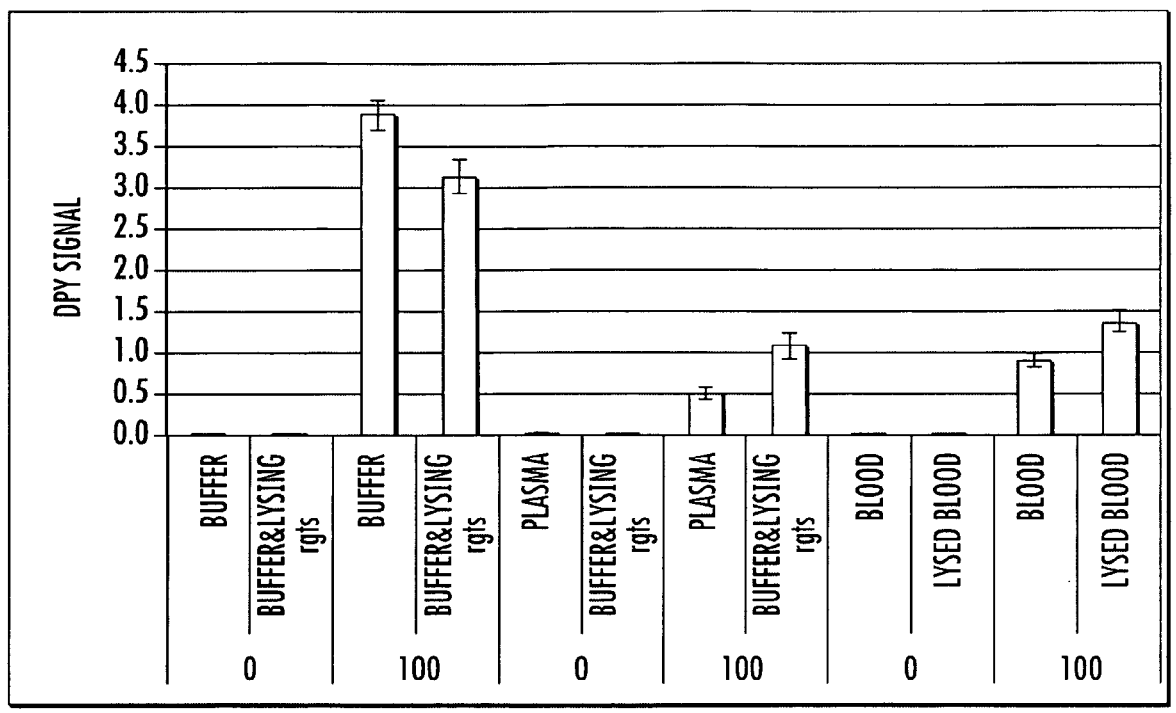
Figure 7:
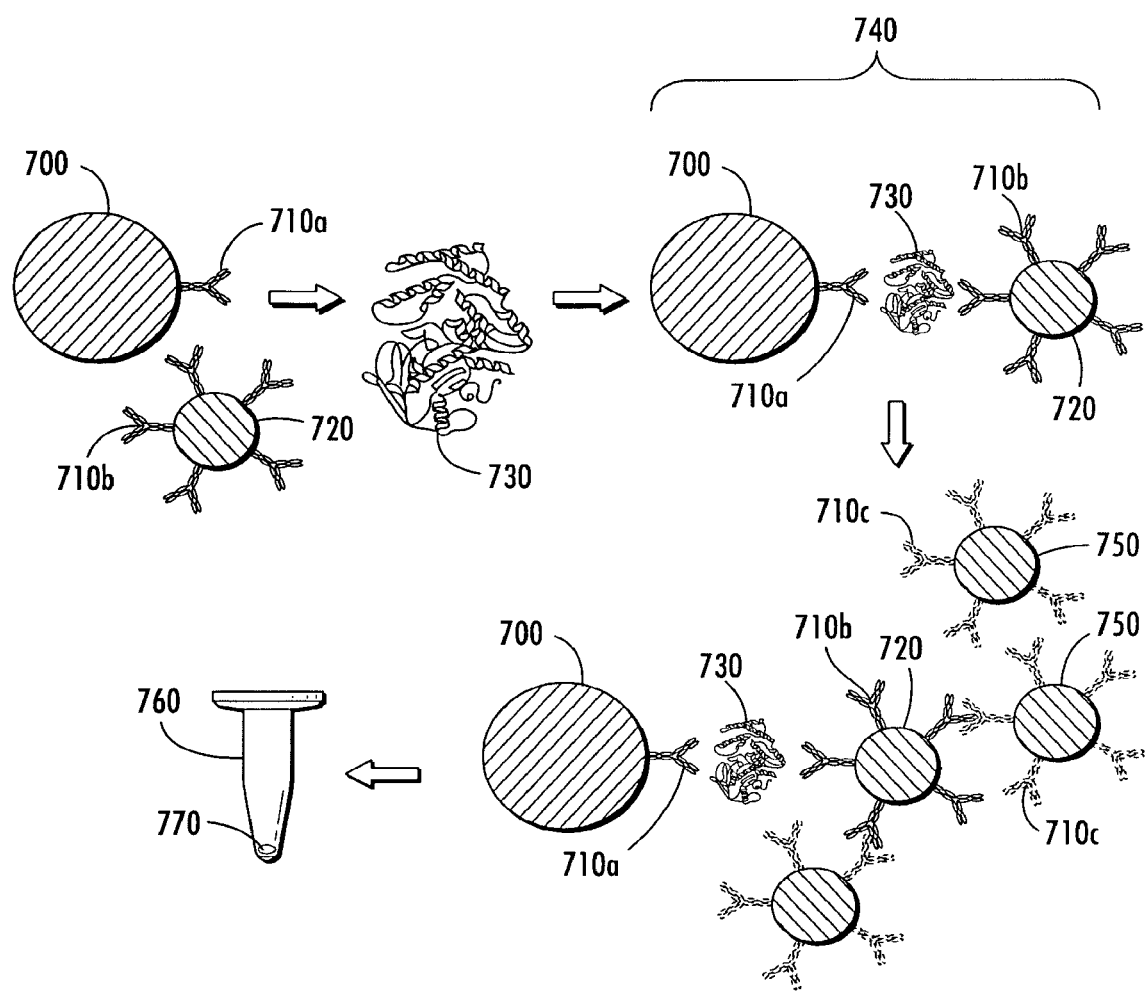
Figure 8A:
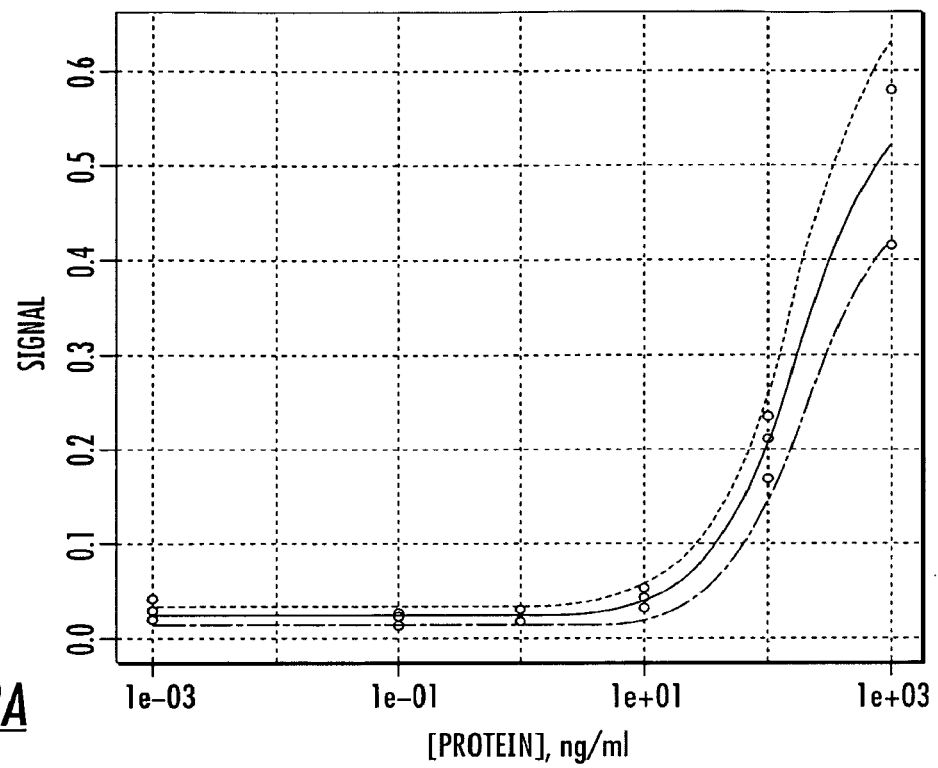
Figure 8B:
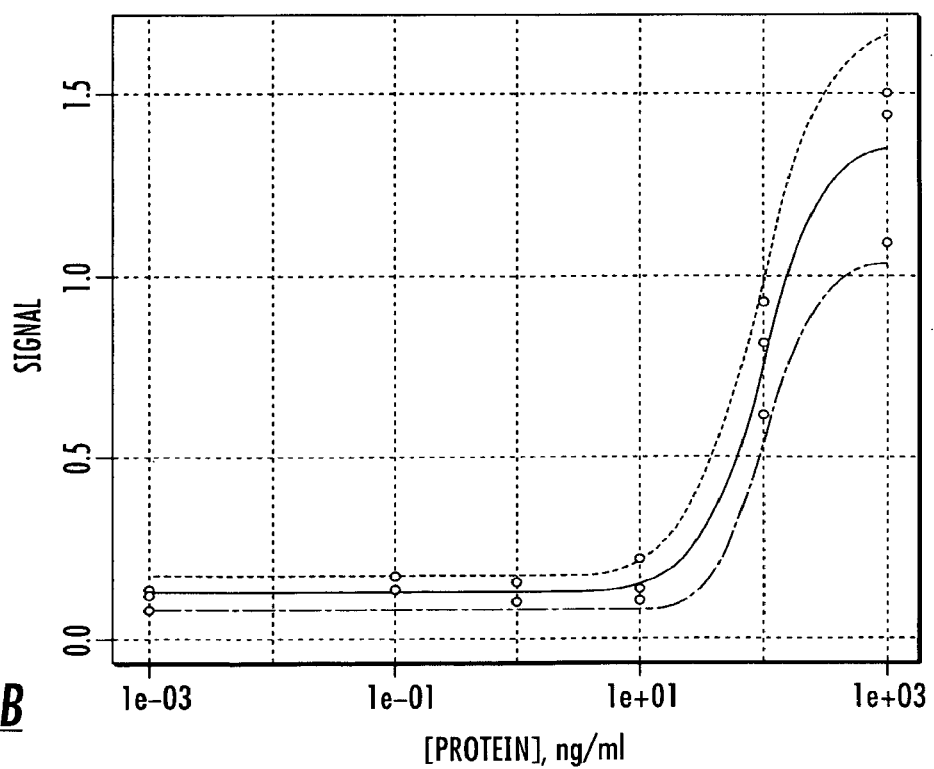
Figure 9:
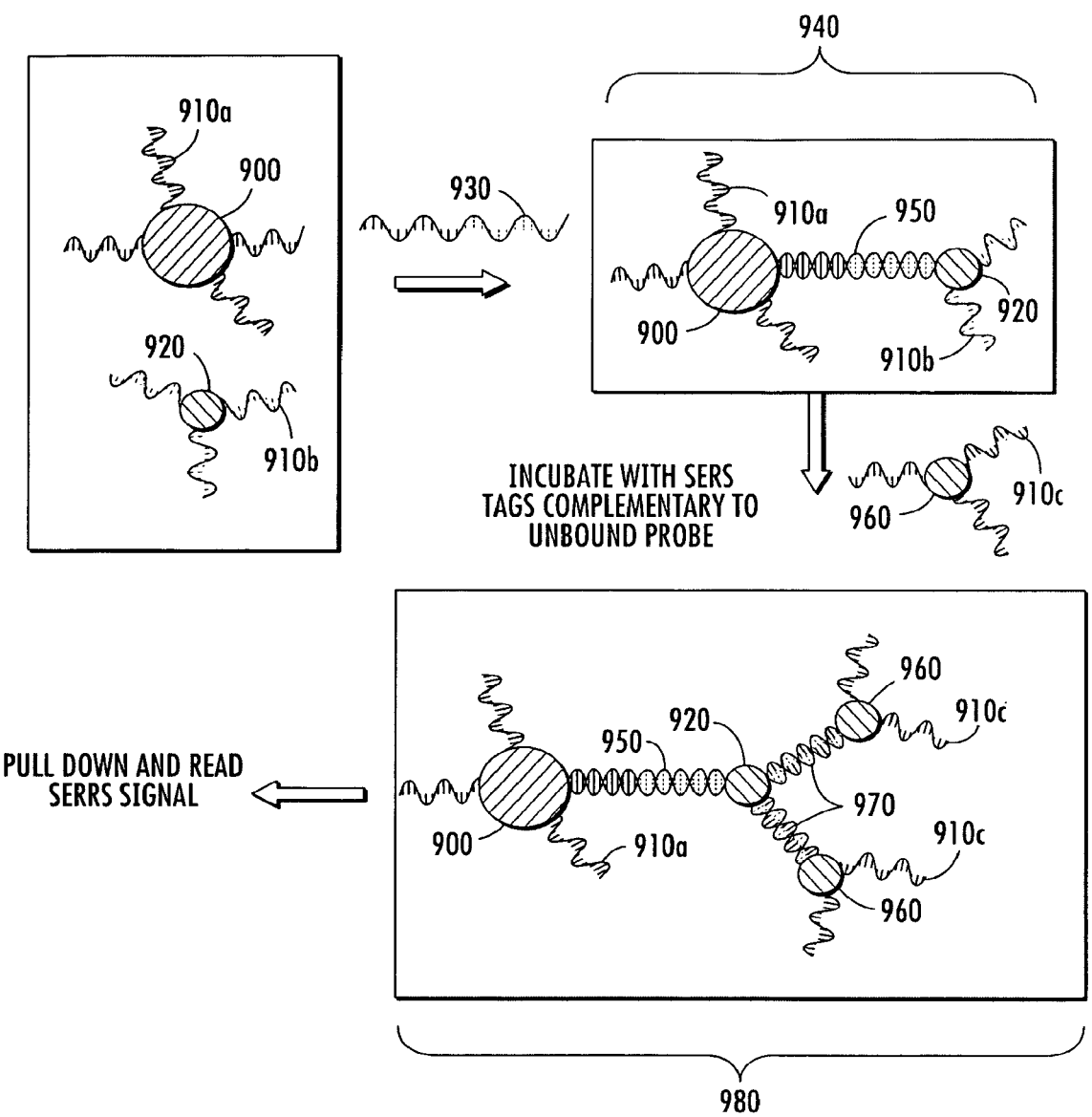
Figure 10A:
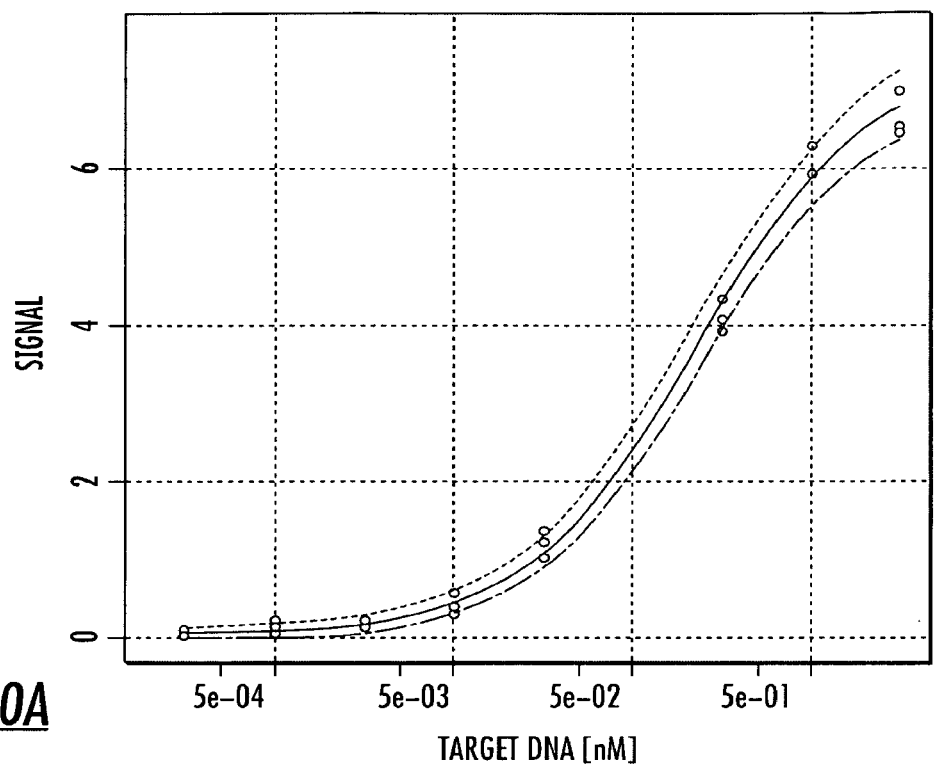
Figure 10B:
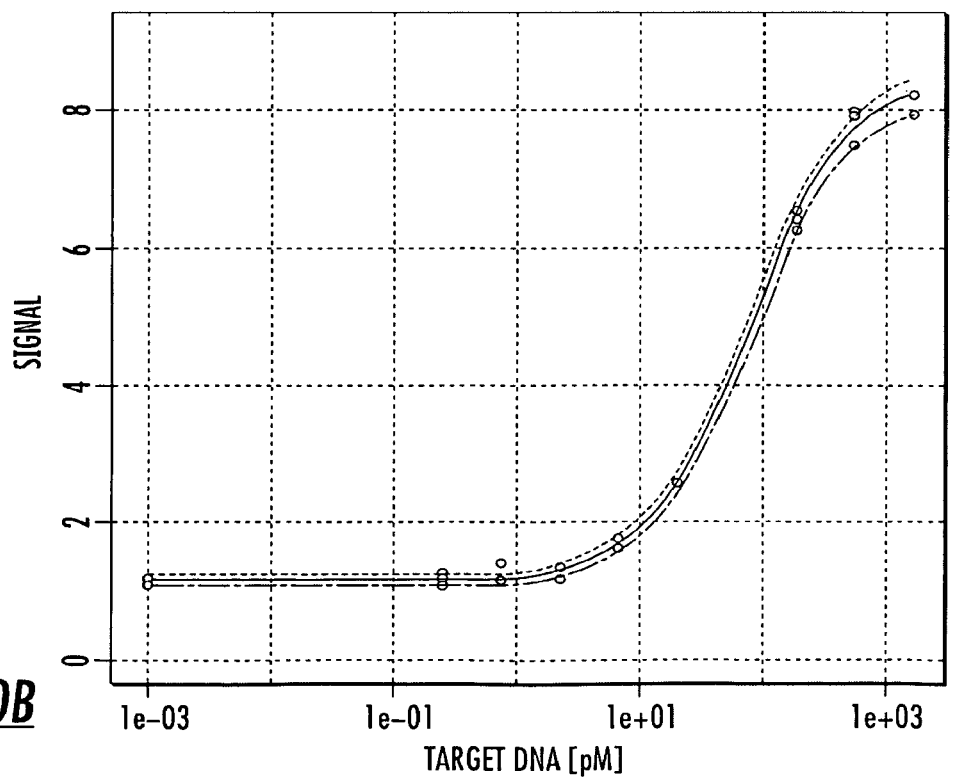
Figure 11A:
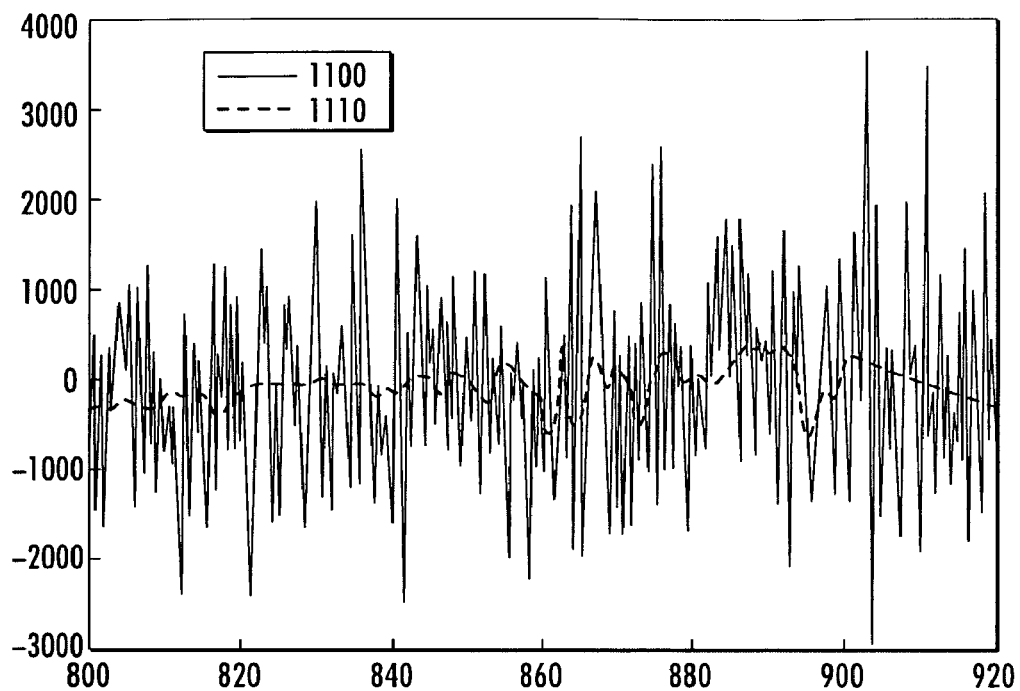
Figure 11B:
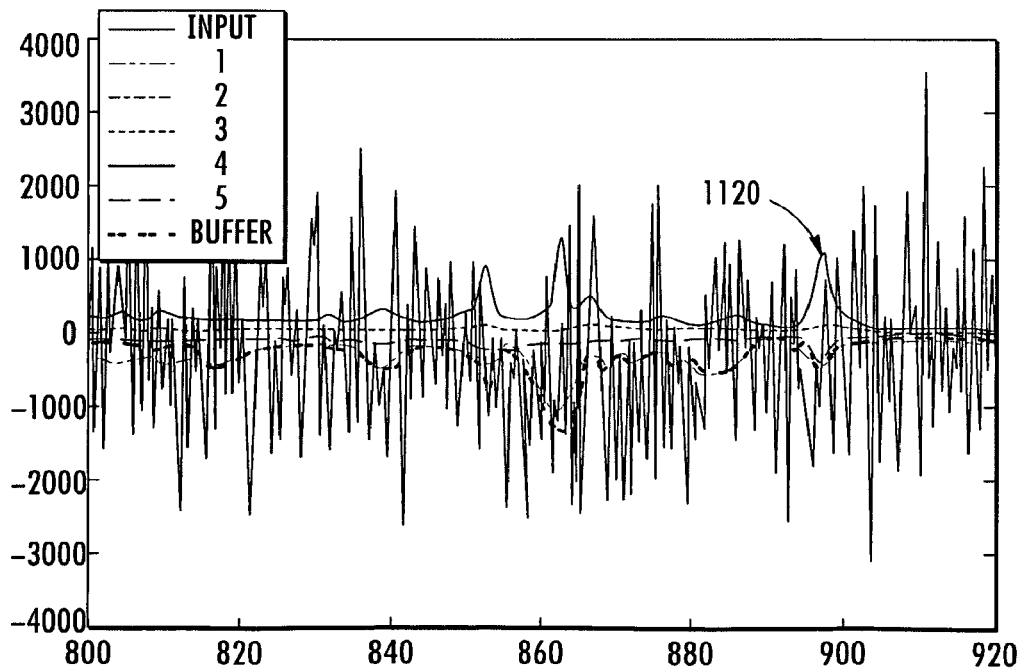
Figure 12A:
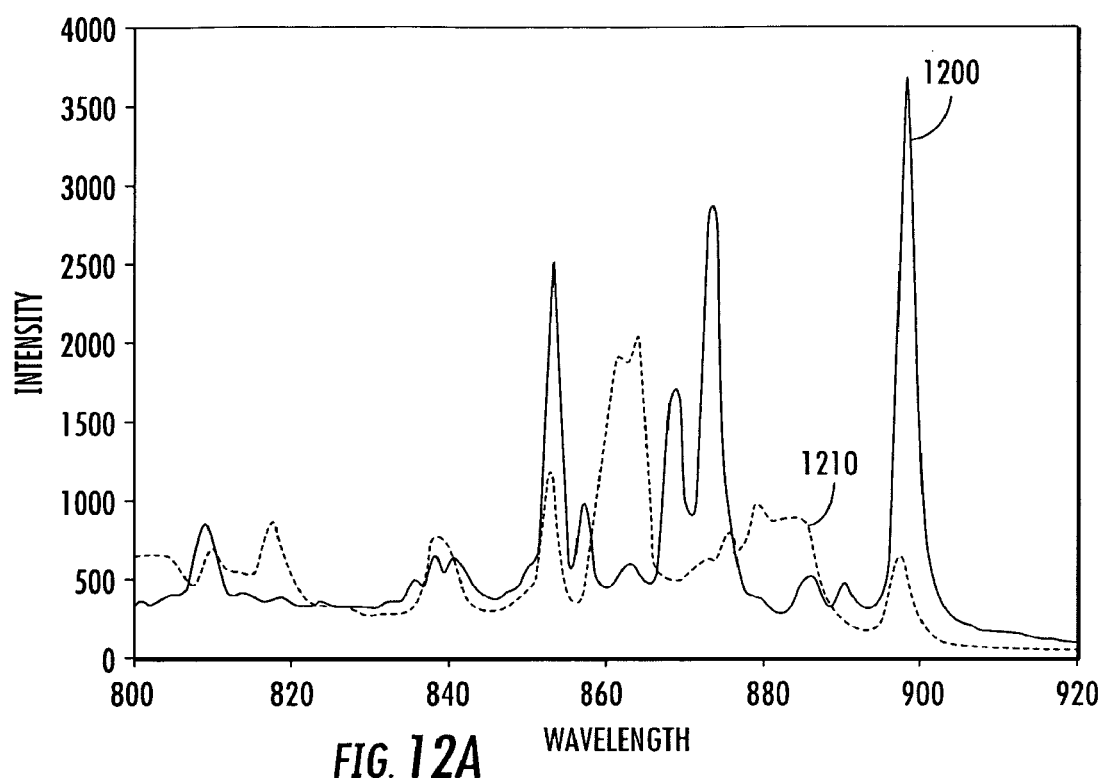
Figure 12B:
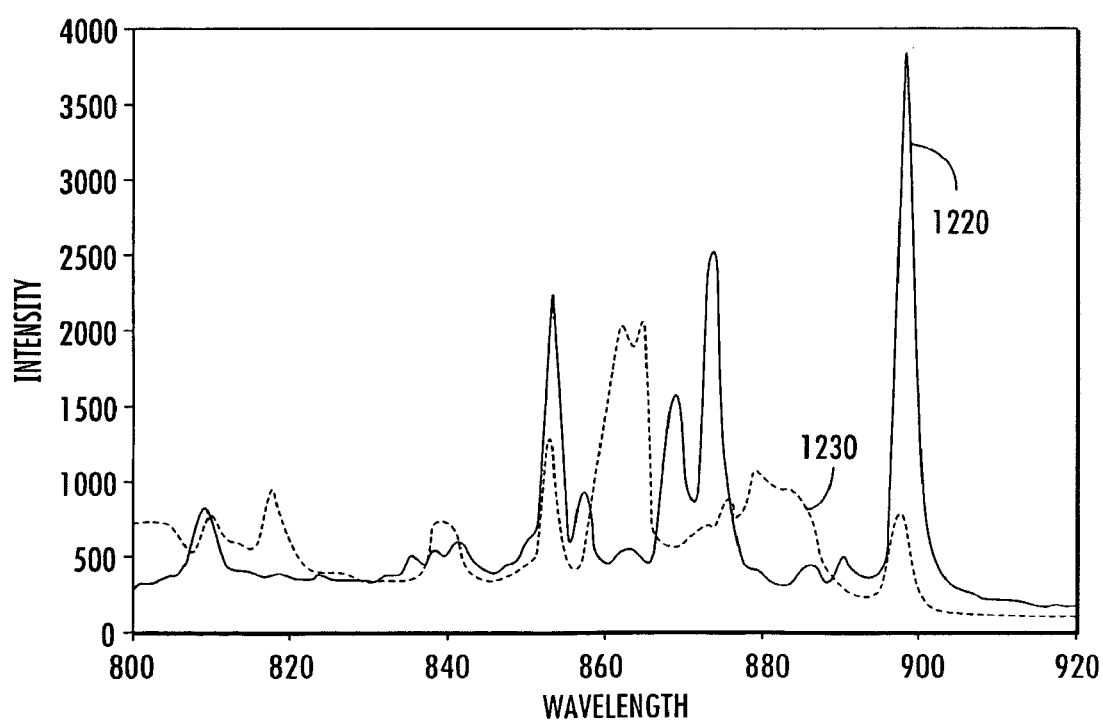

Having thus described the presently disclosed subject matter in general terms, reference will now be made to the accompanying drawings, which are not necessarily drawn to scale, and wherein:

FIG. 1 is a schematic diagram of a representative presently disclosed magnetic capture assay;

FIG. 2 is a schematic diagram depicting the use of a reference label, e.g., a SERS-active nanoparticle, as a reference on a magnetic capture particle;

FIG. 3 is a graphical representation of a comparison of a non-referenced signal and a referenced signal. The non-referenced signal (B) is the peak intensity at 1590 cm$^{-1}$ of a trans-1,2-bis(4-pyrridyl)ethylene (BPE) Raman reporter and the referenced signal (A) is the ratio of the peak intensities at 1590 cm$^{-1}$ and 1180 cm$^{-1}$, which is the peak intensity corresponding to a 4,4'-dipyridyl (DPY) reporter. Note the scale of the left side of the graph corresponds to the referenced signal (A), whereas the scale on the right side of the graph corresponds to the non-referenced signal (B);

FIG. 4 is a schematic diagram of an example of an optical system suitable for use with the presently disclosed assays;

FIGS. 5A-5D are schematic representations of pellet formation by sample tube rotation;

FIG. 6 is a graphical representation of a comparison of the 4,4'-dipyridyl (DPY) reporter signal in buffer, plasma, and lysed blood with and without lysing reagent (rgts);

FIG. 7 is a representative schematic diagram of a presently disclosed assay using a signal amplification method;

FIGS. 8A and 8B are a comparison of liquid-based immunoassays run with identical reagents in the absence of (8A) and the presence of (8B) the presently disclosed signal amplification method;

FIG. 9 is a representative schematic diagram of the presently disclosed amplification method in a polynucleotide detection format;

FIGS. 10A and 10B present results from a DNA hybridization assay in the absence of (10A) and presence of (10B) the presently disclosed signal amplification method;

FIGS. 11A and 11B show that a random signal can be erroneously assigned to input variables due to spurious alignment of features. Normally distributed random noise with a standard deviation of 10,000 was fit using a least-squares routine. In this example, marker 4 was assigned a weight of 0.5 to balance negative weights of other markers;

FIGS. 12A and 12B show representative reference spectra obtained in solution (A) and in a magnetic particle pellet (B). The marker 5 peak (near 865 nm) relative to marker 1 is higher in the pellet, and the shape of the peak at 880 nm is slightly different.

Figure 13:
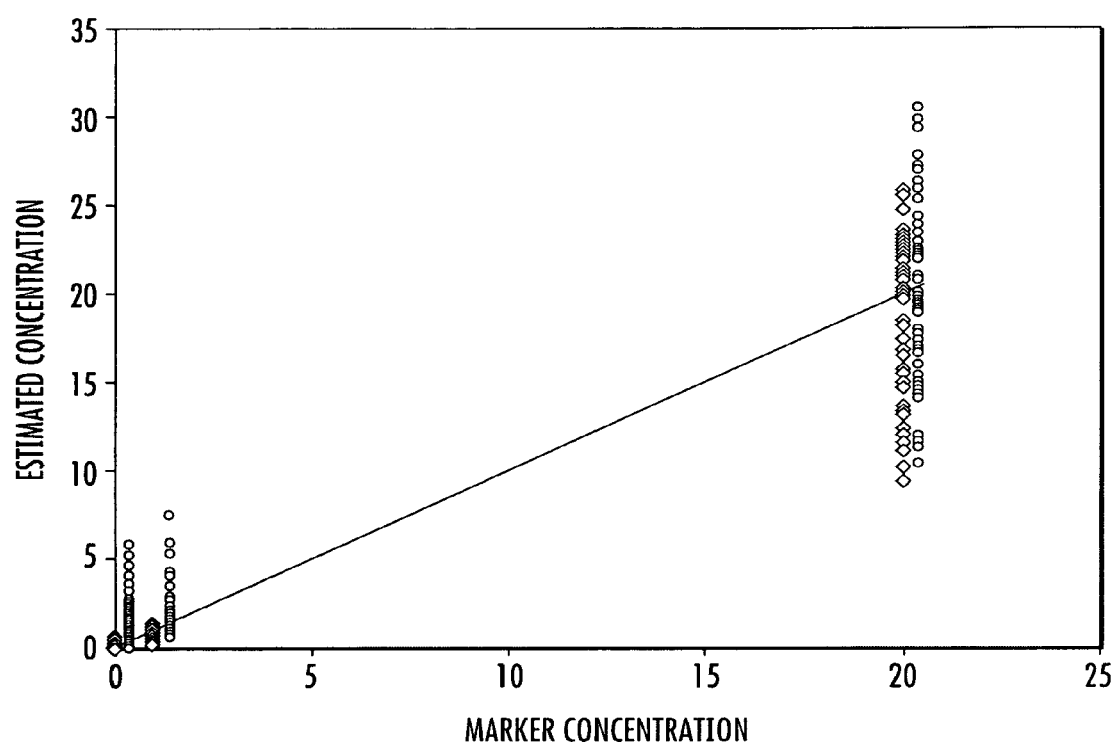
Figure 14:
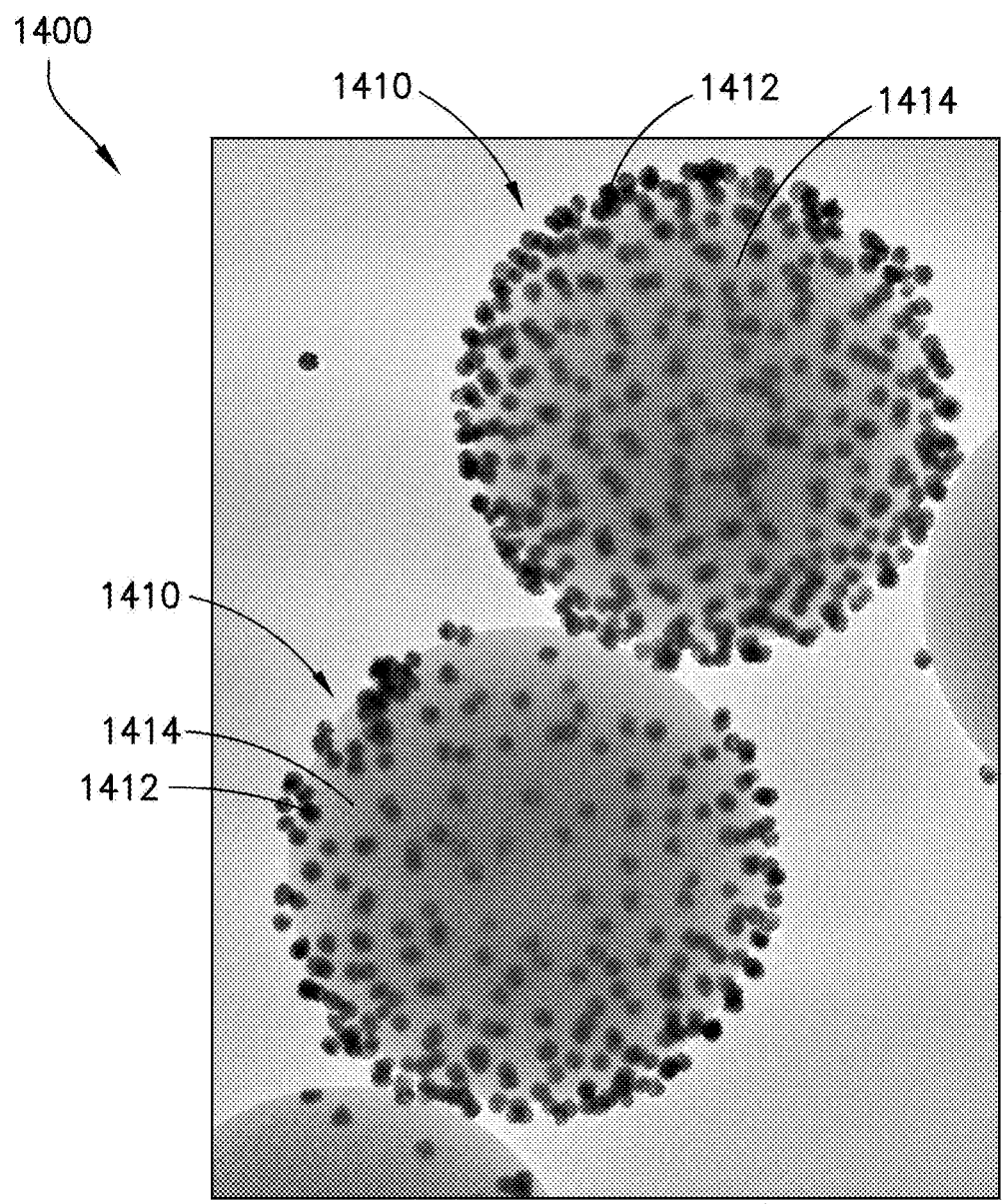
Figure 15:
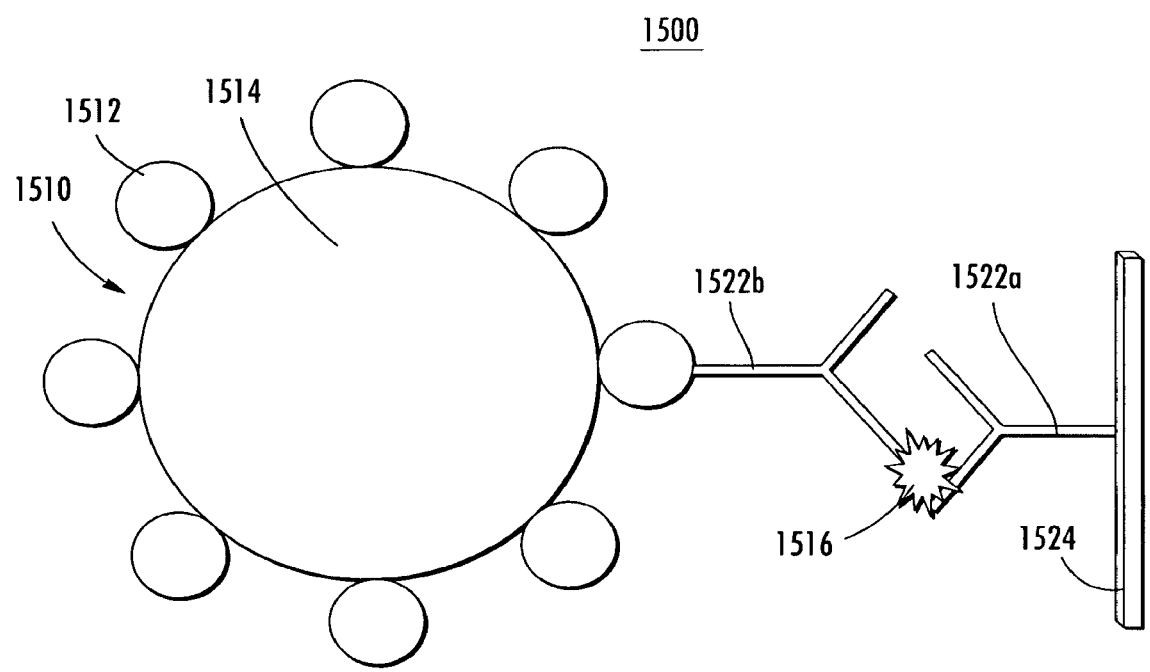
Figure 16A:
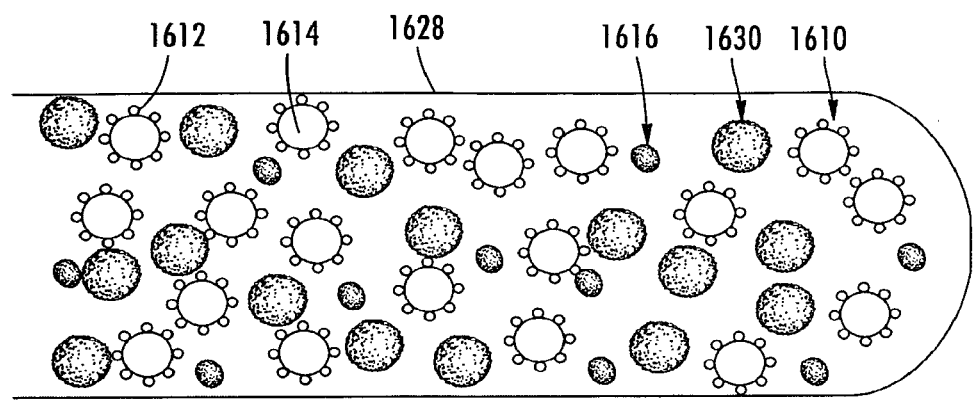
Figure 16B:
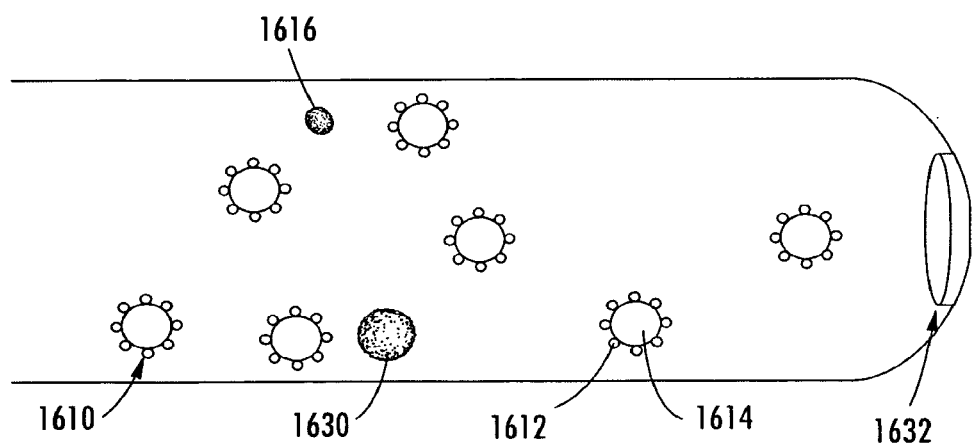
Figure 17:
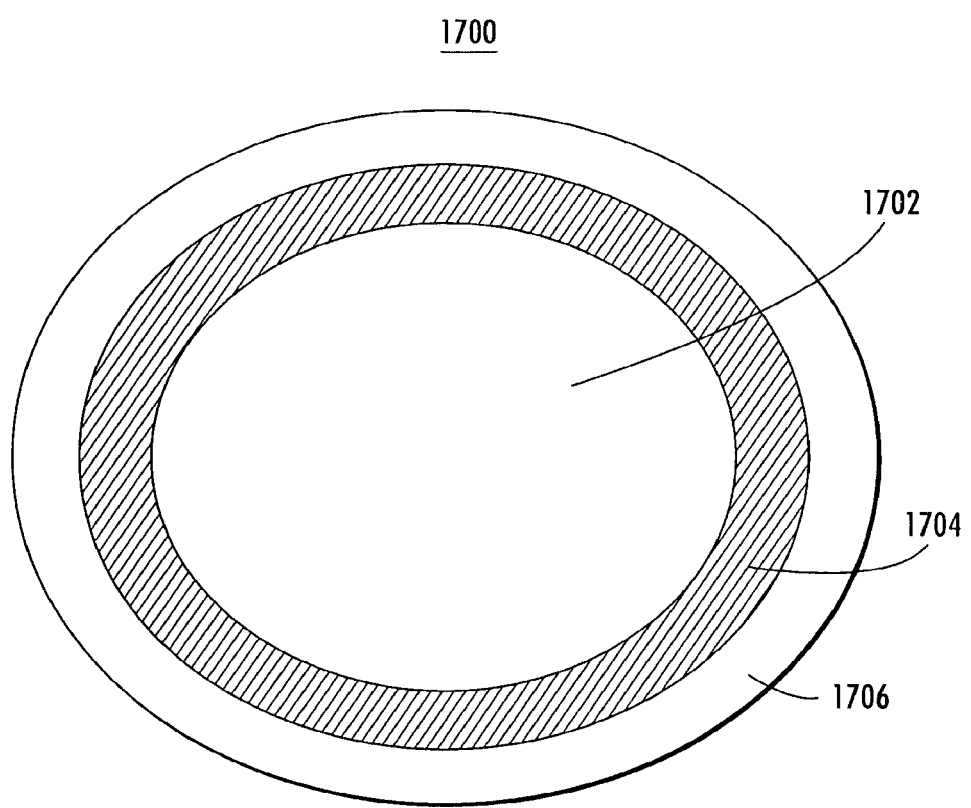
Figure 18A:
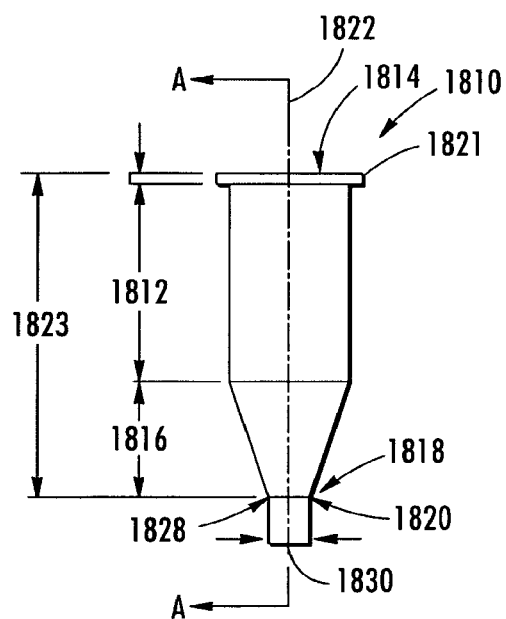
Figure 18B:
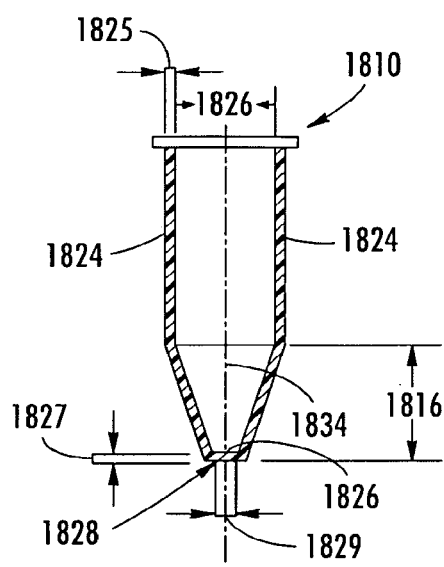
Figure 18C:
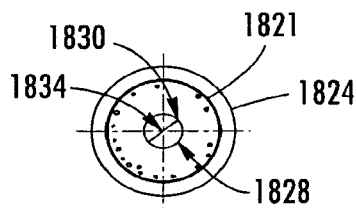
Figure 19A:
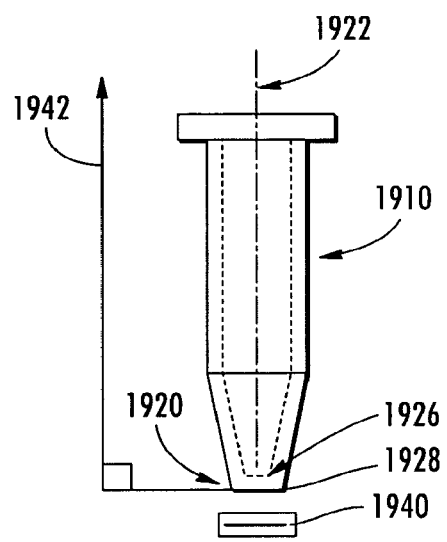
Figure 19B:
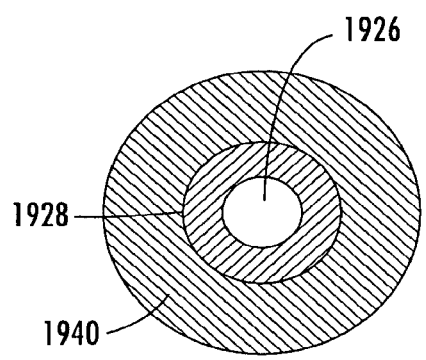
Figure 20:
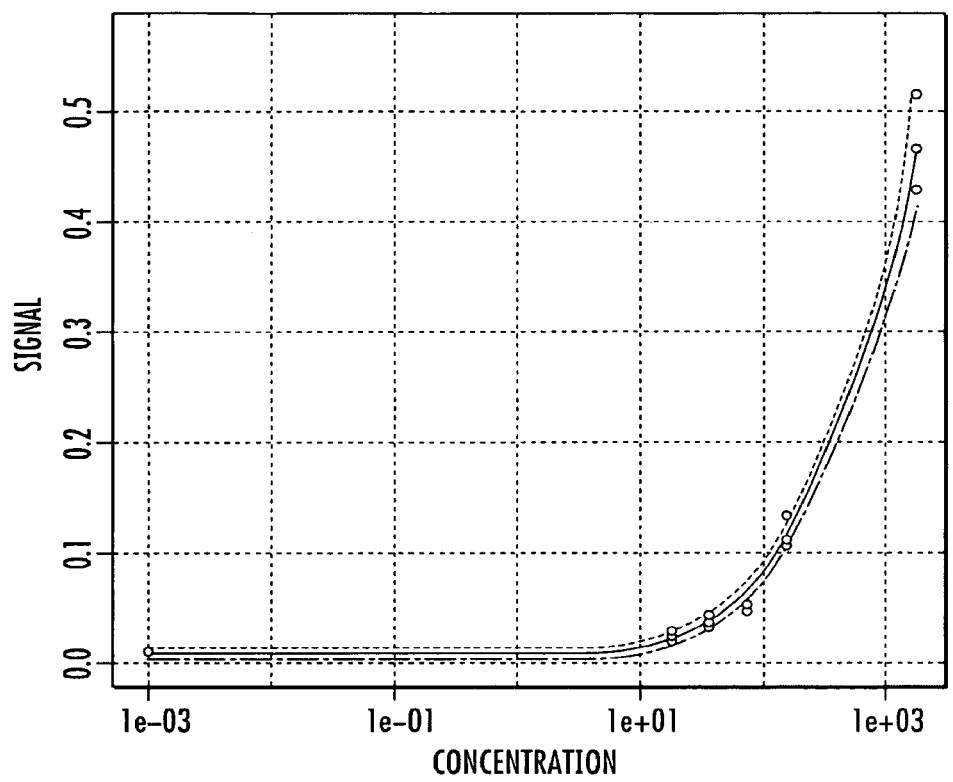

FIG. 13 is a graphical representation of concentration estimates for one of five markers in a multiplexing experiment. Concentration level 20 corresponds to 2.5E8 marker particles/mL. Estimates using pellet-based reference spectra (closed diamonds) show better accuracy and precision, especially at lower concentrations, than solution-based reference spectra (open circles). The straight line shows a 1:1 relation. (Solution-based data points are offset from the pellet-based points on the x-axis for clarity.);

FIG. 14 shows a transmission electron micrograph (TEM) of a satellite structure according to one embodiment of the presently disclosed subject matter;

FIG. 15 illustrates a sandwich assay using a satellite structure for amplifying an analyte signal according to an embodiment of the presently disclosed subject matter;

FIG. 16A depicts a sandwich assay using a satellite structure for amplifying an analyte signal according to an embodiment of the presently disclosed subject matter; and FIG. 16B shows the sandwich assay of FIG. 16A following the application of a magnetic field;

FIG. 17 illustrates a cross-section of a core-shell composite particle according to an embodiment of the presently disclosed subject matter;

FIG. 18A is a drawing showing a side view of a sample tube according to one embodiment of the presently disclosed subject matter;

FIG. 18B is a drawing showing a cross-sectional side view taken along Section A-A of the sample tube shown in FIG. 18A;

FIG. 18C is a drawing showing a bottom view of the sample tube shown in FIG. 18A;

FIG. 19A is a drawing showing a side view of a magnet positioned adjacent and below a sample tube according to one embodiment of the presently disclosed subject matter;

FIG. 19B is a drawing showing a top view of the magnet and sample tube shown in FIG. 19A; and FIG. 20 is a graph illustrating a thyroid-stimulating hormone (TSH) assay binding curve using a sample tube according to one embodiment of the presently disclosed subject matter.

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

I. Assays Using SERS-Active Particles

In some embodiments, the presently disclosed subject matter provides diagnostic assays for determining the presence or amount of an analyte or ligand of interest in a biological sample. Accordingly, in some embodiments, the presently disclosed subject matter provides assay methods, compositions, systems, instruments, and kits for performing diagnostic assays using SERS-active nanoparticles.

As described in more detail herein below, the detection capabilities of the presently disclosed assays are improved in one or more ways over assays known in the art. These improvements include, but are not limited to an increase in signal intensity, enhanced specificity, higher accuracy, improved repeatability, and combinations thereof. The presently disclosed assays also can provide diagnostic results in a shorter period of time than assays known in the art. Such improvements, either alone or in combination, allow for the use of the presently disclosed methods in applications, such as diagnostic assays using Raman spectroscopy as a detection method, optical imaging of tissues, and other applications, where such enhancements are required.

When used in a diagnostic assay, the enhanced characteristics observed for the presently disclosed methods enable detection of biomarkers, including, but not limited to, proteins, polynucleotides, and metabolites, at lower concentrations than those measurable using SERS methods known in the art, and also enable detection of cells (e.g., whole organisms). These enhanced characteristics also are beneficial in applications where the Raman signal has to pass through, i.e., is transmitted through, a complex medium, such as whole blood or serum. Further, diagnostic assays with a enhanced characteristics can be required for early detection of a condition or a disease state in a subject.

A. General Overview: Surface Enhanced Raman Spectroscopy

When a molecule is irradiated with photons of a particular frequency, the photons are scattered. The majority of the incident photons are elastically scattered without a change in frequency (Rayleigh scattering), whereas a small fraction of the incident photons (approximately 1 in every $10^6$) interact with a vibrational mode of the irradiated molecule and are inelastically scattered. The inelastically scattered photons are shifted in frequency and have either a higher frequency (anti-Stokes) or a lower frequency (Stokes). By plotting the frequency of the inelastically scattered photons against their intensity, a unique Raman spectrum of the molecule is observed. The low sensitivity of conventional Raman spectroscopy, however, has limited its use for characterizing biological samples in which the target analyte(s) typically are present in small quantities.

When a Raman-active molecule is adsorbed on or in close proximity to, e.g., within about 50 Å of, a metal surface, the intensity of a Raman signal arising from the Raman-active molecule can be enhanced. For example, increases in the Raman signal by a factor of about $10^3$ to about $10^6$, or in some cases, $10^{14}$ have been reported to date. This enhancement is referred to as the surface-enhanced Raman scattering (SERS) effect. The SERS effect was first reported in 1974 by Fleishman et al., who observed intense Raman scattering from pyridine adsorbed on a roughened silver electrode surface. See Fleishman et al., "Raman spectra of pyridine adsorbed at a silver electrode," *Chem. Phys. Lett.*, 26, 163 (1974); see also Jeanmaire, D. L., and Van Dyne, R. P., "Surface Raman spectroelectrochemistry. 1. Heterocyclic, aromatic, and aliphatic-amines absorbed on anodized silver electrode." *J. Electroanal. Chem.*, 84(1), 1-20 (1977); Albrecht, M. G., and Creighton, J. A., "Anomalously intense Raman spectra of pyridine at a silver electrode," *J.A.C.S.*, 99, 5215-5217 (1977). Since then, SERS has been observed for a number of different molecules adsorbed on the surface of metal surfaces. See, e.g., A. Campion, A. and Kambhampati, P., "Surface-enhanced Raman scattering," *Chem. Soc. Rev.*, 27, 241 (1998).

The magnitude of the SERS enhancement depends on a number of parameters, including the position and orientation of various bonds present in the adsorbed molecule with respect to the electromagnetic field at the metal surface. The mechanism by which SERS occurs is thought to result from a combination of (i) surface plasmon resonances in the metal that enhance the local intensity of the incident light; and (ii) formation and subsequent transitions of charge-transfer complexes between the metal surface and the Raman-active molecule.

The SERS effect can be observed with Raman-active molecules adsorbed on or in close proximity to metal colloidal particles, metal films on dielectric substrates, and metal particle arrays, including metal nanoparticles. For example, Kneipp et al. reported the detection of single molecules of a dye, cresyl violet, adsorbed on aggregated clusters of colloidal silver nanoparticles. See Kneipp, K. et al., "Single molecule detection using surface-enhanced Raman scattering (SERS), *Phys. Rev. Lett.*, 78(9), 1667-1670 (1997). That same year, Nie and Emory observed the surfaced enhanced resonance Raman spectroscopy (SERRS) signal, wherein the resonance between the absorption energy of the Raman-active molecule and that of the nanoparticle yield an enhancement as large as about $10^{10}$ to about $10^{12}$, of a dye molecule adsorbed on a single silver nanoparticle, where the nanoparticles ranged from spherical to rod-like and had a dimension of about 100 nm. See Nie, S., and Emory, S. R., "Probing single molecules and single nanoparticles by surface-enhanced Raman scattering," *Science*, 275, 1102-1106 (1997); Emory, S. R., and Nie, S., "Near-field surface-enhanced Raman spectroscopy on single silver nanoparticles," *Anal. Chem.*, 69, 2631 (1997).

A Raman enhancing particle having associated therewith, e.g., adsorbed on or attached to, a SERS-active molecule(s) is referred to herein as a "SERS-active particle." More particularly, a SERS-active particle, as referred to herein, includes a particle have a surface that induces, causes, or otherwise supports surface-enhanced Raman light scattering (SERS) or surface-enhanced resonance Raman light scattering (SERRS). A number of surfaces are capable of producing a SERS signal, including roughened surfaces, textured surfaces, and other surfaces, including smooth surfaces.

"Raman scattering" generally refers to the inelastic scattering of a photon incident on a molecule. Photons that are inelastically scattered have an optical frequency ($v_i$), which is different than the frequency of the incident light ($v_0$). The difference in energy ($\Delta E$) between the incident light and the inelastically scattered light can be represented as $(\Delta E) = h|v_0 - v_i|$, wherein h is Planck's constant, and corresponds to energies that are absorbed by the molecule. The incident radiation can be of any frequency $v_0$, but typically is monochromatic radiation in the visible or near-infrared spectral region. The absolute difference $|v_0-v_1|$ is an infrared, e.g., vibrational, frequency. More particularly, the process that produces light of frequency other than $v_0$ is referred to as "Raman scattering." The frequency $v_1$ of the "Raman scattered" radiation can be greater than or less than $v_0$, but the amount of light with frequency $v_1<v_0$ (Stokes radiation) is greater than that with frequency $v_1>v_0$ (anti-Stokes radiation).

As used herein, the term "radiation" refers to energy in the form of electromagnetic radiation that can induce surface-enhanced Raman scattering in a sample under test, e.g., a sample comprising a SERS-active nanoparticle having one or more SERS-active reporter molecules associated therewith. More particularly, the term "radiation" refers to energy in the form of electromagnetic radiation that causes the surface of a nanoparticle to induce, emit, support, or otherwise cause light scattering, e.g., Raman scattering, in a reporter molecule proximate to the nanoparticle surface. As used herein, a "reporter molecule" refers to any molecule or chemical compound that is capable of producing a Raman spectrum when it is illuminated with radiation of a proper wavelength. A "reporter molecule" also can be referred herein as a "label," a "dye," a "Raman-active molecule," or "SERS-active molecule," each of which can be used interchangeably.

"Surface-enhanced Raman scattering" or "SERS" refers to the phenomenon that occurs when the Raman scattering signal, or intensity, is enhanced when a Raman-active molecule is adsorbed on or in close proximity to, e.g., within about 50 Å of, a metal surface. "Surface-enhanced resonance Raman scattering" or "SERRS" refers to an increased SERS signal that occurs when the reporter molecule in close proximity to the SERS-active nanoparticle surface is in resonance with the excitation wavelength.

B. Representative Nanoparticles Suitable for use with the Presently Disclosed Methods 1. Nanoparticles Generally Any SERS-active particle is suitable for use in the presently disclosed methods. Such SERS-active particles typically are nanoparticles and also are referred to as "nanotags." As used herein, the terms "nanoparticle," "nanostructure," "nanocrystal," "nanotag," and "nanocomponent," are used interchangeably and refer to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm). In some embodiments, the nanoparticle is a metallic nanoparticle. In some embodiments, the nanoparticle is a spherical particle, or substantially spherical particle having a core diameter between about 2 nm and about 200 nm (including about 2, 5, 10, 20, 50, 60, 70, 80, 90, 100, and 200 nm). In some embodiments, the nanoparticle has a core diameter between about 2 nm and about 100 nm (including about 2, 5, 10, 20, 30, 40, 50, 60, 70, 80, 90, and 100 nm) and in some embodiments, between about 20 nm and 100 nm (including about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nm). One of ordinary skill in the art, upon review of the presently disclosed subject matter, would recognize that a nanoparticle suitable for use with the presently disclosed assays can include a core, e.g., a metal core, which induces the Raman effect, and can further include one or more layers of SERS-active materials, encapsulants, and/or outer shell structures that also can contribute to the size, e.g., total diameter of the nanoparticle structure.

SERS-active nanoparticles suitable for use with the presently disclosed methods typically comprise at least one metal, i.e., at least one element selected from the Periodic Table of the Elements that is commonly known as a metal. Suitable metals include Group 11 metals, such as Cu, Ag, and Au, or any other metals known by those skilled in the art to support SERS, such as alkali metals. In some embodiments, the nanoparticle substantially comprises a single metal element. For example, the preparation of gold nanoparticles is described by Frens, G., *Nat. Phys. Sci.*, 241, 20 (1972). In other embodiments, the nanoparticle comprises a combination of at least two elements, such as an alloy, for example, a binary alloy. In some embodiments, the nanoparticle is magnetic.

In other embodiments, the metal includes an additional component, such as in an $Au_2S/Au$ core-shell particle. $Au_2S/Au$ core-shell particles have been reported to have widely tunable near-IR optical resonance. See Averitt, R. D., et al., "Ultrafast optical properties of gold nanoshells," *JOSA B*, 16(10), 1824-1832 (1999). Further, Ag core/Au shell particles, such as those described by Cao, Y. W., et al., "DNA-modified core-shell Ag/Au nanoparticles," *J. Am. Chem. Soc.*, 123(32), 7961-7962 (2001), or Au core/Ag shell particles, or any core-shell combination involving SERS-active metals, can be used. Other combinations suitable for use in core-shell particles also are suitable for use with the presently disclosed methods, including Au- or Ag-functionalized silica/alumina colloids, Au- or Ag-functionalized $TiO_2$ colloids, Au nanoparticle capped-Au nanoparticles (see, e.g., Mucic, et al., "DNA-directed synthesis of binary nanoparticle network materials," *J. Am. Chem. Soc.*, 120 (48), 12674 (1998)); Au nanoparticle-capped $TiO_2$ colloids; and particles having a Si core with a metal shell (i.e., "nanoshells"), such as silver-capped $SiO_2$ colloids or gold-capped $SiO_2$ colloids. See, e.g., Jackson, et al., *Proc. Natl. Acad. Sci. U.S.A.* 101(52):17930-5 (2004); see also U.S. Pat. Nos. 6,344,272 and 6,685,986 to Oldenburg et al., each of which is incorporated herein by reference in its entirety. The use of such nanoshells in biosensing applications has been described. See U.S. Pat. No. 6,699,724 to West et al., which is incorporated herein by reference in its entirety.

Another class of nanoparticles suitable for use with the presently disclosed methods includes nanoparticles having an internal surface. Such nanoparticles include hollow particles and hollow nanocrystals or porous or semi-porous nanoparticles. See, e.g., U.S. Pat. No. 6,913,825 to Ostafin et al., which is incorporated herein by reference in its entirety. Accordingly, the presently disclosed subject matter also provides a nanoparticle comprising a core-shell particle active for SERS or a hollow nanoparticle active for SERS. In some embodiments, such nanoparticles can exhibit an improved SERS signal.

While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle. Accordingly, nanoparticles suitable for use with the presently disclosed methods can have a variety of shapes, sizes, and compositions. Further, the nanoparticle can be solid, or in some embodiments, as described immediately hereinabove, hollow. Non-limiting examples of suitable nanoparticles include colloidal metal hollow or filled nanobars, magnetic, paramagnetic, conductive or insulating nanoparticles, synthetic particles, hydrogels (colloids or bars), and the like. It will be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

Further, nanoparticles suitable for use with the presently disclosed methods can be isotropic or anisotropic. As referred to herein, anisotropic nanoparticles have a length and a width. In some embodiments, the length of an anisotropic nanoparticle is the dimension parallel to the aperture in which the nanoparticle was produced. In some embodiments, the anisotropic nanoparticle has a diameter (width) of about 350 nm or less. In other embodiments, the anisotropic nanoparticle has a diameter (width) of about 250 nm or less and in some embodiments, a diameter (width) of about 100 nm or less. In some embodiments, the width of the anisotropic nanoparticle is between about 15 nm to about 300 nm. Further, in some embodiments, the anisotropic nanoparticle has a length, wherein the length is between about 10 nm and 350 nm.

Much of the SERS literature (both experimental and theoretical) suggests that anisotropic particles (rods, triangles, prisms) can provide an increased enhancement of the Raman signal as compared to spheres. For example, the so-called "antenna effect" predicts that Raman enhancement is expected to be larger at areas of higher curvature. Many reports of anisotropic particles have been recently described, including silver (Ag) prisms and "branched" gold (Au) particles.

Anisotropic Au and Ag nanorods can be produced by electrodeposition into preformed alumina templates, in a manner similar to the production of Nanobarcodes® particles. See, e.g., Nicewarner-Pena, S. R., et al., "Submicrometer metallic barcodes," *Science,* 294, 137-141 (2001); Walton, I. D., et al., "Particles for multiplexed analysis in solution: detection and identification of striped metallic particles using optical microscopy," *Anal. Chem.* 74, 2240-2247 (2002). These particles can be prepared by the deposition of alternating layers of materials, typically Au and Ag, into preformed alumina templates, and can have a diameter of about 250 nm and a length of about 6 microns.

2. Encapsulated SERS-Active Nanoparticles

SERS-active metal nanoparticles have a tendency to aggregate in aqueous solution and once aggregated are difficult to re-disperse. Further, the chemical composition of some Raman-active molecules is incompatible with chemistries used to attach other molecules, such as proteins, to metal nanoparticles. These characteristics can limit the choice of Raman-active molecule, attachment chemistries, and other molecules to be attached to the metal nanoparticle.

Accordingly, in some embodiments, a SERS-active reporter molecule when affixed, e.g., either adsorbed or covalently attached to a nanoparticle, can be coated or encapsulated, for example, in a shell, of a different material, including a polymer, glass, or ceramic material. Such embodiments are referred to herein as "encapsulated SERS-active nanoparticles." Methods for preparing encapsulated SERS-active nanoparticles are described in U.S. Pat. No. 6,514,767 to Natan, which is incorporated herein by reference in its entirety.

Examples of suitable particles for use with the presently disclosed methods include Oxonica Nanotags (Oxonica Inc., Mountain View, Calif.). In one embodiment, the nanotags comprise a gold core having a diameter of about 50 nm, are coated with a distinct reporter molecule, and are encapsulated, in some embodiments, in a 10 nm to 50 nm protective glass coating, in some embodiments, a 15 nm to 40 nm protective glass coating, in some embodiments, a 30 nm to 40 nm protective glass coating, and, in some embodiments, a 35 nm protective glass coating, as described hereinabove. Nanotags are further described, for example, in U.S. Pat. No. 6,514,767 to Natan; U.S. Published Patent Application Nos. 2003/0166297 to Natan and 2005/0158870 A1 to Natan, the disclosures of which are hereby incorporated by reference.

The presently disclosed encapsulated SERS-active nanoparticles can include a metal nanoparticle, a submonolayer, monolayer, or multilayer of one or more reporter molecules in close proximity to the surface of the metal nanoparticle. The term "in close proximity" is intended to mean within about 50 nm or less of an outer surface of the nanoparticle. A nanoparticle having a submonolayer, monolayer, or multilayer of one or more reporter molecules attached to an outer surface of the nanoparticle core also can include an encapsulating shell. In such embodiments, the reporter molecule is positioned at an interface between the outer surface of the metal nanoparticle and an interior surface of the encapsulating shell.

The nanoparticle core comprising the encapsulated nanoparticle can be a metal sphere, e.g., a gold, silver, or copper sphere, having a diameter of about 20 nm to about 200 nm. In some embodiments, the nanoparticle core comprises an oblate or prolate metal spheroid. The diameter of the nanoparticle core can be selected based, in part, on the wavelength of incident light. In some embodiments, the encapsulating shell comprises a dielectric material, such as a polymer, glass, metal, metal oxides, such as $TiO_2$ and $SnO_2$, metal sulfides or a ceramic material. In some embodiments, the encapsulant is glass, e.g., $SiO_x$. To encapsulate the presently disclosed SERS-active nanoparticles in glass, the metal nanoparticle cores can be treated with a glass primer, i.e., a material that can lead to a growth of a uniform coating of glass, or can improve adhesion of the glass coat to the particle, or both. Glass can then be grown over the metal nanoparticle by standard techniques known in the art.

The encapsulation process can be carried out after, or during, attaching or adsorbing one or more reporter molecules to the core nanoparticle. In this way, the dye is sequestered from the surrounding solvent as a coating on the surface of the metal nanoparticle core. Such a configuration provides the metal nanoparticle core with a stable SERS activity. The dye can form a sub-monolayer, a complete monolayer, or a multilayer assembly on the surface of the metal nanoparticle core. The dye layer can comprise a single dye or can be a mixture of different dyes.

Thus, in some embodiments, a SERS-active reporter molecule forms a layer on the outer surface of the nanoparticle core, wherein the layer at least partially covers the outer surface of the nanoparticle core and is defined by an inner surface and an outer surface. The encapsulant is disposed on at least one of the outer surface of the nanoparticle core and the outer surface of the layer of the SERS-active reporter molecule to at least partially surround the nanoparticle core, which is at least partially covered with a layer of the SERS-active reporter molecule.

Further, in some embodiments, the encapsulant can be modified, e.g., derivatized by standard techniques known in the art, to attach molecules, including biomolecules, to its outer surface. This characteristic allows the presently disclosed encapsulated SERS-active nanoparticles to be conjugated to molecules, including biomolecules, such as proteins and nucleic acids, or to solid supports without interfering with the Raman activity of the dye. Glass and other materials suitable for use as an encapsulating shell contain functional groups amenable to molecular attachment. For example, immersion of glass in a suitable base allows for the covalent attachment of alkyl trichlorosilanes or alkyl trialkoxysilanes, with additional functionality available on the end of the alkyl group of the alkyl trichlorosilane or alkyl trialkoxysilane group. In some embodiments, one or more of an aminoalkyltrialkyloxysilane group, a mercaptoalkyltrialkoxysilane group, or a carboxyalkyltrialkoxysilane group can be covalently attached to the glass surface. Thus, glass surfaces can be modified with many forms of biomolecules and biomolecular superstructures, including cells, as well as oxides, metals, polymers, and the like. Likewise, surfaces of glass can be modified with well-organized monomolecular layers. Accordingly, glass coatings support many types of chemical functionalization (also referred to herein as "derivatization"). Other forms of encapsulants also can be functionalized, as well. Accordingly, the presently disclosed nanoparticles can be affixed to any species known in the art having a chemically-reactive functionality.

The thickness of the encapsulant can be varied depending on the physical properties required of the SERS-active nanoparticle. The physical properties, such as the sedimentation coefficient can be affected by the thickness of the encapsulant. In general, the thicker the encapsulant, the more effective the sequestration of the SERS-active dyes on the metal nanoparticle core from the surrounding solvent.

In embodiments wherein the encapsulant is glass, the thickness of the glass typically can range from about 1 nm to about 50 nm. In exemplary, non-limiting embodiments, the encapsulated SERS-active nanoparticles comprise gold nanoparticles having a diameter ranging from about 50 nm to about 100 nm encapsulated in a sphere of glass having a thickness ranging from about, in some embodiments, from about 10 nm to about 50 nm; in some embodiments, from about 15 nm to about 40 nm; and, in some embodiments, about 35 nm. The optimization of the dimensions of the presently disclosed encapsulated SERS-active nanoparticles can be accomplished by one of ordinary skill in the art. For example, it is known in the art that core-shell nanoparticles (e.g., Au/AuS nanoparticles) support SERS and have different optical properties as compared to pure metal nanoparticles. Likewise, it is known in the art that SERS from prolate spheroids can be enhanced relative to spheres with the same major axis. Further, it is known that single particle enhancements are wavelength-dependent. Thus, the particle size can be "tuned" to achieve a maximum SERS signal for a given excitation wavelength. Accordingly, the composition of the particle, or its size or shape can be altered in accordance with the presently disclosed subject matter to optimize the intensity of the SERS signal.

The presently disclosed encapsulated SERS-active nanoparticles are easy to handle and store. Further, they also are aggregation resistant, stabilized against decomposition of the dye in solvents and air, are chemically inert, and can be concentrated, e.g., by magnetic pull down techniques, and redispersed without loss of SERS activity.

As described in more detail herein below, the presently disclosed subject matter also provides more specialized nanoparticles capable of enhancing an assay using SERS-active particles.

3. Reporter Molecules

The reporter molecules can be any molecule that provides a Raman signal upon exposure to appropriate irradiation. A "reporter molecule" refers to any molecule or chemical compound that is capable of producing a Raman signal. A "reporter molecule" also can be referred herein as a "label," a "dye," a "Raman-active molecule," or "SERS-active molecule," each of which can be used interchangeably. A number of distinct reporter molecules with strong Raman spectra are known and can be used to create distinct "flavors" of SERS-active particles to enable multiplexing capabilities (the term "flavors" indicates particles that provide distinct Raman signatures upon irradiation). Such particles typically are able to function in the near-infrared (NIR) wavelength region, are detectable in whole blood, and are photostable. Further, a number of different "flavors" can be excited with a single wavelength.

C. Representative Capture Probes

Capture probes, such as antibodies or DNA probes, can be immobilized onto the protective glass coating using known bioconjugation techniques. An advantage of this approach is that the SERS signal-generating reporter molecule is secured in close proximity to the gold surface and protected by the glass coating from biological or chemical attack. In addition, competitive binding between the reporter molecule and the capture probe is eliminated, allowing for maximum surface coverage of the reporter molecule on the nanoparticle core surface and the capture probe on the glass surface, respectively.

More generally, SERS-active nanoparticles can be functionalized with a molecule, such as a specific binding member of a binding pair, which can bind to a target analyte. The binding event creates a detectable signal, which is indicative of the presence and/or amount of an analyte. The detectable signal can correspond to a localized detection of a SERS tag or can be represented by a detectable wavelength shift in the SERS spectrum.

The use of a functionalized SERS-active nanoparticle has several advantages over non-functionalized nanoparticles. First, the functional group provides a degree of specificity to the nanoparticle by providing a specific interaction with a target analyte. Second, the target analyte does not have to be Raman active itself; its presence can be determined by measuring the SERS spectrum of the Raman-active dye attached to the nanoparticle. Such measurements are referred to herein as "indirect detection," in which the presence or absence of a target analyte or ligand in a biological sample is determined by detecting a SERS signal that does not directly emanate from the target analyte or ligand of interest.

SERS-active nanoparticles suitable for use with the presently disclosed methods can be functionalized to bind to a target analyte in at least two different ways. In some embodiments, the SERS-active reporter molecule, i.e., a SERS-active dye, can be conjugated with a specific binding member of a binding pair, whereas in other embodiments, a specific binding member of a binding pair can be attached directly to the nanoparticle. In embodiments in which the nanoparticle core is at least partially surrounded by an encapsulating shell, the binding member can be attached to an outer surface of the encapsulating shell.

As used herein, the term "conjugate" refers to a molecule comprising two or more subunits bound together, optionally through a linking group, to form a single molecular structure. The binding can be made either by a direct chemical bond between the subunits or through a linking group. Such binding in a conjugate typically is irreversible. As used herein, the term "affinity" refers to the strength of the attraction between one binding member to another member of a binding pair at a particular binding site. The term "specificity" and derivations thereof, refer to the likelihood that a binding member will bind to another member of a binding pair. Such binding between one binding member, e.g., a binding protein, to another binding member of a binding pair, e.g., a ligand or analyte, can be reversible.

The term "specific binding member" refers to a molecule for which there exists at least one separate, complementary binding molecule. A specific binding member is a molecule that binds, attaches, or otherwise associates with a specific molecule. The binding, attachment, or association can be chemical or physical. A specific molecule to which a specific binding member binds can be any of a variety of molecules, including, but not limited to, antigens, haptens, proteins, carbohydrates, nucleotide sequences, nucleic acids, amino acids, peptides, enzymes, and the like. Further, a specific binding member of a particular type will bind a particular type of molecule. In such instances, the specific binding members are referred to as a "specific binding pair." Accordingly, an antibody will specifically bind an antigen. Other specific binding pairs include avidin and biotin, carbohydrates and lectins, complementary nucleotide sequences, complementary peptide sequences, enzymes and enzyme cofactors, and the like.

1. SERS-Active Nanoparticles Having a Specific Binding Member of a Binding Pair Attached Directly Thereto In some embodiments, a binding member of a specific binding pair, for example, an antibody, such as a monoclonal antibody, can be attached directly to the surface of the nanoparticle. In an exemplary embodiment, a specific binding member of a binding pair, e.g., a monoclonal antibody, can be treated with linker, e.g., polyethylene glycol (PEG), and attached directly to the nanoparticle through the PEG linker.

As would be appreciated by one of ordinary skill in the art, the selection of the linker can be determined by various factors depending on the objects of the assay. For example, the use of PEG as a linker can stabilize the orientation of the antibody such that the epitope of the antigen is pointed away from the surface of the nanoparticle. In this way, the functionalized nanoparticle can be designed to maximize the presentation of the epitope or other binding region to the test solution, thereby potentially increasing the sensitivity of the assay.

Depending on the binding member, other linkers can be used. For example, alkanethiols can be used as linkers for antibodies and peptides. Short chain alkanethiols, including, but not limited to, N-succinimidyl-S-acetylthioacetate (SATA) and N-succinimidyl-S-acetylthiopropionate (SATP) can be used as linkers after sulfhydryl deprotection. Other properties also can determine the choice of linker, such as the length of the linker chain. For example, PEG can be desirable in that it also acts to protect the surface of the reagent and is flexible, which can enhance the ability of the reagent to bind to the analyte of interest.

A specific binding member, such as an antibody, also can be modified with a linker, such as a thiolated PEG linker, and attached to the nanoparticle.

2. Representative Binding Members

In some embodiments, the binding member conjugated with the presently disclosed SERS-active nanoparticle, either through the SERS-active reporter molecule or directly attached to an outer surface of the nanoparticle itself, comprises a polypeptide or protein, such as a glucose binding protein. Representative binding members include, but are not limited to, specific binding members having an affinity for a target analyte, including nucleic acids, protein domains, antibody fragments, cells, and antibodies for target analytes, such as prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen. Antibodies for such target analytes are known in the art.

The analyte and binding member can act as binding partners. The term "associates" or "binds" as used herein refers to binding partners having a relative binding constant (Kd) sufficiently strong to allow detection of binding to the protein by a detection means. The Kd can be calculated as the concentration of free analyte at which half the protein is bound, or vice versa. When the analyte of interest is glucose, the Kd values for the binding partners are between about 0.0001 mM and about 50 mM.

D. Diagnostic Assays Generally

SERS-active nanoparticles can be used in diagnostic assays. For example, Rohr et al. demonstrated an immunoassay with SERS detection including multiple components and washing steps. See Rohr, T. E., et al., "Immunoassay employing surface-enhanced Raman spectroscopy," *Anal. Biochem.*, 182:388 (1989). Also, Ni et al. demonstrated reporter attachment to a gold slide in a heterogeneous detection assay including incubation and washing steps. See Ni, J., et al., "Immunoassay Readout Method Using Extrinsic Raman Labels Adsorbed on Immunogold Colloids," *Anal. Chem.*, 71:4903 (1999). The SERS assays disclosed by Rohr et al. and Ni et al., as well as others known in the art, require lengthy incubations and wash steps.

Another example of an assay using SERS is disclosed in U.S. Pat. No. 5,266,498 to Tarcha et al., which is incorporated herein by reference in its entirety. Tarcha et al. discloses the use of a multiple reagent system in which a label or antibody is attached to a SERS surface. A second reagent contains the complementary pair of either label or antibody.

In some embodiments, the presently disclosed SERS-active nanoparticles can be used as optical tags in biological assays. In some embodiments, a target molecule, e.g., an antigen, to be detected is captured by a first binding partner attached to a solid surface. A second binding partner, also specific to the target molecule, can be attached to a SERS-active nanoparticle. When an analyte is present, both the first and second binding partners will bind the target, thus forming a sandwich of SERS-active nanoparticle-target-solid surface. The solid surface can be, e.g., an immovable substrate or a movable particle.

E. Liquid-Based Assays

Liquid-based assay approaches using SERS-active nanoparticles have been previously disclosed. See, e.g., Hirsch et al., "A Whole Blood Immunoassay Using Gold Nanoshells," *Anal. Chem.*, 75 (10), 2377-2381 (2003), which is incorporated herein by reference in its entirety. Hirsch et al. discloses the optical detection of particle aggregation in the presence of an analyte of interest by measuring optical absorption changes due to particle interactions. The aggregation of the nanoparticles in the assay disclosed by Hirsch et al. detects the plasmon resonance decrease that occurs as a result of the aggregation of particles. Hirsch et al., however, does not disclose the use of Raman signals for detection.

In one embodiment of the presently disclosed assays, SERS-active particles can be used in a so-called "no-wash" or "homogeneous" assay. In such an assay, a sample is collected into a container, e.g., a specimen collection container, an assay vessel, or other sample container suitable for use with the presently disclosed assays, and the assay is performed without the need to remove sample from the container, e.g., an assay vessel. Advantageously, the sample can be collected into a container that can already contain all reagents necessary to perform the assay. In some embodiments, however, one or more reagents can be added to the container following specimen collection. Representative containers suitable for use with the presently disclosed assays are described in further detail in Section III herein below.

In other embodiments, the presently disclosed SERS-active nanoparticles can be used in heterogeneous assays. As used herein, the term "heterogeneous assay" generally refers to an assay in which one or more components of the assay are added or removed from the assay sequentially. More particularly, a heterogeneous assay can rely, in part, on the transfer of analyte from a liquid sample to a solid phase by the binding of the analyte during the assay to the surface of the solid phase. At some stage of the assay, whose sequence varies depending on the assay protocol, the solid phase and the liquid phase are separated and the determination leading to detection and/or quantitation of the analyte is performed on one of the two separated phases. Thus, a heterogeneous assay, for example, can include a solid support coated with an antigen or antibody that binds an analyte of interest and thereby separates or removes the analyte from other components in the sample under test. These other components can be selectively removed from the sample by one or more washing steps and the analyte remains bound to the solid support, where it is detected, or can be removed by an additional washing step and subsequently detected.

In liquid-based assays, the sample typically is incubated, e.g., at ambient conditions, but it also is possible to provide controlled conditions, such as a specific temperature or rocking of the sample. Following the incubation period, the container can then placed into a reader to obtain a signal from one or more SERS-active particles that were preloaded or subsequently added into the container. A Raman signal is produced, and detected, upon interrogation by incident radiation of a particular wavelength, e.g., laser radiation.

1. Surface-Immobilized Target Analyte(s) of Interest

In some embodiments of liquid-based assays, the target analyte(s) of interest is immobilized, for example, on a localized area of a solid support, such as a functionalized inner surface of a container, e.g., a specimen collection container or assay vessel. The immobilized target analyte(s) of interest can then contacted with a detection reagent comprising SERS-active nanoparticles conjugated with a specific binding member, e.g., an antibody, having an affinity for the target analyte(s) of interest. The SERS-active nanoparticles can interact or associate with, e.g., be reversibly or irreversibly bound to, the immobilized target analyte(s) of interest. Following a suitable incubation time, this interaction between the SERS-active nanoparticle and the immobilized target analyte(s) can be detected by illuminating the localized area of the solid support with incident radiation of the appropriate wavelength and measuring the SERS signal emitted by the SERS-active reporter molecule. Further, because each type of SERS-active reporter molecule exhibits a unique SERS spectrum, a single SERS spectrum can be used to detect a plurality of target analytes of interest by including SERS-active nanoparticles comprising different SERS-active reporter molecules in the detection reagent. Accordingly, the presently disclosed SERS-active nanoparticles can be used in multiplexed assay formats.

2. Reporter Selection and Usage

Reporter molecules preferably exhibit relatively simple Raman spectra with narrow line widths. This characteristic allows for the detection of several different Raman-active species in the same sample volume. Accordingly, this feature allows multiple SERS-active nanoparticles, each including different dyes, to be fabricated such that the Raman spectrum of each dye can be distinguished in a mixture of different types of nanoparticles. This feature allows for the multiplex detection of several different target species in a small sample volume. Thus, nanoparticles having the reporter molecules associated with or attached thereto also are suitable for use in multiplexed chemical assays, in which the identity of the SERS-active nanoparticle encodes the identity of the target of the assay.

Such reporter molecules, when associated with or attached to SERS-active nanoparticles, provide spectral diversity and resolvability in multiplex assays. Each SERS-active nanoparticle, when coupled to a target-specific reagent, can encode the identity of that particular target molecule. Further, the intensity of a particular Raman signal can reveal the quantity of that particular target molecule. Accordingly, SERS-active nanoparticles can be used in multiplexed assays to yield qualitative and/or quantitative information regarding a target molecule without requiring position-sensitive localization of reagents.

A detection reagent can include more than one type of label, e.g., more than one type of SERS-active reporter molecule, depending on the requirements of the assay. For example, different types of SERS-active reporter molecules can exhibit a Raman signal, i.e., a Raman spectrum or Raman spectral feature, at different wavelengths and can be used to create a unique Raman "fingerprint" for a specific analyte of interest, thereby enhancing the specificity of the assay. Different reporter molecules can be attached to different specific binding members to provide a reagent capable of detecting more than one analyte of interest, e.g., a plurality of analytes of interest. Further, multiple reporter molecules can be used to create an internal reference signal that can be used to distinguish background noise from signal detection, particularly in samples that exhibit or are expected to exhibit a relatively weak signal. Additionally, more than one SERS-reporter molecule can be used to avoid or overcome non-specific radiation emitted from the sample solution under test, i.e., radiation emitted from the sample solution that cannot be attributed to direct or indirect measurement of an analyte of interest.

F. Magnetic Capture in Liquid-Based Assays

In some embodiments of liquid-based assays, a magnetic capture reagent can be used to facilitate localization of the particles in the assay vessel. In such embodiments, magnetic capture particles can be labeled with a binding member that has an affinity for one or more analytes of interest. Such magnetic capture particles can bind to one or more analytes of interest, which also can be bound to a SERS-active nanoparticle, to form a magnetic capture particle-analyte-SERS-active nanoparticle complex. The magnetic properties of the magnetic capture particles can be used to localize the magnetic capture particle-analyte-SERS-active nanoparticle in a predetermined area within the assay vessel for detecting the SERS signal.

Accordingly, in some embodiments, the magnetic capture particle-analyte-SERS-active nanoparticle complex is localized at a predetermined area within the assay vessel, for example, a specimen collection container or tube. Radiation can then be directed at the localization area and the SERS signal can be detected. The localization of the magnetic capture particle-analyte-SERS-active nanoparticle complex can increase the reporter molecule-surface interaction and increase the signal by concentrating the SERS effect to a particular area of the assay vessel.

Magnetic capture of the particles can be accomplished using any method known in the art, including, but not limited to, placing a strong magnet or inducing a magnetic field at a localized area of the assay vessel. The magnetic field can be induced, for example, by one or more permanent magnets or electromagnets.

More particularly, in some embodiments, the presently disclosed SERS-active nanoparticles, conjugated with a specific binding member having an affinity for the target analyte(s) of interest can be disposed in a container, e.g., a specimen collection container, either prior to, concurrent with, or subsequent to disposing therein a biological sample suspected of containing one or more target analytes of interest. Magnetic particles, also conjugated with a specific binding member having an affinity for the target analyte(s) of interest, can be disposed in the container. Target analyte(s) of interest present in the sample can bind to the SERS-active nanoparticles and the magnetic particles, thereby forming a complex, e.g., a magnetic capture particle-analyte-SERS-active nanoparticle complex, wherein the target analyte(s) is sandwiched between the SERS-active nanoparticle and the magnetic particle. See, e.g., FIG. 1, which shows a representative magnetic capture assay suitable for use with the presently disclosed subject matter.

Referring now to FIG. 1, a schematic diagram of a representative magnetic capture assay for detecting the presence of one or more analytes in a biological sample is shown. The presently disclosed magnetic capture assay includes one or more magnetic capture particles 100, which have associated therewith at least one specific binding member 110a having an affinity for one or more analytes 130 of interest in a biological sample. The assay also includes one or more SERS-active nanoparticles 120, which have associated therewith at least one binding member 110b having an affinity for the one or more analytes 130. Binding member 110b associated with SERS-active nanoparticle 120 can be the same or different than binding member 110a associated with magnetic capture particles 100. Magnetic particle 100 and SERS-active nanoparticle 120 are contacted with a biological sample comprising one or more analytes 130 of interest and incubated for a period of time to form magnetic capture particle-analyte-SERS-active nanoparticle complex 140, e.g, an antibody-antigen "sandwich" structure, if the one or more analytes 130 are present in the biological sample. Magnetic capture particle-analyte-SERS-active nanoparticle complex 140 is exposed to a magnetic field (not shown) to induce complex 140 to migrate to a localized area of container 150, e.g., an assay vessel or specimen collection container, to form pellet 160. Pellet 160 is illuminated with incident radiation at one or more wavelengths, for example, in a system as shown in FIG. 4, to induce the SERS-active reporter molecule to produce a detectable signal to detect the presence or amount of the one or more analytes in the biological sample. One of ordinary skill in the art upon review of the presently disclosed subject matter would recognize that magnetic capture particle 100, SERS-active nanoparticle 120, and combinations thereof, can be included in container 150 before the sample is disposed therein, or can be added to container 150 prior to, concurrent with, or subsequent to disposing the sample therein;

Accordingly, in some embodiments, magnetic particle enrichment can be used advantageously in the presently disclosed assays. In one such approach, SERS-active particles having one or more capture probes for the analyte(s) of interest attached thereto can be present in a container, e.g., a specimen collection container, prior to sample collection, or, in some embodiments, added after collection. During the incubation phase, target analytes are bound onto the SERS-active particle surface by the capture probes. Magnetic particles, also having attached thereto capture probes to the target(s) of interest, that have been provided in the container can attach to different epitopes on the same target(s), e.g., one or more analytes of interest, and thus form complexes where the target analyte is sandwiched between a SERS-active nanoparticle and a magnetic particle. A magnet can then be used to concentrate these sandwiches in a specified space, i.e., to form a pellet, in the container. The magnet can either be applied before the container is placed into the reader or can be integrated into the reader. Incident radiation of a desired wavelength, e.g., a laser beam, can then be focused on the pellet of concentrated SERS-active nanoparticle-target-magnetic particle sandwich complexes and the SERS signal is obtained from the SERS-active nanoparticles.

As also disclosed in more detail herein, the magnetic capture embodiments of the presently disclosed assays also can include contacting multiple types of SERS-active nanoparticles with the sample, wherein each type of SERS-active nanoparticle has attached thereto a SERS-active reporter molecule that exhibits a unique Raman signal. Such embodiments can be used to detect a plurality of analytes of interest, referred to herein as multiplexing.

G. Referencing and Controls in the Magnetic Pull-Down Liquid-Based Assay

In conventional immunoassays, detection of an antigen can occur by "sandwiching" the antigen between two antibodies, one of which is labeled with an optical, colorimetric, or radiometric reporter. The measured signal, e.g., an optical, colorimetric, or radiometric reporter can then be used to determine the concentration of the antigen present in the sample. Conventional enzyme-linked immunosorbent assay (ELISA) immunoassays are examples of this type of technology. One issue with this technical approach, is that the magnitude of the optical signal depends on several factors in addition to the presence and/or amount of the antigen. For example, the alignment and performance of the optics can impact the measured signal. Typically, to avoid this problem, additional control samples having known concentrations of antigen are measured.

In one embodiment of the presently disclosed subject matter, as noted above, a measurable signal is generated by forming an antigen-mediated complex between a SERS-labeled nanotag and a magnetic capture particle. The complexes can be separated from the solution by application of a magnetic field and the optical signal from the resulting magnetic pellet is measured.

The position of the magnetic pellet relative to the interrogating optics can affect the magnitude of the measured optical signal and ultimately, the calibration of the assay. In addition, the shape of the magnetic pellet might not always be consistent. For example, altering the surface functionality of the magnetic particles could change the density and/or shape of the pellet.

According to embodiments of the presently disclosed subject matter, it is possible to compensate for variations in pellet size, shape, or positioning. These methods also are applicable to other assay formats in which a pellet is formed. In one embodiment, magnetic particles used for the magnetic pull-down are labeled with a reference label in addition to the capture probes, e.g., antibodies specific to the antigen of interest. The reference label can be any moiety capable of generating (by itself or upon some type of stimulation) a detectable signal, including, but not limited to fluorophores, organic dyes, rare earth elements, and Raman reporters, and also could include particles comprising such components. Specific examples of reference labels include SERS-active particles of the type disclosed herein and silica particles having fluorophores distributed on or throughout the silica particles.

An example of incorporation of a reference label into an assay is illustrated in FIG. 2. The presently disclosed magnetic capture assay incorporating a reference label includes one or more magnetic capture particles 200, which have associated therewith at least one specific binding member 210a having an affinity for one or more analytes 240 of interest in a biological sample. In this embodiment, the one or more magnetic capture particles 200 also have associated therewith at least one reference label 230 capable of generating a detectable signal. In some embodiments, reference label 230 comprises a second SERS-active nanoparticle having a different reporter molecule than the one or more SERS-active nanoparticles 220 which form complex 250 with the one or more analytes 240.

The assay also includes one or more SERS-active nanoparticles 220, which have associated therewith at least one binding member 210b having an affinity for the one or more analytes 240. Binding member 210b associated with SERS-active nanoparticle 220 can be the same or different than binding member 210a associated with magnetic capture particles 200.

As with the assay depicted in FIG. 1, magnetic particle 200 and SERS-active nanoparticle 220 are contacted with a biological sample comprising one or more analytes 240 of interest and incubated for a period of time to form magnetic capture particle-analyte-SERS-active nanoparticle complex 250 if the one or more analytes 240 are present in the biological sample. Magnetic capture particle-analyte-SERS-active nanoparticle complex 250 is exposed to a magnetic field (not shown) to induce complex 250 to migrate to a localized area of a container, e.g., an assay vessel or specimen collection container, to form pellet as shown previously in FIG. 1.

All magnetic particles present in the container (whether complexed or not) are pulled down into the localized area of the container, e.g., an optical read area. The pellet comprising magnetic capture particle-analyte-SERS-active nanoparticle complex 250 is illuminated with incident radiation at one or more wavelengths, for example, in a system as shown in FIG. 4, to induce SERS-active nanoparticle 220 to produce a first detectable signal and reference label 230 to produce a second detectable signal. The first detectable signal of SERS-active nanoparticle 220 can be compared to the second detectable signal of reference label 230 to detect the presence or amount of one or more analytes 240 in the biological sample.

The Raman signal from particle 220 is related to the amount of analyte 240, e.g., an antigen, present; whereas the signal from reference label 230, e.g., a nanoparticle having a different SERS-reporter molecule than particle 220, acts as a reference and corrects for variations in pellet shape, density, and/or position. Thus, calibration can be based on a comparing the intensity of Reporter 1, e.g., particle 220, to the intensity of Reporter 2, e.g., reference label 230. For example, the signal can be calculated by as (Reporter 1 intensity)/(Reporter 2 intensity), in other words, the ratio of the intensity of Reporter 1 relative to the intensity of Reporter 2.

Although FIG. 2 shows one SERS-active particle per magnetic capture particle, multiple reference labels/particles per magnetic particle are possible or, alternatively, a fraction of the magnetic capture particles could be labeled with one or more references, while the remainder of the magnetic capture particles is reference free.

As with the assay depicted in FIG. 1, one of ordinary skill in the art upon review of the presently disclosed subject matter would recognize that magnetic capture particle 200, SERS-active nanoparticle 220, and combinations thereof, can be included in the container before the sample is disposed therein, or can be added to the container prior to, concurrent with, or subsequent to disposing the sample therein.

The presently disclosed subject matter also encompasses embodiments in which the magnetic particle-SERS-active nanoparticle sandwich is pre-complexed and can be used with the presently disclosed methods as a reference label. This complex is inert, that is, it does not complex with the analyte of interest. A known amount of such pre-complexed particles can be added to a sample as a reference.

H. Use of Lysis Reagent in Liquid-Based Assay

In a further embodiment, a lysis reagent can be used in an assay, such as a liquid-based assay, with or without magnetic pull-down. When used in biological matrices, such as human blood, plasma, or serum, a lysis reagent can provide an increased signal and/or improved limit of detection for biomarkers. In particular, when used in an immunoassay using SERS-active particles, the addition of a lysis reagent increases the Raman signal intensity when compared to samples that do not contain the lysis reagent.

One lysis reagent suitable for use with the presently disclosed methods includes one or more of the following components: (4-(2-hydroxyethyl)-1-piperazineethanesulfonic acid) (HEPES) buffer, sodium chloride, ethylenediaminetetraacetic acid (EDTA), beta glycerophosphate, Triton® and protease inhibitors, and combinations thereof. See, e.g., Hirsch, L. R., et al., "A Whole Blood Immunoassay Using Gold Nanoshells," Anal. Chem. 75, 2377-2381 (2003). Many detergents are suitable for use as a lysing reagent. Representative examples of anionic detergents include, but are not limited to, the salts of cholic acid, caprylic acid, sodium dodecyl sulfate (SDS), and deoxycholic acid. Representative examples of cationic detergents include, but are not limited to, cetylpyridinium and benzalkonium chloride. Representative examples of zwitterionic detergents include, but are not limited to, 3[(3-Cholamidopropyl)dimethylammonio]-propanesulfonic acid (CHAPS) and phosphatidylcholine. Representative examples of nonionic detergents include, but are not limited to, digitonin, Tween® 20 (polyoxyethylenesorbitan, monolaurate) and Triton® X-100. The lysis reagents also can include protease inhibitors, including, but not limited to, aprotinin, EDTA, leupeptin, α-macroglobulin, pepstatin, phenylmethylsulphonyl fluoride (PMSF), tosyl-L-lysine chloromethyl ketone (TLCK), and tosyl-L-phenylalanine chloromethyl ketone (TPCK), and can be selected depending on the particular protease target.

Other lysis reagents suitable for use with the presently disclosed subject matter include, but are not limited to, dithiothreitol, ethylene glycol tetraacetic acid (EGTA), sodium cholate, sodium deoxycholate, NP-40, Glycocholic acid, sodium taurocholate, taurodeoxycholic acid, hexadecyltrimethylammonium bromide, Brij 35, Brij 58P, N-Decanoyl-N-methylglucamine, Igepal CA-630, N-Nonanoyl-N-methylglucamine, octyl-b-D-1-thioglucopyranoside, Span 20, Triton® X-114, Tween® 40, Tween® 80, 3-(4-heptyl) phenyl 3-hydroxy propyl) dimethylammonio propane sulfonate, and amidosulfobetaine-14. Lysis reagents also can be used to lyse cells.

One of ordinary skill in the art would appreciate that other lysis reagents known in the art also are suitable for use with the presently disclosed methods. Further, one of ordinary skill in the art would appreciate that the lysis reagent is contacted with the sample in an amount effective to lyse substantially all of the cellular contents of the sample. An example of this method is provided in Example 2.

As provided in Example 2, in immunoassays detected by SERS, addition of a lysis reagent to a sample under test results in higher signal levels and/or increased sensitivity for biomarker detection in biological matrices when compared to samples containing no lysis reagent. Increased sensitivity offers many benefits, e.g., the "time to result" can be decreased and patient outcome can potentially be improved. The larger Raman signals observed in the presence of the lysis reagent also can lead to reduced instrumentation costs. The lysis reagent could be used to increase sensitivity for a variety of assays, including but not limited to, lateral flow assays, enzyme linked immunosorbant assays, and surface plasmon resonance assays. The lysis reagent also can be used to treat types of biological samples other than blood, serum or plasma, such as sputum for tuberculosis detection, or any other type of specimen used for diagnostics that requires the detection of a biomarker. Individual components in the lysis reagent could be used alone or in combinations to achieve similar effects.

I. Representative Instrumentation for Detecting a SERS Signal Emitted by a Sample Under Test Referring now to FIG. 4, a representative system for use with the presently disclosed assays is provided. System 400 includes light source 402 capable of producing electromagnetic radiation capable of inducing a Raman signal in a SERS-active particle. In some embodiments, light source 402 is a laser, which in some embodiments, is a laser capable of operating in the near-infrared spectral region, e.g., a solid-state diode laser with an emission wavelength of about 785 nm. Electromagnetic radiation emitted from light source 402, e.g., light of one or more particular wavelengths, can be directed by fiber 404 to lens 406*a*. Fiber 404 can be any optical fiber suitable for use with the presently disclosed system. For example, fiber 404 can be single fiber 404*a* or fiber bundle 404*b*.

Lens 406*a* expands the light transmitted through fiber 404 and directs the light through filter 407*a*, which can be, in some embodiments, a bandpass filter, and onto beamsplitter 408, e.g., a dielectric beamsplitter. A portion of the light incident on beamsplitter 408 is directed to lens 406*b*, which focuses the light onto sample 412, which is contained in container 410, e.g., a specimen collection container or an assay vessel. Sample 412 can comprise one or more magnetic capture particle-analyte-SERS-active nanoparticle complexes as disclosed herein. The light incident on sample 412 is capable of inducing a SERS signal, i.e., scattered radiation, from the magnetic capture particle-analyte-SERS-active nanoparticle complexes comprising sample 412. Scattered radiation emitted from sample 412 is collected by lens 406*b* and is directed to beamsplitter 408. A portion of the scattered radiation is transmitted through beamsplitter 408 and directed to filter 407*b*, e.g., a longpass filter. After passing through filter 407*b*, the scattered radiation is directed to lens 406*c*, which focuses the scattered radiation onto fiber 414. Fiber 414 can be any optical fiber suitable for use with the presently disclosed system. For example, fiber 414 can be single fiber 414*a* or fiber array 414*b*. Fiber 414 directs the scattered radiation to spectrometer 416, which, in some embodiments, includes charge-coupled device (CCD) 418.

In some embodiments, a laser serves as the excitation source of the incident radiation used to detect one or more target analytes of interest. One of ordinary skill in the art upon review of the presently disclosed subject matter could ascertain the type of laser, including the strength and excitation wavelength, suitable for use with the SERS-active reporter molecules described herein. Radiation scattered or emitted from the sample can be detected using detection systems known in the art.

In some embodiments, more than one type of radiation source, or more than one excitation wavelength, can be used. For example, in embodiments wherein two analytes of interest are to be detected, the reagent can include two distinct types of SERS-active reporter molecules and/or two distinct types of specific binding members. In other embodiments, incident radiation of a single wavelength can be used to induce different Raman spectra from two or more distinct SERS-active reporter molecules. In some embodiments, however, incident radiation of different wavelengths can be used to produce distinct Raman signals for each analyte of interest. As one of ordinary skill in the art would recognize upon review of the presently disclosed subject matter, the selection of the particular wavelength(s) to be used depends on the analyte of interest, the specific binding members used, and the particular SERS-active reporter molecules used.

The presently disclosed assay can be conducted with any suitable Raman spectrometer systems known in the art, including, for example, a Multimode Multiple Spectrometer Raman Spectrometer (Centice, Morrisville, N.C., United States of America), such as the Raman spectrometer system disclosed in U.S. Pat. No. 7,002,679 to Brady et al., which is incorporated herein by reference in its entirety. More particularly, a system and method for a Raman spectroscopy assay using paramagnetic particles is disclosed in U.S. Patent Application Publication No. 2006/0240572 to Canon et al., and a Raman spectrometer system suitable for use with the presently disclosed assays is disclosed in U.S. Patent Application Publication No. 2005/0248758 to Canon et al., each of which is incorporated herein by reference in its entirety.

Sensing devices, such as optical detectors, radiation sources, and computer systems, microprocessors, and computer software and algorithms, can be used in any combination in practicing the methods disclosed herein. Accordingly, in some embodiments, software, or other computer readable instructions can be used to interpret, analyze, compile, or otherwise parse output data related to the presently disclosed optical assay. The software or other computer system can be used to display, store, or transmit output data, whether in digital or other forms to one or more users.

J. A Method for Amplifying a SERS Signal in a Liquid-Based Assay

Biological assays often require accurate yet sensitive detection of biomolecules in a variety of media. One approach toward the development of more sensitive assays is increasing the output signal of the assay. The presently disclosed method demonstrates that, in some embodiments, a signal enhancement of a factor of three or higher is possible. Accordingly, in some embodiments, the presently disclosed subject matter provides a method for amplifying output signal in a liquid-based assay of the type described above and depicted in FIG. 1.

The amplification method according to one embodiment begins with a sample being added to a solution containing both a magnetic capture particle and a reporter molecule, such as, but not limited to, as SERS-active nanoparticle comprising a SERS reporter molecule, and incubated for a short period of time, during which a sandwich complex comprising the magnetic capture particle, analyte and reporter molecule can be formed.

The signal amplification characteristic of the presently disclosed subject matter arises from the addition of another aliquot of reporter molecule, e.g., another aliquot of SERS-active nanoparticles having the same signal-producing capabilities, e.g., the same Raman reporter molecule, as the first aliquot added to the assay solution, before the magnetic capture particles are localized. This second aliquot of reporter molecule, e.g., a second aliquot of SERS-active nanoparticles, presents antibodies (or another molecule, e.g., a specific binding member) that recognizes the antibody on the first aliquot of reporter molecules, e.g., SERS-active nanoparticles, originally present in the assay. The presence of the second aliquot of reporter molecules results in a higher number of reporter molecules per sandwich in the sample under test and therefore a higher signal per sandwich complex.

For example, as depicted in FIG. 7, SERS-active nanoparticles coated with an antibody that recognizes unbound antibodies on the first aliquot of SERS-active nanoparticles can be added to the assay solution. When these secondary antibodies bind to the first aliquot of SERS-active nanoparticles, the signal level goes from one SERS-active nanoparticle per sandwich complex to three.

More particularly, referring now to FIG. 7, a representative schematic diagram of the presently disclosed assay using signal amplification method is depicted. The presently disclosed assay includes one or more magnetic capture particles 700, which have associated therewith at least one specific binding member 710a having an affinity for one or more analytes 730 of interest in a biological sample. The assay also includes a first aliquot of one or more reporter molecules 720 capable of producing a detectable signal, e.g., one or more SERS-active nanoparticles, which have associated therewith at least one binding member 710b having an affinity for the one or more analytes 730. Binding member 710b associated with reporter molecule 720 can be the same or different than binding member 710a associated with magnetic capture particles 700. Magnetic particle 700 and reporter molecule 720 are contacted with a biological sample comprising one or more analytes 730 of interest and incubated for a period of time to form magnetic capture particle-analyte-reporter molecule complex 740, e.g, an antibody-antigen "sandwich" structure, if the one or more analytes 730 are present in the biological sample.

The assay depicted in FIG. 7, then includes a second aliquot of one or more reporter molecules 750 capable of producing a detectable signal having associated therewith at least one specific binding member 710c having an affinity for the specific binding member 710b of the first aliquot of reporter molecules 720. The second aliquot of reporter molecules 750 can be disposed in container 760 prior to, concurrent with, or subsequent to disposing the sample and/or the first aliquot of one or more reporter molecules 720 therein, wherein the one or more reporter molecules of the second aliquot of reporter molecules 750 is the same as the one or more reporter molecules of the first aliquot of reporter molecules 720.

Complex 740, comprising a sandwich complex of magnetic capture particle 700, analyte 730, reporter molecule 720, having associated therewith reporter molecule 750, is exposed to a magnetic field (not shown) to induce complex 740 to migrate to a localized area of container 760, e.g., an assay vessel or specimen collection container, to form pellet 770. Pellet 770 is illuminated with incident radiation at one or more wavelengths, for example, in a system as shown in FIG. 4, to induce the reporter molecule to produce a detectable signal to detect the presence or amount of the one or more analytes in the biological sample.

One of ordinary skill in the art upon review of the presently disclosed subject matter would recognize that magnetic capture particle 700, reporter molecule 720, reporter molecule 750, and combinations thereof, can be included in container 760 before the sample is disposed therein, or can be added to container 760 prior to, concurrent with, or subsequent to disposing the sample therein;

Depending on the form of the assay, the second aliquot of SERS tags can be added at any stage, e.g., sequentially or concurrently with the first aliquot of SERS tags, or sequentially or concurrently with the sample. Also, to avoid a large increase in background noise in the assay, it is preferable that the biomolecule on the surface of the second SERS-active nanoparticle not recognize the biomolecule on the surface of the magnetic capture particle. In the case of an immunoassay, this characteristic can be accomplished by immobilizing biomolecules, e.g., antibodies that originate in different species on the magnetic capture nanoparticle and SERS-active nanoparticle. For example, in some embodiments, the initial assay solution could include magnetic capture particles having antibodies produced in goat and the SERS-active nanoparticle could present antibodies raised in mouse. If the second aliquot of SERS-active nanoparticles is labeled with an anti-mouse antibody, no binding to the magnetic capture particle will take place. The presently disclosed amplification method can be used to detect virtually any analyte, including DNA, provided two binding partners with orthogonal epitopes are used.

An additional benefit of increased signal output in a given assay is that less sophisticated (and less expensive) detection systems can be used to test for an analyte.

Referring now to FIG. 8, representative results of the presently disclosed amplification strategy are provided. FIG. 8A shows a typical binding curve for a homogenous protein assay without amplification as shown previously in FIG. 1. The y-axis is the output of an algorithm that quantifies the level of SERS signal for each sample. FIG. 8B shows the assay performed with the identical reagents and concentrations with the amplification step shown in FIG. 7. The graph shows signal increases of three-fold or greater upon inclusion of the amplification step.

The presently disclosed method can be used to detect virtually any analyte provided two binding partners with orthogonal epitopes are used. For example, in some embodiments, the presently disclosed amplification method can be used to detect a polynucleotide. The use of the term "polynucleotide" is not intended to limit the presently disclosed methods to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. More particularly, the term "polynucleotide" is intended to encompass a singular nucleic acid, as well as plural nucleic acids, and refers to an isolated nucleic acid molecule or construct, e.g., messenger RNA (mRNA), plasmid DNA (pDNA), or short interfering RNA (siRNA). A polynucleotide can be single-stranded or double-stranded, linear or circular. A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. Examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. Isolated polynucleotides also can include isolated expression vectors, expression constructs, or populations thereof. "Polynucleotide" also can refer to amplified products of itself, as in a polymerase chain reaction. The "polynucleotide" can contain modified nucleic acids, such as phosphorothioate, phosphate, ring atom modified derivatives, and the like. The "polynucleotide" can be a naturally occurring polynucleotide (i.e., one existing in nature without human intervention), or a recombinant polynucleotide (i.e., one existing only with human intervention). While the terms "polynucleotide" and "oligonucleotide" both refer to a polymer of nucleotides, as used herein, an oligonucleotide is typically less than 100 nucleotides in length.

FIG. 9 provides a representative schematic of the amplification method used for polynucleotide detection. Referring now to FIG. 9, the presently disclosed amplification method includes magnetic capture particle 900 having attached thereto capture probe 910a, e.g., a capture probe having 15 base pairs. Also provided is reporter molecule 920, e.g., a SERS-active nanoparticle, having attached thereto capture probe 910b, e.g., a capture probe having 15 base pairs. When contacted with target polynucleotide 930, e.g., a polynucleotide having 30 base pairs, complex 940 is formed and includes double-stranded polynucleotide 950 comprised of target polynucleotide molecule 930 and capture probes 910a and 910b. Complex 940 can then be contacted with reporter molecule 960, e.g., a SERS-active nanoparticle, having attached thereto capture probe 910c, e.g., a capture probe complementary to unbound capture probe 910b attached to reporter molecule 920 to form complex 980, which includes double-stranded polynucleotide 970 comprising capture probes 910b and 910c. Complex 980 is exposed to a magnetic field (not shown) to induce complex 980 to migrate to a localized area of a container, e.g., an assay vessel or specimen collection container as shown in FIG. 7, to form a magnetized pellet. The pellet is illuminated with incident radiation at one or more wavelengths, for example, in a system as shown in FIG. 4, to induce the reporter molecule to produce a detectable signal to detect the presence or amount of the one or more target DNA in the biological sample.

Data from the presently disclosed DNA assay are shown in FIGS. 10A and 10B.

K. Generating Improved Raman Reference Spectra and Spectral Analysis in Magnetic Pull-Down Liquid-Based Assay The presently disclosed subject matter, in another embodiment, provides a method of generating reference spectra for use in Raman Spectroscopy-based analyses. This method can be used advantageously with magnetic particle-coupled nanoparticles in liquid assays of the type disclosed herein. To determine the quantity of a specific SERS-active nanoparticle in a sample, a Raman signal generally must be generated by a known amount of the specific SERS-active nanoparticle. Typically, that known or reference signal is generated by specific SERS-active nanoparticles in solution, as sample processing can be simplified.

In some assay systems, such as those disclosed herein, SERS-active particles are complexed with magnetic particles through the reactions involving the analyte of interest. These combined particles are pulled into a small volume by an external magnet. The Raman signal generated by the nanoparticles within this pellet can be analyzed using the reference signal previously obtained from solution.

The presently disclosed subject matter provides, however, that the Raman spectra from a pellet are different from the Raman spectra from solution, even if the same single SERS-active nanoparticle type is contained in the sample. Improved results can be obtained if the reference spectra referred to above are acquired of the pellet, not from solution. The differences in these solution spectra as compared to the pellet spectra can cause errors in quantifying the amount of nanoparticles in the sample. This observation is especially true in a multiplexing environment, where several SERS-active nanoparticles having unique Raman signals are present in the sample. For example, features within the sample signal which are not contained in the reference spectra can be interpreted as coming from other SERS-active nanoparticles within the sample (see Example 4).

The differences in spectra coming from solution and pellets do not have to be large to have an impact on the quantification of SERS-active nanoparticles (see Example 4). This is especially true when one SERS-active nanoparticle is present in large quantities and another is entirely absent. Under these circumstances, a small error can induce a false positive result for the absent SERS-active nanoparticle.

According to this embodiment, Raman spectra can be analyzed by least-squares fitting, in which case reference signals are used for each potential component. In least squares fitting techniques, the signal under analysis is assumed to be composed of a linear combination of spectra, each contribution varying by the relative amount of specific SERS-active nanoparticle within the sample. Features within the measured signal that cannot be "fit" to any of the reference signals can be largely partitioned into a background signal. If a feature of the measured signal, however, coincides with a feature of any reference signal, then the fitting will assign some portion of the total signal to that reference source. If spectra are influenced by the pelletization of the nanoparticles, for example, then those changes will necessarily contribute to errors in quantification. If those changes are captured in the reference spectra, then such errors sample analyses can be reduced. One of ordinary skill in the art would recognize that other multivariate analysis techniques, including, but not limited to, partial least squares, principal component analysis, and the like, could be used with the presently disclosed methods.

The presently disclosed subject matter, in a further embodiment, provides a method of analyzing Raman spectra, especially those obtained from SERS-active nanoparticles, and especially in a multiplexed situation where particles with different Raman spectra are used to identify multiple analytes. To determine the quantity of a specific SERS-active nanoparticle (nanoparticle with a specific SERS-active nanoparticle which generates a unique Raman signal) in a sample, a sample spectrum typically is recorded over a broad range of wavelengths or wavenumbers, and then compared to one or more reference spectra. This comparison involves fitting the sample spectra to the reference spectra over a consistent and suitable wavelength or wavenumber range.

The presently disclosed subject matter demonstrates that an estimate of nanoparticle components made from this typical comparison can be refined in two ways based on the results of the first comparison. First, because the differences between spectral contributions for different components can vary over a spectral range, specific ranges within the spectra can be weighted more heavily in the calculations depending on the relative amounts of components in the first estimate. Second, components estimated to be absent or present in very low concentrations can be removed from the analysis, and the remaining components re-estimated. In either case, an increase in fit accuracy ("goodness of fit") can be calculated and appraised. The "goodness of fit" represents a difference between the sample spectrum and the fitted spectrum and can be determined by any method known in the art and can be reported, for example, as a residual of the least squares fitting technique. These two methods can be applied in combination or separately. In addition, the presently disclosed method is applicable to a variety of SERS-active nanoparticles that similarly have spectra that must be distinguished.

II. Composite Nanostructures and Methods of Their Use

The presently disclosed subject matter provides composite nanostructures, including a composite structure, referred to herein as a "satellite" structure, comprising a plurality of signal-bearing particles, e.g., nanoparticles, bound to a core particle, and a composite structure, referred to herein as a "core-shell" structure, which includes a core particle, an active material, such as a Raman-active material, surrounding the core particle, and one or more shells, such as a metal shell, surrounding the active material. The presently disclosed satellite and core-shell structures can be used to amplify or otherwise enhance a signal in an assay, such as a SERS assay.

Accordingly, in some embodiments, the presently disclosed subject matter provides a method for performing an assay, the method comprising: providing at least one of a satellite structure, a core-shell structure, or combinations thereof; contacting the satellite structures and/or core-shell structures with a sample suspected of containing one or more target analytes, and performing a detection step to determine the presence or absence of the one or more target analytes in the sample.

More particularly, in one embodiment, signal enhancement can be achieved by providing a composite structure having a plurality of signal-bearing satellites (e.g., nanoparticles) bound to a core particle (e.g., a microparticle) such that the resulting composite satellite structure is capable of generating multiple signals. Thus, the satellite structure can improve the detection of analytes within an assay, such as for samples having a lower concentration of analytes.

According to various aspects of the presently disclosed subject matter, the satellite particles can be metal, semiconductor, organic, and/or inorganic nanoparticles. Similarly, the core particle can be magnetic, silica, metal (e.g., gold), or organic microparticles or nanoparticles. The satellite and core particles can be spherical or non-spherical in shape. The satellite particles can be bound to each core particle using electrostatic, covalent, or van der Waals forces. In addition, the satellite particles typically comprise a reporter molecule, such as fluorescent, Raman-active, or enzyme reporter molecules which facilitates detection. The satellite particles and/or the at least one core particle can have further molecules bound thereto, such as antibodies, nucleic acid probes, or blocking agents.

In a further embodiment, the presently disclosed subject matter provides a core-shell structure comprising a core particle, an active material, such as a Raman-active material, surrounding the core particle, and a shell surrounding the active material, wherein the shell can be a contiguous layer or a plurality of nanoparticles, which preferably are in close proximity to one another. The core and shell materials can be the same or different, and are desirably chosen from materials that enhance the spectrum of the active material. For example, a gold core and gold shell will improve the detectable spectrum of a Raman-active material in a surface enhanced Raman scattering application.

Additional aspects of the method can include detecting a target analyte using surface enhanced Raman scattering. A plurality of magnetic, metallic, or semiconductor beads having, e.g., an antibody for the target analyte, can be introduced into the assay, along with a composite structure having a similar binding molecule for the target analyte. The analyte, if present, becomes sandwiched between the composite structure and the bead. The bead can be manipulated, e.g., by application of a magnetic field, to concentrate a plurality of the sandwiches for detection via Raman spectrum. A further aspect of the presently disclosed subject matter includes contacting a plurality of the presently disclosed composite structures with a cell or tissue under conditions to attach the composite structure to an analyte (e.g., a normal or cancerous cell) and imaging the structures.

A. Satellite Nanostructures

The presently disclosed subject matter provides microparticle-nanoparticle satellite structures, which, in some embodiments, can be used to amplify or enhance a signal in an assay, such as a SERS assay.

Referring now to FIG. 14, there is shown a transmission electron micrograph (TEM) of satellite structure 1400 according to one embodiment of the presently disclosed subject matter. Satellite structure 1400 includes a plurality of smaller particles (e.g., a signaling moiety) bound to a larger particle (e.g., a carrier), such as a plurality of nanoparticles 1412 bound to microparticle 1414. As disclosed in further detail herein below, satellite structure 1400 is capable of amplifying an analyte signal in an assay. Thus, satellite structure 1400 can be able to amplify a signal to detect an analyte that can otherwise not be detected, such as in samples containing lower concentrations of analytes.

It is understood that satellite structure 1400 described herein can be used to detect any number of analytes. The term "analyte" is not meant to be limiting and can be any molecule of interest such as a protein, nucleic acid, or metabolite. The analyte could alternatively be a cell, such as a cancerous cell. Furthermore, the assay used to analyze analytes can be homogeneous or heterogeneous. For instance, a heterogeneous assay typically requires separation, either by washing or other physical means, of the reaction elements between the individual steps of the assay procedure, while a homogeneous assay does not require any separating steps. In addition, any desired assay can be used to identify and analyze the analytes. For example, sandwich immunoassays can be used, examples of which are provided in further detail herein. Further, satellite structure 1400 can be used to amplify signaling events for a plurality of analytes such that multiplex detection can be used to detect such plurality of analytes. For example, a first satellite structure with a distinct signal, e.g., a distinct SERS spectrum includes an antibody for a first analyte, and is mixed directly with a second satellite structure exhibiting a different, distinct signal, e.g., a distinct SERS spectrum, and having a second antibody specific for a second type of analyte.

Nanoparticles 1412 can be any suitable particle capable of generating a detectable signal that is used to detect the occurrence of a binding event. For example, nanoparticles 1412 can be metal, semiconductor, organic, or inorganic nanoparticles. In the example shown in FIG. 14, nanoparticles 1412 are gold particles. Similarly, microparticle 1414 can be any desired carrier that facilitates attachment of a plurality of nanoparticles 1412 thereto. For instance, microparticle 1414 could be magnetic, silica, metal (e.g., gold), and/or organic microparticles. In the example depicted in FIG. 14, the microparticle is an amine-functionalized silica particle. Nanoparticles 1412 typically are able to provide detectable signals themselves, e.g., they can be, quantum dots or SERS-active particles. Other particles suitable for use with the presently disclosed methods are known to those of ordinary skill in the art. For example, each of nanoparticles 1412 can contain a reporter molecule such as fluorescent, Raman, and enzyme reporter molecules that enable the nanoparticles to act as signaling elements if the nanoparticles are not otherwise capable of doing so on their own. See, for example, U.S. Pat. No. 6,514,767, the disclosure of which is hereby incorporated by reference in its entirety.

Although the term "microparticle" is used throughout, it is understood that microparticle 1414 could be any particle that is larger than nanoparticles 1412 (where nanoparticles are defined to have sizes of about 2 nm to about 200 nm in diameter). Various techniques can be used to bind nanoparticles 1412 to each microparticle 1414, such as using electrostatic, covalent, or van der Waals forces. Furthermore, nanoparticles 1412 could be attached to microparticle 1414 using various linkers, such as polymers, DNA, amino acids, short-carbon chains, streptavidin/biotin linkage, or the like, which can allow for a higher density of nanoparticles about the microparticle. The length and type of the linker can be chosen to tune the number of nanoparticles 1412 attached to microparticle 1414, and the spacing between the nanoparticles and microparticles. Nanoparticles 1412 and/or microparticle 1414 also could be coated (e.g., with a polymer) to control interparticle interactions.

Any number of nanoparticles 1412 can be bound to microparticle 1414, although the precise number of nanoparticles can be dictated by the particular experiment being performed. For example, it can be possible to obtain satellite structure 1400 having a uniform and maximum distribution of nanoparticles 1412 to microparticle 1414 by optimizing the ratio of the particles and mixing conditions during the reaction. Furthermore, nanoparticles 1412 and microparticle 1414 can be of various sizes and configurations depending on the analyte to be detected, such as spherical or non-spherical (e.g., nanorods) in shape. For example, FIG. 14 shows a transmission electron microscopy image, wherein nanoparticles 1412 and microparticle 1414 are spherical in shape, and the nanoparticles are 40 nm in diameter and the microparticle is 1 μm in diameter. In addition, microparticle 1414 can be submicron (e.g., 0.5 μm) in diameter.

Further, nanoparticles 1412 and/or microparticle 1414 can be labeled with a species, such as organic or inorganic compounds, polymers, proteins, receptors, antibodies, nucleic acid probes, and blocking agents, to enhance or facilitate the binding event with the analyte or facilitate the binding event with the analyte or to prevent undesired interactions. Exemplary blocking agents include albumin, casein, polyvinyl alcohol, poly (ethylene glycol), and gammaglobulin.

Various detection techniques can be used to detect one or more analytes of interest via satellite structure 1400, e.g., fluorescence or Raman spectrometry. To perform the detection, at least one binding event typically exists between satellite structure 1400 and an analyte (e.g., via a sandwich as described below). Amplification of the signal results from each of a plurality of nanoparticles 1412 generating multiple signals based on a single binding event, rather than a single nanoparticle generating only one signal from that binding event.

FIG. 15 depicts sandwich assay 1500 according to one embodiment of the presently disclosed subject matter. In particular, the assay includes antibody 1522a immobilized on support 1524, while satellite structure 1510 also includes antibody 1522b immobilized on one of nanoparticles 1512. While this particular embodiment illustrates that antibody 1522b is coupled to satellite structure 1510 via nanoparticles 1512, it is understood that in some embodiments it can be advantageous to attach antibody 1522b to carrier microparticle 1514. Analyte 1516 is captured between antibodies 1522a, 1522b, which results in a binding event. Satellite structure 1510 facilitates the generation of a plurality of detectable signaling events due to the signaling events by each of nanoparticles 1512, which results in amplification of the binding event between analyte 1516 and nanoparticle 1512 capturing the analyte. It is understood that antibody 1522a on support 1524 and antibody 1522b on satellite structure 1510 need not be the same.

FIG. 16A illustrates sandwich assay 1600 according to another embodiment of the presently disclosed subject matter. Assay 1600 includes assay vessel 1628 containing a plurality of satellite structures 1610, analytes 1616, and beads 1630. Beads 1630 can be a magnetic, semiconductor, or metallic material that are capable of being attracted by a magnetic field, or can be structures that otherwise facilitate separation/enrichment, e.g., via gravity or centrifugation. There can be any number of beads 1630 depending on the number of satellite particles 1610 and analytes 1616, and the beads can be any size and configuration capable of sandwiching an analyte between the bead and a satellite structure. For example, according to one exemplary embodiment, which is not meant to be limiting, sandwich assay 1600 can include about 1,000 to 100,000 beads 1630, about 1,000 to 100,000 satellite structures 1610 per assay, and about 50 to 10,000 nanoparticles 1612 per microparticle 1614. In addition, beads 1630 can have located thereon species such as antibodies, nucleic acid probes, blocking agents, or the like.

Analyte 1616 can be captured or sandwiched between satellite structure 1610 and bead 1630. In this regard, analyte 1616 can attach to nanoparticle 1612 of a respective satellite structure 1610, while bead 1630 can attach to the analyte such that the analyte is sandwiched between the nanoparticle and the bead resulting in a binding event. After allowing a predetermined time for a plurality of analytes 1616 to be captured, a magnetic field (provided, for example, by a permanent magnet or an electromagnet) can be applied to assay 1600, which concentrates sandwiched analytes 1616 in a particular location, for example the bottom of assay vessel 1628 as concentrated pellet 1632, as shown in FIG. 16B. Pellet 1632 can be formed at the bottom or the side of assay vessel 1628 depending on the direction that the magnetic field is applied. Pellet 1632 can then be analyzed to determine the presence of analytes 1616 via the signals provided from the satellite structures. The signal resulting from each satellite structure 1610 is enhanced by the presence of the plurality of nanoparticles 1612 as described above. Surface enhanced Raman scattering (SERS) can be used to detect signals from satellite structure 1610 containing Raman-active material.

A further embodiment of the presently disclosed subject matter is directed to cellular imaging, wherein satellite structure 1610 can be used to facilitate the analysis of a cell. Using conventional techniques for analyzing cells, a limited number of particles can be capable of attaching to a cell, such as a cancerous cell, to facilitate the imaging of the cell for identifying normal or cancerous cells. For example, a cell having ten surface markers attached thereto would only be capable of binding to ten nanoparticles such that there can only be ten signaling events corresponding to ten surface markers. By sending satellite structures 1610 to attach to a cell, each having a plurality of nanoparticles, a plurality of signaling events can be generated by binding each satellite structure to the cell. For instance, continuing with the example above, there can be ten satellite structures 1610 that each includes ten nanoparticles 1612 such signal is generated from 100 nanoparticles, thus amplifying each individual binding event by a factor of 10. As such, the amplification of the signaling events can enhance the identification of the cell using cellular imaging. As discussed above, satellite structures 1610 can be labeled, such as with an antibody coating, to facilitate the binding events. The size of satellite structure 1610 can be tailored to enable decoration of a cell by a maximum number of nanoparticles 1612 by optimizing the size of microparticle 1614 to which nanoparticles 1612 are attached. Thus, if microparticle 1614 is very small, only a handful of nanoparticles 1612 can be attached to it. On the other hand, if microparticle 1614 is very large, only a few satellite structures 1610 can be bound to the cell.

B. Composite Core-Shell Nanoparticles

In some embodiments, the presently disclosed subject matter provides composite particles, referred to herein as "core-shell" structures, which include a core particle, an active material, such as a Raman-active material, surrounding the core particle, and one or more shells, such as a metal shell, surrounding the active material, which, in some embodiments, can be used to amplify or enhance a signal in an assay, such as a SERS assay Referring now to FIG. 17, composite structure 1700 comprises core 1702, an active material, such as Raman-active material 1704 around the core, and contiguous shell 1706 around the active material. Typically outer shell 1706 is 20 nm thick or less. In one specific embodiment, core 1702 is a gold core about 20 to about 200 nm in diameter, shell 1706 also is gold and has a thickness of 2 to 20 nm, and the active material is a Raman-active material such as trans-1,2-bis(4-pyridyl)ethylene (SPE). In addition, a thin, <5 nm, silica layer can be disposed on the Raman-active material under shell 1706. The silica is advantageous in some situations to promote fabrication of the gold shell. Alternatively, a bi-functional molecule can be used to promote binding of gold to the Raman-active material. Gold is an advantageous metal in providing surface enhanced Raman scattering, but metals such as silver and copper (or alloys of any such metals) also are useful.

In a further embodiment of the core-shell composite structure, the core-shell structure is similar to FIG. 17, but with the shell being made up of nanoparticles, typically having a size equal to or smaller than the core. In one such embodiment, the core is a gold core about 20 nm to about 200 nm in diameter, the active material is a Raman-active material such as trans-1,2-bis(4-pyrridyl)ethylene (BPE), and the nanoparticles also are gold and have a diameter of about 2 nm up to the size of the core. In addition, a thin, <5 nm, silica layer can be deposited on the Raman-active material under the nanoparticles. Alternatively, a bi-functional molecule can be used to promote binding of gold to the Raman-active material. Gold is an advantageous metal in providing surface enhanced Raman scattering, but metals such as silver and copper (or alloys of any such metals) also are useful.

It is understood that the embodiments shown in FIGS. 14-17 and described above are not meant to be limiting. In particular, the satellite and core/shell structures of the presently disclosed subject matter can be used in a variety of assays for enhancing analyte signals, such as a homogeneous assay or a lateral flow assay. It is possible that a single assay would use both types of particles. The size, number, material and configuration of nanoparticles 1512, and microparticles 1514 can be varied depending on analyte 1516 being identified and a desired amplification of a signaling event. Similarly, for core/shell structures 1700, the size, material, and thicknesses can be adapted for the particular assay or environment.

As noted, a particularly advantageous application for the presently disclosed subject matter is for surface enhanced Raman scattering. When two metallic nanostructures are in close proximity, electromagnetic coupling of the plasmonic fields from the two structures takes place, producing large electromagnetic field enhancements. When a Raman active molecule is placed in the enhanced electromagnetic field, the intensity of the Raman signal from the molecule shows an increase of several orders of magnitude versus the signal when the molecule is on an isolated nanoparticle. Conventionally, those in the art have attempted to aggregate multiple metallic nanoparticles, but such aggregation is difficult and largely uncontrollable. The presently disclosed subject matter is able to provide the desired electromagnetic coupling, but in a more advantageous manner.

In addition, while not limited to any particular theory, it is believed that the two interacting plasmonic structures (either core and shell or core and satellites) will allow one to tune the wavelength at which surface plasmon resonance of the composite structure occurs. This tuning in combination with the wavelength of an excitation laser is expected to further enhance the Raman signal from the composite structures, thereby increasing the sensitivity of any assay.

The composite structures of the presently disclosed subject matter can be manufactured by any appropriate technique. For example, the following patent documents provide disclosure on nanoparticle formation, including silica coatings: U.S. Pat. Nos. 6,548,168 and 6,514,767 and U.S. Patent Application Publication No. 2001/0002315, the disclosures of which are here by incorporated by reference. Other methods for forming and manipulating metallic particles are known to those skilled in the art.

In addition to the spherical particles discussed above, other configurations are possible, such as rod-shaped or other elongated shaped particles, and cores comprising multiple particles.

III. Sample Tube and Methods of using the Same

The presently sample tubes, and methods of using the same, can be used with any of the presently disclosed particles or assay methods.

A. Sample Collection Containers Generally

In some embodiments, the sample container is selected from the group consisting of a cuvette, a tube, such as a blood collection tube, generally, an assay vessel, or any other sample collection container compatible with the sample under test and SERS measurements. In some embodiments, the sample collection container, e.g., a tube, can have an internal pressure that is less than the atmospheric pressure of the surrounding environment. Such sample collection containers are disclosed in U.S. Pat. No. 5,860,937 to Cohen; U.S. Pat. No. 5,906,744 to Carroll et al.; and U.S. Pat. No. 6,821,789 to Augello et al., each of which is incorporated herein by reference in their entirety. Further, in some embodiments, the sample collection container includes a detection reagent comprising the presently disclosed SERS-active nanoparticles. In such embodiments, the sample collection container has a detection reagent disposed therein before the user, e.g., a patient or a medical technician, collects the biological sample, e.g., blood, to be detected. The detection reagent, for example, can be immobilized on an inner surface, e.g., an inner wall, of the sample collection container or simply otherwise disposed within the sample container.

The sample collection container, for example, a blood collection tube, can be shipped to the user with the detection reagent disposed therein. Alternatively, the user can select a suitable detection reagent and introduce the detection reagent into the collection device before collecting the sample specimen. Further, the presently disclosed subject matter can include a kit comprising one or more of a sample collection container, such as a blood collection tube, one or more reagents, such as one or more detection reagents comprising nanoparticles having a SERS-active reporter molecule attached thereto, magnetic capture particles, and individual components thereof. Such kits can include any number of the components of the assay, including, but not limited to, multiple reporter molecules or multiple specific binding members either attached to a nanoparticle or packaged separately therefrom.

B. Presently Disclosed Sample Collection Containers

In conventional immunoassays, detection of an antigen can occur by "sandwiching" the antigen between two antibodies, one of which is labeled with an optical or colorometric reporter. The measured optical signal can then be used to determine the concentration of the antigen present in the sample. Conventional Enzyme-Linked Immunosorbent Assay (ELISA) immunoassays are examples of this type of technology.

A magnetic capture assay involves coating small magnetically susceptible particles, such as microbeads ranging in size from a few hundred nanometers to tens of micrometers, with a target-specific substance, for example a ligand or an antibody. The particles are introduced into a well containing a solution of the target entities, and unwanted biological molecules. The target entities then bind to the coating on the magnetic particles. Cells, proteins, nucleic acid sequences and the like are examples of target entities. Magnets are placed near the well to apply magnetic fields on the well and the solution.

The magnetic particles, including the target entities bound to the particles, are attracted to the magnets. The magnets provide a magnetic force sufficient to accumulate the particles in an expedient manner. Depending on placement of the magnet, the particles can be collected in the bottom or the side walls of the wells. A uniform particle separation profile is desirable, such as a profile in which the beads uniformly distribute about the base of each well to produce a "flat profile," or in which the particles pull to the sides of the wells equally.

In another assay format, a magnetic capture assay using surface enhanced Raman scattering (SERS) reporters, an optical signal is generated by forming an antigen-mediated complex between a SERS-labeled nanotag and a magnetic capture particle. Referring once again to FIG. 1, an example of magnetic capture SERS assay is illustrated. With this technical approach, the magnitude of the optical signal can depend on the size, density, and position of the magnetic particle pellet.

Figure 5:
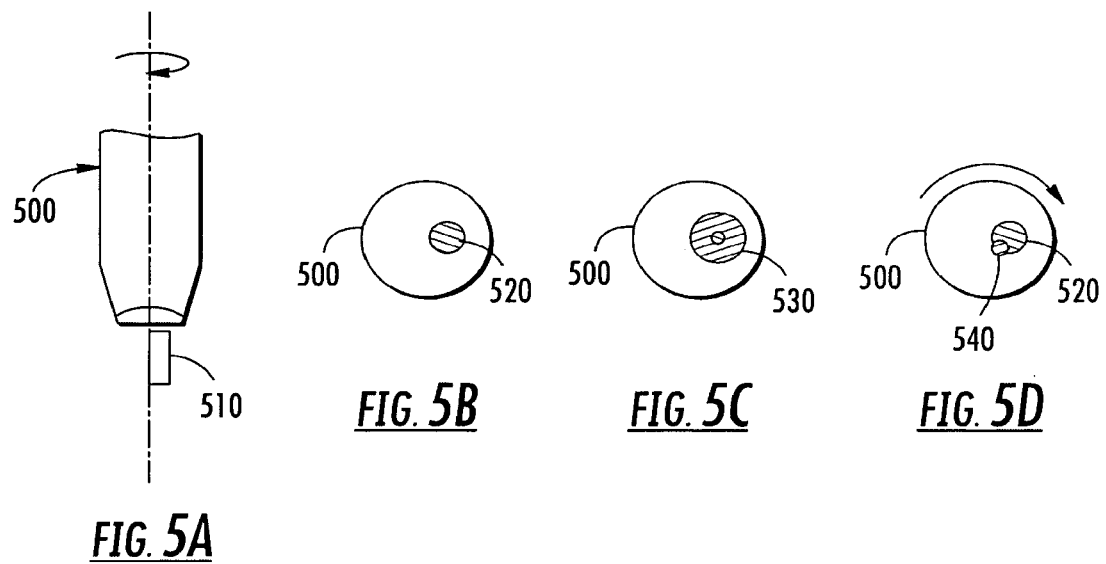

The size, density, and position of the magnetic particle pellet relative to the interrogating optics can affect the magnitude and reproducibility of the measured optical signal. For example, altering the surface functionality of the magnetic particles can change the shape of the pellet, which then could lead to significantly different optical signals. In previous sample analysis tube designs having a large window, the assay reaction can be quenched by holding the tube above a magnet to attract the magnetic particles down to the bottom of the tube. Because the window of the tube is relatively large in comparison to the absolute number of magnetic particles, a dense pellet might not be consistently formed and an additional step for the pellet formation can be needed. One method for forming a consistent magnetic pellet includes using a magnet mounted below the sample tube, where the center of the magnet is positioned off center in respect to the sample tube axis. This method is illustrated in FIG. 5. It can typically take only a few seconds for the magnet to induce formation of a pellet at the bottom of the sample tube. Typically, the pellet takes the shape of a torus, where almost no particles can be found in the center of the pellet. Rotating the sample tube around its center axis can modulate the magnetic field experienced by the pellet in such a way that the pellet becomes denser. Thus, in some embodiments, the presently disclosed subject matter provides a method for the reliable creation of small and dense magnetic particle pellets.

Referring now to FIG. 5, a process of reliable pellet formation by rotating the sample tube above an off-center mounted magnet is illustrated. FIG. 5A shows a side view of sample tube 500 and magnet 510. As shown in FIG. 5A, magnet 510 (e.g., a rod) is mounted below sample tube 500, where the center of the magnet is positioned off center in respect to the sample tube axis (shown as dashed line in FIG. 5A). A top view of container 500 and magnet 510 is shown in FIG. 5B, where the top of magnet 510 is depicted as cross-sectional area 520. In a liquid-based assay of the type described herein, it typically takes a short period of time, e.g., a few seconds, for magnet 510 to induce formation of a pellet at the bottom of sample tube 500. Typically, the pellet takes the shape of a torus, where almost no particles can be found in the center of the pellet. FIG. 5C shows a top view of the formation of pellet 530 in the shape of a torus. Cross-sectional area 520 of magnet 510 can be seen through the center of pellet 530, which contains almost no particles. The presently disclosed subject matter provides that rotating sample tube 500 around its center axis modulates the magnetic field experienced by pellet 530 in such a way that pellet 530 becomes denser. Referring now to FIG. 5D, a top view of a denser pellet 540 formed after rotating sample tube 500 around its center axis is shown.

C. Pellet Formation in Liquid-Based Assay using Magnetic Particles

The small size of the magnet and the additional rotation of the sample tube can lead to a more reliable and dense magnetic particle pellet. Fluctuations in the magnet position, as well as in the rotation speed, however, can modulate the pellet position and density and therefore ultimately can change the measured optical signal. Steps to form the magnetic particle pellet must therefore be performed with care and skill. Accordingly, a need exists for a system for forming a magnetic particle pellet having a consistent density and shape in a sample tube, and which can be achieved with a simpler process.

Referring once again to FIGS. 1 and 4, an example of a magnetic capture assay and detection system is illustrated. The assay uses capture antibodies attached to magnetic particles. Detection antibodies are attached to surface-enhanced Raman scattering (SERS) labeled nanoparticles. The capture antibody and the detection antibody each specifically bind to different and distinct epitopes on a target analyte. Consequently, an antigen-mediated complex between the SERS-labeled nanoparticle and the magnetic capture particle (S-A-M "sandwich") can form. The S-A-M sandwich complexes can then be segregated from the sample solution by applying a magnetic field. A magnet is used to attract the sandwich complexes to the bottom of the tube where an optical signal from the resulting magnetic particle pellet is measured. The presently disclosed subject matter can be used with this process and technique.

With this technical approach, the magnitude of the optical signal can depend on the size, density, and position of the magnetic particle pellet. The shape of the magnetic pellet might not always be consistent. For example, altering the surface functionality of the magnetic particles can change the density and/or shape of the pellet. As shown in FIG. 5, alternative approaches use a magnet mounted below a sample tube. A small pellet can be formed in the bottom of the sample tube by rotating the sample tube around its center axis. Also provided herein are sample tubes for use in the presently disclosed methods.

Referring now to FIGS. 18A to 18C, according to at least one embodiment of the presently disclosed subject matter, a sample tube 1810 can comprise an elongated body 1812 having an open end 1814, and a conical portion 1816 having a closed end 1818. Conical portion 1816 can further comprise a flat bottom 1820 at closed end 1818. The sample tube 1810 can have a center longitudinal axis 1822 that is normal to flat bottom 1820. While the embodiments exemplified in FIGS. 18A-18C illustrate a cylindrical elongated body 1812, the presently disclosed subject matter is not limited to a sample tube having this shape. Elongated body 1812 can have any desired shape, such as, for example, triangular, square, multi-sided, like pentagonal, hexagonal, and octagonal, and other geometrical shapes. The shape of the elongated body is not critical. Conical portion 1816, exemplified in FIGS. 18A to 18C, also is not limited to a circular cone and can have any tapered shape, such as an outer shape that matches the elongated body or a shape different from the elongated body, as long as the portion is tapered or otherwise leads to a reduced diameter or dimension compared to the diameter or dimensions of the elongated body.

According to various embodiments, sample tube 1810 can comprise a wall 1824 having a thickness 1825 ranging from about 0.1 mm to about 1.25 mm, for example, about 0.635 mm. Any wall thickness is acceptable, and wall thicknesses above and below this given thickness can be used. According to various embodiments, elongated body 1812 can have an inner diameter 1826, at open end 1814, ranging from about 2.0 mm to about 25 mm, for example, in some embodiments, about 2.0 mm to about 12 mm, or in particular embodiments, about 10.2 mm. Any inside or inner diameter can be acceptable, and inner diameters above or below these given amounts can be used. Also, when a geometric shape is used that does not have a diameter, the recited diameters can serve as a length or average length or longest length across the space defined. This characteristic applies to all aspects of the presently disclosed subject matter.

The elongated body 1812 can taper toward conical portion 1816, for instance, in a slight manner, such as at an angle ranging from about 0 degrees to about 5 degrees, such as from 1 degree to 3 degrees. Angles above or below this given amount can be used. The flat bottom 1820 can have a center axis 1834, and conical portion 1816 can taper toward center axis 1834. This angle can be from about 10 degrees to about 50 degrees, or from about 15 degrees to about 45 degrees, or from about 15 degrees to 40 degrees, or from 20 degrees to 30 degrees. Angles above or below this given amount can be used. The angle in each case is determined using the center axis 1834 as the reference line.

According to various embodiments, sample tube 1810 can have any overall length 1823, such as one ranging from about 10 mm to about 50 mm, for example, from 20 to 30 mm, such as 25.4 mm. Any overall length is acceptable, and overall lengths above and below these lengths can be used. According to various embodiments, sample tube 1810 can define an interior volume. The interior volume can range from about 0.1 mL to about 50 ml, in some embodiments, from about 0.1 mL to about 2.0 mL or more, or from about 0.2 mL to about 1.5 mL, for example, about 1.4 mL, or about 0.4 mL. Amounts above or below this range can be used and are not critical.

According to various embodiments, conical portion 1816 can have any length, such as one ranging from about 2.0 mm to about 10.0 mm, for example, about 6.35 mm. Lengths above or below this length can be used. According to various embodiments, conical portion 1816 can define an interior volume of any amount, such as ranging from about 10 µL to about 50 mL, from about 10 µL to about 5 mL, from about 10 µL to about 1 mL, from about 10 µL to about 500 µL, or from about 50 µL to about 400 µL, for example, about 200 µL. The interior volume can be above or below this range.

The sample tube 1810 can comprise a flat bottom 1820 having an inner surface 1826 and an outer surface 1828. Inner surface 1826 and/or outer surface 1828 can have an optical quality finish or polished surface. According to various embodiments, flat bottom 1820 can have any thickness, such as ranging from about 0.10 mm to about 2.0 mm, or from about 0.25 mm to about 1.0 mm, for example, about 0.635 mm. Other thicknesses above or below these amounts can be used.

According to various embodiments, flat bottom 1820 can have any inner diameter 1829 ranging, such as one from about 0.25 mm to about 10 mm, in some embodiments, from about 0.25 mm to about 2.5 mm, or from about 0.5 mm to about 1.25 mm, for example, about 1 mm. In various embodiments, flat bottom 1820 can have any outer diameter 1830, such as one ranging from about 1.25 mm to about 25 mm, for example, in some embodiments, about 1.25 mm to about 6 mm, and in some embodiments, about 2.50 mm.

In general, for any dimension or volume mentioned herein, other sample tube sizes and dimensions can be appropriate. Generally, one can take into account, for example, the type and volume of sample, the type of assay, the volume of reagents, and/or the desired size of the magnetic particle pellet.

According to various embodiments, sample tube 1810 can comprise a flange 1821 circumscribing open end 1814. Flange 1821 can have any thickness, such as ranging from about 0.25 mm to about 1.25 mm, for example about 0.80 mm.

According to various embodiments, sample tube 1810 can further comprise a cap or closure device (not shown) having an open position and a closed position for sealing open end 1814. In some embodiments, the cap can be configured to fit tightly into open end 1814. The cap can have a size and shape configured to protect and cover the perimeter of the tube opening, and help maintain the inside of the sample tube free of any contaminant. The caps can be sealed to the sample tubes by pressing them downward against a resisting frictional force. The closure can be any shape and can involve any closure technique, such as snap-fit, screw-fit, stopper, and the like. In some embodiments, the cap can be attached to sample tube 1810 by a flexible hinge.

According to various embodiments, sample tube 1810 can comprise any material that does not react with the components placed therein. According to various embodiments, the materials can have a minimal affect on the transmission of light and the background spectra. Sample tube 1810 can comprise glass, ceramic, and/or polymeric material, for example, polypropylene, polyethylene, polystyrene, polycarbonate, cyclic olefin copolymer, and the like, or any combination thereof. Sample tube 1810 can be fabricated by standard procedures, such as, for example, injection molding or other molding techniques.

According to various embodiments, sample tube 1810 can comprise a thermally conductive material and/or comprise walls having a thickness that allows for rapid heat transfer, such as occurs during polymerase chain reaction thermal cycling.

According to various embodiments, flat bottom 1820 can comprise an optical quality window. Basic characteristics of the optical window can include surface quality, thickness uniformity, and/or optical purity. Optical quality refers to minimal or no absorption and scattering loss such that desired levels of transmission can be achieved. Optical quality also includes uniformity of optical properties, such as the index of refraction. According to various embodiments, the optical quality window can have no scratches or defects larger than $\lambda/2$ or no larger than $\lambda/4$, wherein $\lambda$ is the wavelength of emitted light.

The presently disclosed subject matter is not limited to individual samples tubes. According to various embodiments, a sample tube can comprise a multi-well plate. A sample tube can comprise, for example, a 96-well plate, a 384-well plate, or a 1536-well plate. In various embodiments, the multi-well plates can be used in high throughput applications, typically involving automated systems. In such systems, for example, each 96-well plate can be arranged as 8×12 wells, each 384-well plate can be arranged as 16×24 wells, and each 1536 well plate can be arranged as 32×48 wells. Any arrangement can be used with the presently disclosed subject matter.

According to various embodiments, a system for forming a magnetic particle pellet in a sample tube can comprise a sample tube and a magnet positioned adjacent and below the sample tube. The sample tube can comprise a conical portion having a closed flat bottom, the sample tube capable of holding a volume of magnetic particles contained therein. In some embodiments, the magnet can be positioned adjacent (e.g, below) the flat bottom of the sample tube wherein the magnet is capable of providing a magnetic force sufficient to attract magnetic particles contained within the volume to the flat bottom, thus forming a magnetic particle pellet. According to various embodiments, the sample tube can contain a sample comprising magnetic particles disposed within the sample tube.

According to various embodiments, the sample tube can further contain magnetic particles disposed within the sample tube. The flat bottom of the sample tube can have an inner diameter, and a magnetic particle pellet having a diameter or size substantially the same (within 10%, within 5%, within 1% of the inner diameter) as the inner diameter can be formed.

According to various embodiments, the magnetic particles can comprise paramagnetic, superparamagnetic, and/or ferromagnetic materials. The magnetic particles can be or contain any conventional magnetic material, and can be any size/diameter. The magnetic particles can be any size, and according to various embodiments, can have a diameter ranging from about 0.05 micron to about 5.0 microns or smaller or larger diameters or lengths/widths. The magnetic particles can comprise, for example, iron oxide, magnetite, or a combination thereof. The magnetic particles can comprise encapsulated magnetic particles, for example, particles comprising a magnetite-rich core encapsulated with a polymer shell. The magnetic particles can comprise, for example, paramagnetic microspheres, such as approximately 1 micron in diameter, available from Bangs Laboratories, Inc., Fishers, Ind.

According to various embodiments, the surface area (e.g., L×W) of the magnet can be the same, greater, or less than the surface area of the flat bottom. For instance, referring now to FIG. 19, the surface area of magnet 1940 can be greater than the surface area of flat bottom 1920. Magnet 1940 can be positioned adjacent and below flat bottom 1920 of sample tube 1910. According to various embodiments, the magnet entirely overlaps and encompasses the flat bottom. According to various embodiments, the magnet can have a surface area that is greater than the surface area of the flat bottom, for instance, by a range of from about 1% to about 200%, or from about 3% to 100% or from about 5% to 50%, or from about 5% to 25%, or from about 5% to 15%, or from about 1% to 10%. There is no upper limit on how large the magnet can be with respect to surface area. A magnet having a surface area larger than, and encompassing, the flat bottom allows sample tube 1910 to be positioned with a degree of flexibility with regard to the magnet and yet still produce a consistent magnetic particle pellet.

Although the embodiment shown in FIGS. 19A and 19B illustrates a circular shaped magnet 1940, magnets of any other desirable shape can be used. Preferably, the magnets provide a substantially uniform parallel magnetic field that extends into part or all of the volume occupied by sample tube 1910 and has a uniform gradient directed toward the magnet surface. Magnet 1940 can have, for example, a triangular, square, rectangular, hexagonal, trapezoidal, or elliptical, shape, or other geometrical shape.

According to various embodiments, magnet 1940 can comprise any type of external magnetic field-producing device. Magnet 1940 can comprise, for example, one or more ferromagnets, ferrimagnets, polymer-bonded magnets, rare earth magnets, ceramic magnets, and/or electromagnets, or any combination thereof. The magnet can be an electromagnetic device. Magnet 1940 can comprise, for example, iron-oxide, magnetite, gadolinium, alnico, ticonal, barium-strontium, neodymium-iron-boron, and/or samarium cobalt, or any combination thereof and the like. Magnet 1940 can produce a sufficient magnetic field to attract all the magnetic particles to flat bottom 1920, and magnet 1940 can be positioned such that sample tube 1910 is within the influence of the magnetic field provided by magnet 1940. If the magnetic field is too weak, magnetic particle pellets can either be incomplete or can take longer to complete. According to various embodiments, the magnet can have a strength ranging from about 1 millitesla (mT) to about 1 Tesla (T), or strengths above this range, for example 10 T. The magnet can be a single piece or can be multiple pieces, such as multiple magnets arranged in any configuration (e.g., stacked, aligned next to each other, and the like).

The magnets can be, for example, encased within a protective housing. According to various embodiments, the housing can further be capable of accepting a plurality of sample tubes, and one or more magnets can be arranged in the housing such that each sample tube is positioned within the housing adjacent to at least one magnet. According to various embodiments, multiple electromagnets can be used wherein each electromagnet is independently controlled, for example, using a dedicated power supply.

According to various embodiments, the system can comprise a plurality of sample tubes, each sample tube comprising a conical portion having a closed flat bottom and capable of holding a volume of magnetic particles contained therein. The system can further comprise one or more magnets positioned adjacent and below the plurality of sample tubes, wherein the one or more magnets are capable of providing a magnetic force sufficient to attract the magnetic particles to a respective flat bottom of each sample tube.

As illustrated in FIG. 19A, sample tube 1910 can have a longitudinal axis 1922, and magnet 1940 can provide a magnetic field 1942 that is aligned substantially parallel to longitudinal axis 1922. Magnetic field 1942 can maintain its substantially parallel alignment into the volume encompassed by sample tube 1910. Sample tube 1910 and magnet 1940 can be positioned adjacent such that magnetic field 1942 can be substantially aligned with longitudinal axis 1922. Additionally, the parallel alignment of magnetic field 1942 can vary slightly throughout the volume, without departing from the presently disclosed subject matter.

As illustrated in FIGS. 19A and 19B, flat bottom 1920 can comprise inner surface 1926, and magnet 1940 can provide magnetic field 1942 that is aligned substantially normal to inner surface 1926. Magnetic field 1942 can maintain its substantially normal alignment when penetrating a fluid within sample tube 1910 containing magnetic particles, and can have a substantially uniform strength along the entire inner surface 1926.

According to at least one embodiment, in a method of forming a magnetic particle pellet in a sample tube, a sample tube comprising a conical portion having a closed flat bottom, and defining an interior volume therein, and containing magnetic particles within the interior volume, can be provided. A magnet can be positioned adjacent and below the flat bottom, wherein the magnet is capable of providing a magnetic force sufficient to attract the magnetic particles to the flat bottom and forming a magnetic particle pellet in the flat bottom. According to various embodiments, the flat bottom can have an inner diameter and the magnetic particle pellet can have a pellet diameter that is substantially the same as or greater than the inner diameter.

According to various embodiments, the magnet can be positioned adjacent and below the flat bottom of the sample tube, and both the magnet and the sample tube can remain stationary (e.g., no turning needed) while the magnetic particle pellet is formed. According to various embodiments, the magnetic particle pellet can be formed on the flat bottom over a time ranging from about 1 second to about 5 minutes, or more, and in some embodiments, about 1 minute.

In at least one embodiment, a plurality of sample tubes can be provided, each sample tube comprising an elongated body and a conical portion having a closed flat bottom, and defining an interior volume therein. Each of the sample tubes can contain magnetic particles within the interior volume. The method can further comprise positioning one or more magnets adjacent and below the plurality of sample tubes, wherein the one or more magnets are capable of providing a magnetic force sufficient to attract the magnetic particles to a respective flat bottom of each sample tube. According to various embodiments, the magnetic force provided to each of the plurality of sample tubes can be substantially equivalent among each sample tube. According to various embodiments, the magnetic force can be provided to each sample tube for substantially the same time period. According to various embodiments, the magnetic force can start attracting the magnetic particles in each sample tube at substantially the same moment in time.

According to various embodiments, a system of detecting a signal can comprise a sample tube comprising a conical portion having a closed flat bottom and capable of holding a volume of magnetic particle complex containing therein. The sample tube can contain a volume of magnetic particle complex capable of generating a detectable signal. According to various embodiments, a magnet can be positioned adjacent and below the flat bottom of the sample tube. The magnet can be capable of providing a magnetic force sufficient to attract the magnetic particle complex contained within the volume to the flat bottom to form a magnetic particle complex pellet. According to various embodiments, the system can comprise a detector capable of detecting the signal generated from the magnetic particle complex in the formed pellet.

According to various embodiments, the magnetic particle complex can comprise a magnetic particle comprising a first capture probe specific to a target analyte, a SERS-active particle comprising a second capture probe specific to the target analyte, and the target analyte. The magnetic particle complex can be capable of generating a Raman signal. The complexes are separated from the solution by application of a magnetic field, and the optical signal from the resulting magnetic pellet is measured. SERS-labeled nanotags are further described, for example, in U.S. Pat. No. 6,514,767 B1; U.S. Pat. No. 7,192,778 B2; and U.S. Patent Application Pub. No. 2005/158870 A1, the disclosures of which are hereby incorporated by reference in their entirety. Magnetic capture agents and magnetic capture assays are further described in, for example, U.S. Pat. Nos. 5,945,281; 6,514,415 B2; and O. Olsvik, "Magnetic Separation Techniques in Diagnostic Microbiology," *Clinical Microbiology Reviews*, Vol. 7, 43-54 (1994), the disclosures of which are hereby incorporated by reference in their entirety. These methods and/or materials can be used in the presently disclosed subject matter.

According to various embodiments of the system, the sample tube can comprise a flat bottom comprising an optical window. A signal generated from the magnetic particle complex can be detected through the optical window. The signal can be, for example, a Raman signal. According to various embodiments, the detector can comprise a laser capable of interrogating the magnetic particle complex. The detector can comprise, for example, a spectrometer and/or a charge couple device. Referring to FIG. 4, an optical system for detecting a signal generated from a magnetic particle complex is illustrated. The system in FIG. 4 can be used with the sample tube and method of the presently disclosed subject matter.

According to various embodiments, a method of detecting a target analyte in a sample can comprise providing a sample tube comprising a conical portion having a closed flat bottom, and holding a volume of magnetic particle complex contained therein. The magnetic particle complex can comprise the target analyte and can be capable of generating a detectable signal. The method can further comprise positioning a magnet adjacent and below the flat bottom, wherein the magnet is capable of providing a magnetic force sufficient to attract the magnetic particle complex contained within the sample tube to the flat bottom and form a magnetic particle complex pellet. According to various embodiments, a magnetic particle complex pellet can be formed on the flat bottom. According to various embodiments, a signal generated from the magnetic particle complex pellet can be detected and analyzed to determine the presence or absence of the target analyte. In some embodiments, the quantitative amount and/or the identity of the analyte can be determined.

According to various embodiments of the method, a plurality of sample tubes can be provided. Each sample tube can contain a volume of magnetic particle complex comprising a target analyte. The method can further comprise positioning one or more magnets such that the magnetic force provided to each of the plurality of sample tubes can be substantially equivalent among each sample tube. According to various embodiments, the magnetic force can be provided to each sample tube for substantially the same time period. According to various embodiments, the magnetic force can start attracting the magnetic particle complex in each sample tube at substantially the same moment in time.

According to various embodiments of the method, the magnetic particle complex can comprise a magnetic particle comprising a first capture probe specific to the target analyte, a SERS-active particle comprising a second capture probe specific to the target analyte, and the target analyte. An example of the magnetic particle complex is illustrated in FIG. 1. According to various embodiments, the target analyte can comprise a first epitope and a second epitope that is different from the first epitope. The first capture probe can comprise a first moiety that specifically binds to the first epitope, and the second capture probe can comprise a second moiety that specifically binds to the second epitope. Consequently, a "sandwich" complex can be formed. According to various embodiments, the magnetic particle complex can be capable of generating a Raman signal.

In at least one embodiment, a magnetic particle comprising a first capture probe specific to a target analyte, a SERS-active particle comprising a second capture probe specific to the target analyte, and a sample to be analyzed are introduced into a sample tube. Appropriate conditions are further provided to allow a magnetic particle complex to form. For example, a magnetic particle complex, such as the "sandwich" complex illustrated in FIG. 1 can be formed. According to various embodiments, the method can comprise a plurality of sample tubes. One or more magnets can be positioned such that a substantially equivalent magnetic force can be provided to each sample tube at substantially the same moment in time. According the various embodiments, the magnetic particle complex formation can be quenched equivalently. The presently disclosed subject matter can use a light source, for example a laser, to interrogate the magnetic particle complex. The sample tube can comprise an optical window and the signal can be detected through the optical window. The signal can be detected using a spectrometer and/or a charge couple device.

Thus, with the presently disclosed subject matter, a magnetic pellet that is suitable for a magnetic capture assay can be achieved with a simpler process which preferably involves no turning of the tube and/or magnet to achieve a magnetic pellet for assay purposes, such as SERS or other detection techniques. A consistent homogenous and/or reproducible test can be achieved using the presently disclosed subject matter, such that a reproducible magnetic pellet in a sample tube can be formed having the desired characteristics and parameters sufficient for assay purposes as described herein. With the presently disclosed subject matter, the alignment of the magnet with the sample tube is not critical and a consistent homogenous and/or reproducible magnetic particle complex can be obtained which is capable of generating a detectable signal for assay purposes. In some past assay systems, alignment of the magnet was important, wherein if alignment was not proper, the magnetic particles would not form in a consistent and desirable manner sufficient to be used for assay purposes.

With the presently disclosed subject matter, another benefit is the ability of the presently disclosed subject matter to achieve quenching all at one time (for instance, within 10 minutes, within 5 minutes, within 1 minute, within 30 seconds, within 15 seconds, and the like). The design of the sample tube permits quenching to occur at essentially one time, such that the sandwiching is quenched and the antibody reaction is stopped, which permits one to achieve a better magnetic particle complex having the desirable contents for purposes of achieving an accurate, complete, and reproducible assay using SERS and the like.

Referring to FIG. 20, the results of a thyroid-stimulating hormone (TSH) assay are shown. The assay was performed using a sample tube according to an embodiment of the presently disclosed subject matter. The assay was performed in triplicate and the resulting binding curve is shown. The achieved minimum detection limit (MDL) and the reliable detection limit (RDL) are at least as good as typically observed using previous sample tube designs.

IV. Representative Target Analytes of Interest

The presently disclosed methods can be used to assess or measure the presence or amount of one or more target analytes in a biological sample. The term "analyte," as used herein, generally refers to a substance to be detected, which can be present or suspected of being present in a test sample. More particularly, an "analyte" can be any substance for which there exists a naturally occurring specific binder partner, such as a binding protein or receptor, or for which a specific binding partner can be prepared. Accordingly, an "analyte" is a substance that can bind one or more specific binding partners in an assay. In some embodiments, the analyte can be any compound, such as a metabolite, to be detected or measured and which has at least one binding site.

The target analytes can be any molecule or compound, of which the presence or amount is to be determined in a sample under test. Examples of classes of analytes that can be measured by the presently disclosed methods include, but are not limited to amino acids, peptides, polypeptides, proteins, carbohydrates, fatty acid, lipids, nucleotides, oligonucleotides, polynucleotides, glycoproteins, such as prostate specific antigen (PSA), proteoglycans, lipoproteins, lipopolysaccharides, drugs, drug metabolites, small organic molecules, inorganic molecules and natural or synthetic polymers. Examples of target analytes include, but are not limited to, glucose, free fatty acids, lactic acid, C-reactive protein and anti-inflammatory mediators, such as cytokines, eicosanoids, or leukotrienes. In some embodiments, the target analytes are selected from the group consisting of fatty acids, C-reactive protein, and leukotrienes. In another embodiment, the target analytes are selected from the group consisting of glucose, lactic acid and fatty acids.

More particularly, in some embodiments, the analyte can include glucose, as described hereinabove, prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen.

Prostate specific antigen (PSA) is a protein produced by the cells of the prostate gland and typically is present in small quantities in the serum of normal men. PSA can be elevated in men afflicted with prostate cancer or other prostate disorders. Normal PSA blood levels typically are considered to be between about 0.0 and 4.0 ng/mL, whereas PSA levels between 4 and 10 ng/mL (nanograms per milliliter) are considered suspicious.

Creatine kinase (CK), also known as phosphocreatine kinase or creatine phosphokinase (CPK) is an enzyme found predominately in the heart, brain, and skeletal muscle. Creatine kinase comprises three isoenzymes that differ slightly in structure: CK-BB (also referred to as CPK-1) is concentrated in the brain and lungs; CK-MB (also referred to as CPK-2) is found mostly in the heart; and CK-MM (also referred to as CPK-3) is found mostly in skeletal muscle. Diagnostic tests for specific CPK isoenzymes typically are performed when the total CPK level is elevated and can help differentiate the source of the damaged tissue. For example, an injury to the brain, e.g., a stroke, or lungs, e.g., a pulmonary embolism, can be associated with elevated levels of CK-BB. Further, CK-MM is normally responsible for almost all CPK enzyme activity in healthy subjects. When this particular isoenzyme is elevated, it usually indicates injury or stress to skeletal muscle.

CK-MB levels can be measured in subjects who have chest pain to diagnose whether they had a heart attack and/or as an as an indication for myocardial damage during heart attacks. Typically, CK-MB values exhibit a significant rise in CK-MB values in the first two to three hours after a heart attack. If there is no further damage to the heart muscle, the level peaks at 12-24 hours and returns to normal 12-48 hours after tissue death. CK-MB levels do not usually rise with chest pain caused by angina, pulmonary embolism (blood clot in the lung), or congestive heart failure. Elevated CK-MB levels also can be observed in subjects suffering from myocarditis (inflammation of the heart muscle, for example, due to a virus), electrical injuries, trauma to the heart, heart defibrillation, and open heart surgery. Blood serum CK-MB values measured in such assays typically range from about 0.0 to about 10 ng/mL. CK-MB values greater than about 5 ng/mL typically confirm a diagnosis of myocardial infarction.

Cardiac troponin I (cTnI) protein also is an independent predictor of major cardiac events. See, e.g., Polancyzk, C. A., et al., "Cardiac troponin I as a predictor of major cardiac events in emergency department patients with acute chest pain," *J. Am. Coll. Cardiol.*, 32, 8-14 (1998). cTnI values in blood serum measured in subject suspected of having a myocardial infarction range from about 0.4 ng/mL to about 1.5 ng/mL. Id. cTnI assays with lower detection limits of 0.1 ng/mL have the potential, however, to be more sensitive for detecting myocardial injury. Id.

Thyroid-stimulating hormone (TSH) is synthesized and secreted by thyrotrope cells in the anterior pituitary gland which regulates the endocrine function of the thyroid gland. TSH levels are tested in the blood of subjects suspected of suffering from an excess (hyperthyroidism) or deficiency (hypothyroidism) of thyroid hormone. Normal TSH levels in adults range from about 0.4 milli-international units per liter (mIU/L) to about 4.5 mIU/L. Current assays for TSH include sandwich ELISA for the measurement of TSH in blood serum or plasma, in which TSH in the sample is bound by anti-TSH monoclonal antibodies and then detected by spectrophotometry or colorimetry.

The presently disclosed assays also can be used to detect influenza viruses. Three types of influenza viruses exist: Influenzavirus A; Influenzavirus B; and Influenzavirus C. Influenza A (Flu A) and Influenza C (Flu C) infect multiple species, while Influenza B (Flu B) infects almost exclusively humans. Type A viruses are the most virulent human pathogens among the three influenza types and typically cause the most severe disease. Influenza A virus can be subdivided into different serotypes based on the antibody response to these viruses and include H1N1 (i.e., "Spanish Flu"); H2N2 (i.e., "Hong Kong Flu"); H5N1 (i.e., avian influenza strain or "Bird Flu"); H7N7; H1N2; H9N2; H7N2; H7N3, and H10N7. Influenza B is almost exclusively a human pathogen and is less common than Influenza A and only includes one serotype. The influenza C virus infects humans and pigs and can cause severe illness and local epidemics, but is less common than the other types.

Diagnostic tests available for influenza include rapid immunoassay, immunofluorescence assay, polymerase chain reaction (PCR), serology, and viral culture. Immunofluorescence assays entail staining of specimens immobilized on microscope slides using fluorescent-labeled antibodies for observation by fluorescence microscopy. Culture methods employ initial viral isolation in cell culture, followed by hemadsorption inhibition, immunofluorescence, or neutralization assays to confirm the presence of the influenza virus. Antigen detection assays to diagnose influenza infection include DIRECTIGEN™ EZ Flu A or DIRECTIGEN™ EZ Flu A+B test kits, (available from BD Diagnostic Systems, Sparks, Md.). Such rapid chromatographic immunoassays can be used for the direct detection of influenza A or influenza A and B viral antigens from nasopharyngeal washes/aspirates, nasopharyngeal swabs and throat swabs of symptomatic patients. Further, such diagnostic tests can be used to distinguish between influenza A and influenza B.

Respiratory syncytial virus (RSV) is the most common cause of bronchiolitis and pneumonia among infants and children under 1 year of age. RSV is a negative-sense, enveloped RNA virus. Diagnosis of RSV infection can be made by virus isolation, detection of viral antigens, detection of viral RNA, demonstration of a rise in serum antibodies, or a combination of these approaches. Traditional methods for detection of respiratory viruses have included cell culture and direct fluorescent antibody (DFA). Enzyme immunoassay (EIA) and rapid manual systems are available for specific viruses such as Influenza AB and RSV. Currently, most clinical laboratories use antigen detection assays to diagnose RSV infection, such as DIRECTIGEN™ EZ RSV test (available from BD Diagnostic Systems, Sparks, Md.), which is a rapid chromatographic immunoassay for the direct and qualitative detection of RSV antigen in nasopharyngeal washes, nasopharyngeal aspirates, nasopharyngeal swabs and nasopharyngeal swab/washes from subjects suspected of having a viral respiratory infection.

Accordingly, in some embodiments, the presently disclosed subject matter provides a method for detecting the presence or amount of a target analyte in a biological sample, e.g., blood serum, wherein the target analyte includes glucose, prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen, the method comprising contacting the biological sample with a reagent comprising one or more SERS-active nanoparticles having associated therewith at least one specific binding member having an affinity for the analyte, e.g., a specific binding protein or monoclonal or polyclonal antibody for the analyte of interest, and at least one SERS-active reporter molecule; illuminating the biological sample with incident radiation at a wavelength to induce the SERS-active reporter molecule to produce a SERS signal; and measuring the SERS signal to detect the presence or amount of analyte in the biological sample.

As used herein, the term "carbohydrate" includes, but is not limited to monosaccharides, disaccharides, oligosaccharides and polysaccharides. "Carbohydrate" also includes, but is not limited to, molecules comprising carbon, hydrogen and oxygen that do not fall within the traditional definition of a saccharide, i.e., an aldehyde or ketone derivative of a straight chain polyhydroxyl alcohol, containing at least three carbon atoms. Thus, for example, a carbohydrate as used herein can contain fewer than three carbon atoms.

The term "fatty acids," as used herein include all fatty acids, including free fatty acids (FFA) and fatty acids esterified to other molecules. Examples of specific fatty acids include, but are not limited to, palmitate, stearate, oleate, linoleate, linolenate, and arachidonate. The term "free fatty acid" is used herein as it is known in the art in that FFA are not part of other molecules, such as triglycerides or phospholipids. Free fatty acids also include non-esterified fatty acids that are bound to or adsorbed onto albumin. As used herein, the term "unbound free fatty acid" (unbound FFA) is used to denote a free fatty acid or free fatty acids that are not bound or adsorbed onto albumin or other serum proteins.

As used herein, the term "lipid" is used as it is in the art, i.e., a substance of biological origin that is made up primarily or exclusively of nonpolar chemical groups such that it is readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipds (or phospholipids), such as phosphatidic acid, phosphatidylethanolamine, phosphatidylcholine, phosphatidylserine, phosphatidylinositol, phosphatidylglycerol, and the like.

As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein. More particularly, the term "small organic molecule" as used herein, refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Further, in some embodiments, the presently disclosed subject matter provides a method of detecting one or more of a nucleic acid, e.g., deoxyribonucleic acid (DNA), a DNA fragment, a nucleotide, a polynucleotide, an oligonucleotide, and the like. Generally, the method comprises contacting one or more of a nucleic acid, a DNA fragment, a nucleotide, a polynucleotide, an oligonucleotide, with a presently disclosed SERS-active nanoparticle having an oligonucleotide attached thereto and detecting the presence of or a change in the SERS spectrum thereof. In exemplary embodiments, the oligonucleotides attached to the presently disclosed SERS active nanoparticles have a sequence, or sequences, complementary to portions of the sequence of the target nucleic acid, DNA fragment, nucleotide, polynucleotide, or oligonucleotide. A detectable SERS spectrum, and/or a change in the SERS spectrum, can be observed as a result of the hybridization of the oligonucleotide attached to the SERS active nanoparticle and the target nucleic acid, DNA fragment, nucleotide, polynucleotide, or oligonucleotide.

The presently disclosed SERS-active nanoparticles, the oligonucleotides, or both can be functionalized to attach the oligonucleotides to the nanoparticles. Such methods are known in the art. For example, oligonucleotides functionalized with alkanethiols at the 3'-termini or 5'-termini readily attach to nanoparticles, including gold and other metal nanoparticles. See, e.g., Whitesides, *Proceedings of the Robert A. Welch Foundation 39th Conference On Chemical Research Nanophase Chemistry*, Houston, Tex., pp. 109-121 (1996); see also, Mucic et al., *Chem. Commun.* 555-557 (1996) (describing a method of attaching 3' thiol DNA to flat gold surfaces which also can be used to attach oligonucleotides to nanoparticles).

Other functional groups suitable for attaching oligonucleotides to solid surfaces include phosphorothioate groups (see, e.g., U.S. Pat. No. 5,472,881 to Beebe et al., which is incorporated herein by reference in its entirety, for the binding of oligonucleotide-phosphorothioates to gold surfaces), substituted alkylsiloxanes (see, e.g., Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 (1995) for binding of aminoalkylsiloxanes and for similar binding of mercaptoakylsiloxanes). Oligonucleotides terminated with a 5' thionucleoside or a 3' thionucleoside also can be used for attaching oligonucleotides to solid surfaces.

Other methods are known in the art for attaching oligonucleotides to nanoparticles. Such methods are described in the following representative references. Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, John Wiley & Sons, New York (1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec et al., *J. Phys. Chem.*, 92, 2597 (1988) (rigid phosphates on metals).

Further, oligonucleotides functionalized with a cyclic disulfide, for example, cyclic disulfides having a 5- to 6-membered ring including at least two sulfur atoms, also are suitable for use with the presently disclosed subject matter. Suitable cyclic disulfides are available commercially or can be synthesized by known procedures. The reduced form of the cyclic disulfides also can be used. In some embodiments, the cyclic disulfide can further have a linker, for example, a hydrocarbon moiety, such as a steroid residue, attached thereto.

Each nanoparticle can have a plurality of oligonucleotides attached thereto. As a result, each nanoparticle-oligonucleotide conjugate can bind to a plurality of oligonucleotides or nucleic acids having a complementary sequence. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods can be used for oligoribonucleotides and oligodeoxyribonucleotides (known methods of synthesizing DNA also are useful for synthesizing RNA). Oligoribonucleotides and oligodeoxyribonucleotides also can be prepared enzymatically.

Accordingly, the presently disclosed subject matter provides a method for detecting nucleic acids. Any type of nucleic acid can be detected by the presently disclosed method. Therefore, the presently disclosed methods can be used in several applications where the detection of a nucleic acid is required, for example, in the diagnosis of disease and in sequencing of nucleic acids. Examples of nucleic acids that can be detected by the presently disclosed methods include, but are not limited to, genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, and the like.

Representative examples of the uses of the methods of detecting nucleic acids include, but are not limited to, the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, *Legionella* infections, *Mycoplasma* infections, *Salmonella* infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

The nucleic acid to be detected can be isolated by known methods, or can be detected directly in cells, tissue samples, biological fluids (e.g., saliva, urine, blood, serum, and the like), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Methods of preparing nucleic acids for detection with hybridizing probes also are well known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). If a nucleic acid is present in small amounts, it can be applied by methods known in the art, including polymerase chain reaction (PCR) amplification. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995).

One presently disclosed method for detecting nucleic acid comprises contacting a nucleic acid with one or more of the presently disclosed nanoparticles having oligonucleotides attached thereto. The nucleic acid to be detected can have at least two portions. The lengths of these portions and the distance(s), if any, between them are chosen so that when the oligonucleotides on the nanoparticles hybridize to the nucleic acid, a detectable SERS signal can be observed. These lengths and distances can be determined empirically and depend on the type of particle used and its size and the type of electrolyte present in solutions used in the assay (as is known in the art, certain electrolytes affect the conformation of nucleic acids).

Also, when a nucleic acid is to be detected in the presence of other nucleic acids, the portions of the nucleic acid to which the oligonucleotides on the nanoparticles are to bind must be chosen so that they contain sufficient unique sequence so that detection of the nucleic acid will be specific. Guidelines for doing so are well known in the art. The contacting of the nanoparticle-oligonucleotide conjugates with the nucleic acid takes place under conditions effective for hybridization of the oligonucleotides on the nanoparticles with the target sequence(s) of the nucleic acid. These hybridization conditions are well known in the art and can readily be optimized for the particular system employed. See, e.g., Sambrook et al., *Molecular Cloning: A Laboratory Manual* (2nd ed. 1989). In some embodiments, stringent hybridization conditions are employed.

Representative methods for detecting nucleic acids by using SERS-active nanoparticles having oligonucleotides attached thereto are disclosed in U.S. Pat. No. 7,169,556 to Park et al., which is incorporated herein by reference in its entirety.

As used herein, the term "sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

In some embodiments, the sample can be pre-treated prior to use, such as preparing plasma from blood, diluting viscous fluids, or the like. Such methods of treatment can involve filtration, distillation, concentration, inactivation of interfering compounds, and the addition of reagents.

The sample can be any sample obtained from a subject. The term "subject" refers to an organism, tissue, or cell from which a sample can be obtained. A subject can include a human subject for medical purposes, such as diagnosis and/or treatment of a condition or disease, or an animal subject for medical, veterinary purposes, or developmental purposes. A subject also can include sample material from tissue culture, cell culture, organ replication, stem cell production and the like. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a mammal or a mammalian cell. More preferably, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed.

The term "monitoring," such as in "monitoring the course of a disease or condition," refers to the ongoing diagnosis of samples obtained from a subject having or suspected of having a disease or condition.

The term "marker" refers to a molecule, such as a protein, including an antigen, that when detected in a sample is characteristic of or indicates the presence of a disease or condition.

The presently disclosed subject matter also provides methods for monitoring disease states in a subject, including chronic diseases, such as, but not limited to, heart disease, coronary artery disease, diabetes, metabolic disorders, inflammatory diseases, such as rheumatoid arthritis, and cancer. The metabolic disorders can include, but are not limited to, hyperlipidemia, hypolipidemia, hyperthyroidism, and hypothyroidism.

Further, the presently disclosed methods can be used to monitor specific markers of a chronic disease. By monitoring the concentrations of molecular artifacts, metabolites, and deleterious and/or beneficial molecules of a disease state, the subject's progression, regression or stability can be assessed, and treatments can, in turn be adjusted or revised accordingly. For example, markers for heart disease that could be monitored in vivo using the presently disclosed biosensors include, but are not limited to, total fatty acids, lactate, glucose, free fatty acids and various cardiotonic agents, such as, but not limited to cardioglycosides and sympathomimetics. Markers of diabetes include, but are not limited to, glucose, lactate and fatty acids. Likewise, markers for coronary artery disease include, but are not limited to, C-reactive peptide and free fatty acids. Generally, markers of various metabolic disorders include, but are not limited to, specific fatty acids.

The presently disclosed SERS-active nanoparticles also are suitable for use in devices for monitoring drug treatment. Indeed, the SERS-active nanoparticle can be designed to specifically bind a drug, drug candidate or a drug metabolite. In this manner, the plasma concentration of the drug could be monitored and dosages could be adjusted or maintained based on the concentration measurements provided by the SERS method. Accordingly, a pharmaceutical regimen could be individualized for a particular subject, including the use of a SERS-active nanoparticle that can specifically and reversibly bind the drug or drug metabolite to determine plasma concentrations of the drug. The concentrations provided by the SERS method can then be used to determine the bioavailability of the drug in the subject. The dose of the drug administered to the subject can then be altered to increase or decrease the bioavailability of the drug to the subject to provide maximum therapeutic benefits and avoiding toxicity.

The presently disclosed SERS-active nanoparticles also can be used to simultaneously monitor a variety of metabolites, the measurements of which could be used to profile the subject's metabolic or physical state. For example, during extended periods of strenuous exercise, glucose is broken down in anaerobic processes to lactic acid. The presently disclosed SERS-active nanoparticles can be used to determine lactate thresholds of athletes, to maximize the benefits of training and decrease recovery time. Similarly, the SERS-active nanoparticles can be used to determine lactate thresholds in soldiers to prevent fatigue and exhaustion and to decrease recovery time. To that end, the presently disclosed SERS-active nanoparticles can be used to monitor glucose levels, lactic acids levels and other metabolites during exercise or physical stress.

The presently disclosed SERS-active nanoparticles also can be used to monitor a condition or disease state in a patient in an acute care facility, such as an emergency room or a post-operative recovery room or a hospital. For example, in embodiments providing a method for monitoring glucose levels in a subject, studies have shown that mortality can be decreased by as much as 30% in post-operative patients when glucose levels are monitored and kept normal. Thus, the presently disclosed SERS-based diagnostic assays can be used in situations where monitoring glucose or other metabolites is essential to recovery or the overall health of the subject.

The amount of one or more analytes present in a sample under test can be represented as a concentration. As used herein, the term "concentration" has its ordinary meaning in the art. The concentration can be expressed as a qualitative value, for example, as a negative- or positive-type result, e.g., a "YES" or "NO" response, indicating the presence or absence of a target analyte, or as a quantitative value. Further, the concentration of a given analyte can be reported as a relative quantity or an absolute quantity, e.g., as a "quantitative value." The presently disclosed assays, in some embodiments, are capable of detecting an analyte of interest at a concentration range of about 5 fg/mL to about 500 ng/mL; in some embodiments, at a concentration range of about 10 fg/mL to about 100 ng/mL; in some embodiments, at a concentration range of about 50 fg/mL to about 50 ng/mL.

The quantity (concentration) of an analyte can be equal to zero, indicating the absence of the particular analyte sought or that the concentration of the particular analyte is below the detection limits of the assay. The quantity measured can be the SERS signal without any additional measurements or manipulations. Alternatively, the quantity measured can be expressed as a difference, percentage or ratio of the measured value of the particular analyte to a measured value of another compound including, but not limited to, a standard or another analyte. The difference can be negative, indicating a decrease in the amount of measured analyte(s). The quantities also can be expressed as a difference or ratio of the analyte(s) to itself, measured at a different point in time. The quantities of analytes can be determined directly from a generated signal, or the generated signal can be used in an algorithm, with the algorithm designed to correlate the value of the generated signals to the quantity of analyte(s) in the sample.

The presently disclosed SERS-active nanoparticles are amenable for use with devices capable of continuously measuring the concentrations of one or more analytes. As used herein, the term "continuously," in conjunction with the measuring of an analyte, is used to mean the device either generates or is capable of generating a detectable signal at any time during the life span of the device. The detectable signal can be constant, in that the device is always generating a signal, even if a signal is not detected. Alternatively, the device can be used episodically, such that a detectable signal can be generated, and detected, at any desired time.

V. Cellular Imaging

The small size of the presently disclosed SERS-active nanoparticles allow the nanoparticles to be incorporated into cells. For example, the use of SERS to study the complexation of a chemotherapeutic agent with DNA has been demonstrated. See Nabiev, I. R. et al., "Selective analysis of antitumor drug interactions with living cancer cells as probed by surface-enhanced Raman spectroscopy, *Eur. Biophys. J.*, 19, 311-316 (1991); Morjani, H., et al., "Molecular and cellular interactions between intoplicine, DNA, and topoisomerase II studied by surface-enhanced Raman scattering spectroscopy," *Cancer Res.*, 53, 4784-4790 (1993). SERS also has been used to investigate the mechanism of chemotherapeutic resistance to certain cancers. See Breuzard, G., et al., "Surface-enhanced Raman scattering reveals adsorption of mitoxantrone on plasma membrane of living cells,"*Biochem. Biophys. Res. Comm.*, 320, 615-621 (2004). Further, SERS has been used to characterize the distribution of particular chemicals within cells and to distinguish between the cytoplasm and the nucleus of the cell. See Kneipp, K., et al., "Surface-enhanced Raman spectroscopy in single living cells using gold nanoparticles," *Appl. Spectrosc.*, 56(2), 150-154 (2002).

Accordingly, in some embodiments, nanoparticles labeled with the reporter molecules can be used for cellular imaging, for example, to distinguish between abnormal cells, for example, a cell exhibiting an anomaly, such as a cancerous cell, versus normal cells in a biological sample. In such embodiments, the intensity of the Raman signal arising from the dye is proportional to the density of cells detected. Further, in some embodiments, the nanoparticles labeled with the reporter molecules also can be labeled with another species, such as a specific binding member of a binding pair, for example, an antibody, to facilitate binding to a cell of interest. The use of SERS-active nanoparticles for cellular imaging is described in U.S. Patent Application Publication Nos. 2006/0054506 and 2006/0046313, each of which is incorporated herein by reference in its entirety.

Accordingly, in some embodiments, the presently disclosed subject matter provides a method for detecting the presence of one or more target structures in a sample cell, the method comprising: (a) contacting one or more sample cells with one or more SERS-active nanoparticles labeled with one or more binding members under conditions suitable for binding of the one or more binding members to one or more target structures in the sample cell, wherein the SERS-active nanoparticle has associated therewith a reporter molecule capable of producing a distinguishable Raman signal; and (b) detecting one or more distinguishable SERS signals from the sample cell to indicate the presence of the one or more target structures in the sample cell.

In some embodiments, the presently disclosed SERS-active nanoparticles can be used for staining microstuctures within a cell. In such embodiments, the SERS-active nanoparticles can be labeled with at least one ligand that specifically binds to a known target microstructure or receptor. In some embodiments, a set of SERS-active nanoparticle probes can be used, wherein each member of the set comprises a combination of a ligand that specifically binds to a known target or receptor and one or more SERS-active dyes that can produce a distinguishable SERS signal upon binding with the target.

Under suitable conditions, the labeled SERS-active nanoparticles can specifically bind to receptors and other microstuctures within the cell. The "stained" cells can then be imaged, for example, by using a scanning Raman microscope to determine the presence and location of specific receptors and microstructures in the cells. Further, the SERS signals from individual Raman-active dyes associated with a particular ligand can be used to distinguish between specific receptors and microstructures in the cell and to create a profile of the receptors and microstructures in the cell. The profile of a target cell assayed according to the presently disclosed method can be compared with a profile similarly obtained from a normal cell of the same type to determine the presence of an anomaly in the target cell. The target cell can be either living or dead.

As used herein, the term "microstructure" includes, but is not limited to, extracellular matrix molecules, such as fibronectin and laminin; intracellular structures, such as actin filaments and microtubes; cell nucleus structures, such as histone; and the like. Suitable ligands for binding to such microstructures can be selected from the ligands disclosed herein, and include, but are not limited to, antibodies, such as anti-fibronectin antibodies and anti-actin antibodies, and other naturally-occurring ligands, such as anti-histone protein.

Images of cells containing Raman spectral information can be obtained by a variety of methods known in the art. For example, a microscope can be coupled to a charge-coupled device (CCD) camera such that complete images of the sample can be obtained. Typically, in such embodiments, a wavenumber (or wavelength) filtering device, such as a monochromator or liquid crystal tunable filter, can be inserted between the sample and the CCD camera. The filtering device allows only a narrow bandwidth of scattered radiation to reach the CCD camera at any one time. Multiple images can be collected by the CCD camera, wherein each image covers a particular spectral range of the scattered radiation. The spectra from each point in the image can be assembled in software. Alternatively, light from a single point of an image can be dispersed through a monochromator and the complete spectrum of that point can be acquired on an array detector. The sample can be scanned such that each point in the image is acquired separately. The Raman image is then assembled in software. In another approach, a line scan instrument can be constructed that excites the sample with a line of radiation. The line is imaged spatially along one axis of a CCD camera while simultaneously being spectrally dispersed along the orthogonal axis. Each readout of the camera acquires the complete spectrum of each spatial pixel in the line. To complete the image the line is scanned across the sample. An example of a Raman instrument suitable for imaging is described in Talley, et al., "Nanoparticle Based Surface-Enhanced Raman Spectroscopy," NATO Advanced Study Institute: Biophotonics, Ottawa, Canada (Jan. 6, 2005).

In some embodiments, the presently disclosed SERS-active nanoparticles can be incorporated into a cell or tissue by a passive uptake mechanism. Another mechanism for incorporating nanoparticles into cells is through the use of small peptide, which can bind to endocytotic receptors on the cell surface and draw the nanoparticles into the cell through endocytosis. See Tkachenko, A. G., et al., "Cellular trajectories of peptide-modified gold particle complexes: comparison of nuclear localization signals and peptide transduction domains," *Bioconjugate Chem.*, 15, 482-490 (2004). Further, the SERS-active nanoparticles can be introduced into cells via microinjection, transfection, electroporation, and endocytosis-mediated approaches, including the use of amphipathic peptides, such as PEP-1, the use of cationic lipid-based reagents, such as LIPOFECTAMINE™ (Invitrogen Corp., Carlsbad, Calif., United States of America), and the use of micelles and transfection reagents such as transferrin, mannose, galactose, and Arg-Gly-Asp (RGD), and other reagents such as the dendrimer-based reagent SUPERFECT™ (Qiagen, Inc., Valencia, Calif., United States of America). Intracellularly, indirect methods can be used to show that the particles are bound to the desired targets. One method suitable for demonstrating the specificity of the probes is immunofluorescence, which can be used to verify the location of the SERS-active nanoparticles. A number of commercially available fluorescent probes are useful for labeling cellular structures (such as the mitochondria, Golgi apparatus and endoplasmic reticulum) in living cells. By conjugating an antibody that targets the same structure, the fraction of nanoparticles that actively label their target can be determined. Likewise, what percentage of nanoparticles that are non-specifically bound also can be determined. Another approach to verifying the location of the SERS-active nanoparticles is to use fluorescent protein fusions, such as GFP and its analogs.

In some embodiments, imaging agents comprising the presently disclosed SERS-active nanoparticles are provided for use in medical diagnosis. The presently disclosed imaging agents are useful in imaging a patient generally, and/or specifically diagnosing the presence of diseased tissue in a patient. As described hereinabove, by selecting the size, shape, and composition of the nanoparticle core; the identity of the dye; and the composition and thickness of encapsulant, if desired, the optimum excitation and emission frequencies of the SERS-active nanoparticles can be tuned to occur between about 630 nm and about 1000 nm, i.e., the minimum region for absorption and scattering by tissues.

An imaging process can be carried out by administering an imaging agent comprising one or more presently disclosed SERS-active nanoparticles to a cell, a tissue sample, or to a subject, such as a patient, and then scanning the cell, tissue sample, or subject using any system known in the art that can perform spectral imaging, including, but not limited to spot scanning confocal microscopes, line scanning systems, and Optical Coherence tomographic systems. The presence of the presently disclosed SERS-active nanoparticle in a cell, tissue sample, or subject also can be observed by any imaging systems that detects over a single wavelength band, as well as any fluorescence imaging system that includes an excitation light source and filtered image detection. Other imaging systems suitable for use with the presently disclosed SERS-active nanoparticles are described in Tuchin, V. V., *Handbook of optical biomedical diagnostics*, Bellingham, Wash., USA: SPIE Press, 2002, which is included herein by reference in its entirety. Other imaging methods, including time domain methods, such as dynamic light scattering spectroscopy and tomography, time-of-flight imaging, quasi-elastic light scattering spectroscopy, photon-correlation spectroscopy, Doppler spectroscopy, and diffusion wave spectroscopy are suitable for use with the presently disclosed subject matter. All these techniques allow differentiation between photons and where they have been based on their time signatures. Because SERS-active nanoparticles can have different time signatures than fluorescent substances and the like, they can be discriminated against tissues and other labels with these methods. Useful instrument parameters also include a modulated light source and time sensitive detector. The modulation can be pulsed or continuous.

The scanning of the cell, tissue sample, or subject provides spectra or images of an internal region of the cell, tissue sample, or subject and can be used to detect or diagnose the presence of a condition or a disease state. By region of a cell, tissue sample, or subject, it is meant the whole cell, tissue sample, or subject, or a particular area or portion of the cell, tissue sample, or subject. When the subject is a patient, the presently disclosed imaging agents can be used to provide images of internal organs of the patient, including vasculature, heart, liver, and spleen, and in imaging the gastrointestinal region or other body cavities, or in other ways as will be readily apparent to those skilled in the art, such as in tissue characterization, blood pool imaging, and the like.

The presently disclosed subject matter also provides, in some embodiments, a method of diagnosing abnormal pathology in vivo, the method including introducing a plurality of SERS-active nanoparticles targeted to a molecule involved in the abnormal pathology into a bodily fluid contacting the abnormal pathology, wherein the SERS-active nanoparticles can become associated with the molecule involved in the abnormal pathology, and imaging the associated SERS-active nanoparticles in vivo. The presently disclosed method is generally applicable to any organ accessible by the SERS-active nanoparticle probes, including the gastrointestinal tract, heart, lung, liver cervix, breast, and the like.

In some embodiments, the presently disclosed SERS-active nanoparticles can be introduced into a subject via an endoscope, as in the case of a colonoscopy, or a needle, or used with a disposable tip or sleeve, or via endocytosis, transfection, microinjection, and the like. In other embodiments, the SERS-active nanoparticle probes can be introduced by directly introducing the imaging probe itself. In some embodiments, individual optical fibers, or bundles of optical fibers, can be introduced into live organisms for imaging. Such methods have been demonstrated for imaging of nerves, brain, microvessels, cells, as well as for characterizing biodistribution. Gel-coated optical fibers are well known in the sensor literature. The presently disclosed SERS-active nanoparticles can be non-covalently bound to the gel, wherein the nanoparticles can diffuse into the tissue upon introduction into the tissue. A variety of other methods to immobilize SERS-active nanoparticles on the outer surface of fibers such that they can diffuse into liquid phases to which they are contacted also are suitable for use with the presently disclosed subject matter.

In some embodiments, the presently disclosed subject matter provides a method for labeling an animal with a SERS-active nanoparticle, the method comprising introducing a SERS-active nanoparticle into the animal. The presently disclosed SERS-active nanoparticles can be introduced into an animal by any suitable method, including, but not limited to, any subcutaneous implantation method or intravenously. The SERS-active nanoparticle can be detected using appropriate instrumentation. In some embodiments, the presently disclosed subject matter provides an identification system for animals, including livestock and domesticated pets, wherein the SERS-active nanoparticle is implanted under the skin (or hide) of the animal to enable identification.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Magnetic Capture SERS Assay with Reference Labels

Nanoplex™ Biotags were purchased from Oxonica Inc. (Mountain View, Calif.). The particles were gold particles having a diameter of about 50 nm and labeled with Raman reporter selected from trans-1,2-bis(4-pyridyl)-ethylene (BPE) or 4,4'-dipyridyl (DPY) and encapsulated with glass as described herein. The glass encapsulant was biotinylated. Magnetic particles (approximately one micron in diameter) were purchased from Bangs Laboratories, Inc. (Fishers, Ind.) and labeled with streptavidin. Two solutions of biotinylated BPE- and DPY-labeled nanoparticles were mixed each with the streptavidin-coated magnetic particles. These two solutions were then mixed together in a ratio of 7:3 and a magnetic field was applied using a system of the type illustrated in FIG. 4, thereby forming a pellet at the bottom of the sample tube. The pellet was then repeatedly disrupted and reformed, and the Raman signal was measured for each pellet configuration, where the Raman signal from the BPE and DPY reporter were measured simultaneously. In the recorded Raman spectra the peak at 1590 cm$^{-1}$ corresponds to the BPE Raman reporter and the peak at 1180 cm$^{-1}$ corresponds to the DPY reporter.

The signal of the BPE reporter alone provides a measure of the repeatability of the signal when no referencing is used. Using the DPY reporter as a reference, the ratio of the BPE and DPY reporter is calculated. FIG. 3 shows a comparison of the non-referenced and referenced signal. The coefficient of variation for five rounds of pelleting and disruption is 8.4% for the non-referenced signal and 3.8% for the referenced signal. Therefore, the reduction in signal variation is reduced by 55%, when using a second reporter as a reference.

Example 2

Magnetic Capture SERS Assay with Lysis Reagent

Oxonica Nanoplex™ nanoparticles with surface thiol groups were labeled with goat anti-human cTnI polyclonal antibodies (BiosPacific, Emeryville, Calif.) using Sulfo-SMCC (sulfosuccinimidyl-4-(N-maleimidomethyl) cyclohexane-1-carboxylate). Separately, magnetic particles (Bioclone 1-µm BcMag® Carboxyterminated magnetic beads) were labeled with anti-human cTnI monoclonal antibodies (BiosPacific, Emeryville, Calif.) using 1-ethyl-3-[3-dimethylaminopropyl]carbodiimide hydrochloride (EDC). A master mix of antibody-labeled nanoparticles and magnetic particles was created, which resulted in each assay of 162 µL containing $5.1 \times 10^8$ nanoparticles and 15 µg magnetic particles. A lysing reagent solution also was prepared, containing 10 mM HEPES, 50 mM β-glycerophosphate, 70 mM NaCl, 2 mM EDTA, 1% Triton X100, and 1× Sigma Protease Inhibitor Cocktail P2714.

To test the impact of the lysing reagent on assay performance, samples were prepared consisting of PBS-diluted buffer, plasma, or blood. The samples were divided into four groups. In the first group, lysing reagent was added to each of the three media (buffer, plasma, and blood), and after approximately 10 minutes, the samples were spiked with cardiac Troponin I, previously dissolved in buffer, to a final concentration of 100 ng/mL. In the second group of samples, lysing reagent was again added, but, instead, buffer without Troponin I was added to constitute samples at 0 ng/mL. The third and fourth group consisted of control samples without lysing reagent, containing either 0 or 100 ng/mL Troponin I. For each sample, 100 µL of the sample was added to 62 µL of the Master Mix solution and incubated for 30 minutes (slow rotation, room temperature). The final concentration of biological fluid was 21% in the plasma and blood samples. The reactions were stopped by forming a magnetic pellet, and the SERS signal from the pellet in each tube was read on a custom instrument.

FIG. 6 shows the SERS signal levels with and without lysing reagent for 0 and 100 ng/mL cardiac Troponin I. Error bars on the graph indicate ±standard deviation from three replicates.

Example 3

Pellet Formation by Rotation of Sample Tube

Magnetic particles from Bangs Laboratories (approximately one micron in diameter) dispersed in water were used to form a dense pellet as follows. A magnet (e.g., a rod) is mounted below a sample tube, where the center of the magnet is positioned off center in respect to the sample tube axis (see FIG. 5). After a few seconds, the magnet induced formation of a pellet at the bottom of the sample tube. The sample tube was rotated around its center axis, thereby modulating the magnetic field experienced by the pellet in such a way that the pellet becomes denser. The schematic in FIG. 5 shows the process of pellet formation by rotating the sample tube above an off-center mounted magnet.

After the magnet has been placed below the sample tube, particles are captured by the magnet in a manner of seconds. The formed pellet can be irregular in shape and can resemble the cross section of a torus. After turning the sample tube around its own axis the pellet becomes denser. After some more turns, the pellet shape no longer changes. The resulting pellet is denser and smaller than the pellet formed without sample tube rotation.

Example 4

Improved Raman Reference Spectra

A multiplexing experiment was conducted where five different SERS-active nanoparticle, i.e., SERS-active nanoparticles having different Raman dyes, also referred to herein as "markers," were mixed together in varying proportions. A biotin-avidin binding technique was used to bind the nanoparticles to magnetic beads (approximately 1 micron in diameter). Pellets were formed as described in Example 3 immediately hereinabove. Spectra of the pelleted mixtures were analyzed using two sets of reference spectra: the nanoparticles in solution and the nanoparticles in magnetic bead-pellets.

Calibration curves were constructed using the fit weights for pellets containing each SERS-active nanoparticle alone. SERS-active nanoparticle concentrations were then estimated for each mixture. SERS-active nanoparticle concentrations ranged from 1.25E7 particles/mL to 2.5E8 particles/mL. Even though the reference spectra in solution and in pellets can be difficult to distinguish visually (see FIG. 12), the differences can be important for accurate estimation of low concentrations in a multiplexed system. The accuracy and precision for concentration estimates of zero and low concentrations were improved, as shown in Table 1.

TABLE 1

| Marker | Average Error | | | | | Standard Deviation of Errors | | | | |
|---|---|---|---|---|---|---|---|---|---|---|
| | 1 | 2 | 3 | 4 | 5 | 1 | 2 | 3 | 4 | 5 |
| Solution References | | | | | | | | | | |
| 0 | 1.50 | 0.23 | 0.28 | 0.32 | 0.05 | 1.46 | 2.67 | 0.39 | 0.56 | 0.32 |
| 1.25E+07 | 0.93 | 0.10 | 0.14 | 0.48 | 0.07 | 1.41 | 0.50 | 0.43 | 0.72 | 0.37 |
| 2.50E+08 | 0.53 | 2.81 | −1.49 | 6.07 | −1.16 | 4.92 | 6.40 | 5.63 | 6.86 | 5.67 |
| Pellet References | | | | | | | | | | |
| 0 | 0.24 | 0.30 | 0.17 | −0.22 | 0.03 | 0.22 | 2.60 | 0.14 | 0.47 | 0.22 |
| 1.25E+07 | 0.07 | 0.16 | 0.06 | 0.14 | 0.02 | 0.29 | 0.38 | 0.28 | 0.54 | 0.36 |
| 2.50E+08 | −1.57 | 2.99 | −1.63 | 5.01 | −1.20 | 4.29 | 6.37 | 5.61 | 6.47 | 5.55 |

Concentration estimates for marker 1 also are plotted in FIG. 13. Although the above description of this reference technique is based on signals generated by SERS-active nanoparticles coupled to magnetic particles and pulled into a pellet for Raman analysis, the concept is applicable to any situation where markers are configured in a particular configuration during detection that differs from an earlier configuration that might be used as a reference.

As shown in FIG. 11, a random signal can be erroneously assigned to input variables due to spurious alignment of features. Normally distributed random noise with a standard deviation of 10,000 was fit using a least-squares routine. Input signal 1100 is shown in FIG. 11A. The fitted spectrum 1110 reflects errors due to the random noise in input signal 1100. In this particular case, marker 4 was assigned a weight of 0.5 to balance negative weights of other markers. A fitted spectrum 1120 for marker 4 is shown in FIG. 11B.

Representative reference spectra are shown in FIG. 12. Referring to FIG. 12A, spectrum 1200 represents a SERS spectrum of marker 1 in solution, whereas spectrum 1210 represents a SERS spectrum of marker 5 in solution. Referring now to FIG. 12B, spectrum 1220 represents a SERS spectrum of marker 1 in a pellet, whereas spectrum 1230 represents a SERS spectrum of marker 5 in a pellet.

Although the foregoing subject matter has been described in some detail by way of illustration and example for purposes of clarity of understanding, it will be understood by those skilled in the art that certain changes and modifications can be practiced within the scope of the appended claims and equivalents thereof.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

That which is claimed:

1. An assay for detecting the presence or amount of one or more analytes in a biological sample, the assay comprising:
 (a) combining in a vessel containing a biological sample:
  i) a plurality of SERS-active nanoparticles that have associated therewith at least one binding member having an affinity for the one or more analytes, wherein the SERS-active nanoparticles produce a first detectable signal;
  ii) a plurality of magnetic particles, which have associated therewith: a) at least one binding member having an affinity for the one or more analytes; and b) a reference label that produces a second detectable signal;
 (b) forming a plurality of complexes of the SER-active nanoparticles, the magnetic particles and the one or more analytes;
 (c) using magnets that apply a localized magnetic field to the vessel, thereby forming a pellet of the plurality of magnetic particles and any complexes formed in step (b);
 (d) illuminating the pellet with incident radiation at one or more wavelengths;
 (e) obtaining a measure of the intensity of the first signal from the pellet;
 (f) obtaining a measure of the intensity of the second signal from the pellet; and
 (g) obtaining a ratio of the intensity of the first signal to the intensity of the second signal; and
 (h) determining a pellet feature from the ratio.

2. The assay of claim 1 wherein the pellet feature is selected from the group consisting of pellet shape, pellet density and pellet position and combinations thereof.

\* \* \* \* \*